United States Patent [19]
Gold et al.

[11] Patent Number: 5,792,742
[45] Date of Patent: Aug. 11, 1998

[54] FIBRIN-BINDING PEPTIDE FRAGMENTS OF FIBRONECTIN

[75] Inventors: Leslie I. Gold, New York; Agueda A. Rostagno, Elmhurst, both of N.Y.; Martin Baron, Oxford, United Kingdom; Iain D. Campbell, Oxford, United Kingdom; Michael J. Williams, Oxford, United Kingdom

[73] Assignees: New York University, New York, N.Y.; Isis Innovation Ltd., Oxford, England

[21] Appl. No.: 283,857

[22] Filed: Aug. 1, 1994

Related U.S. Application Data

[63] Continuation-in-part of Ser. No. 714,134, Jun. 14, 1991, abandoned.

[51] Int. Cl.$^6$ .......................... C07K 14/78; A61K 38/39
[52] U.S. Cl. ............................. 514/2; 424/9.1; 514/8; 530/350; 530/402; 435/69.6
[58] Field of Search ........................ 530/350, 380, 530/402, 387.1, 388.25, 389.3; 424/94.3, 9.1; 435/69.6, 188; 514/2, 8

[56] References Cited

U.S. PATENT DOCUMENTS

| | | | |
|---|---|---|---|
| 5,120,834 | 6/1992 | Gargan et al. | 530/388.25 |
| 5,270,030 | 12/1993 | Vogel et al. | 424/1.69 |

FOREIGN PATENT DOCUMENTS

| | | | |
|---|---|---|---|
| 1-261398 | 10/1989 | Japan | |
| 1261398 | 10/1989 | Japan | |
| 3123799 | 10/1989 | Japan | C07K 13/00 |
| 3-59000 | 3/1991 | Japan | |
| 3123799 | 5/1991 | Japan | |
| 9007577 | 7/1990 | WIPO | |
| 9117765 | 11/1991 | WIPO | |

OTHER PUBLICATIONS

Stathakis, N.E. et al., Cryoprecipitation of Fibrin–Fibrinogen Complexes Induced by the Cold–Insoluble Globulin of Plasma. *Blood* 51:1211–1222 (1979).

Nelles, L. et al., Characterization of a Fusion Protein Consisting of Amino Acids 1 to 263 of Tissue–Type Plasinogen Activator and Amino Acids 144 to 411 of Urokinase–Type Plasminogen Activator. *J. Biol. Chem.* 26:10855–10862 (1987).

Schnee, J.M. et al. Construction and Expression of a Recombinant Antibody–Targeted Plasminogen Activator *Proc. Natl. Acad. Sci. USA* 84:6904–6908 (1987).

Iwanaga, S. et al. Bovine Plasma Cold–Insoluble Globulin: Gross Structure and Function, *Ann. N.Y. Acad. Sci.* 312:56–73 (1978).

Ruoslahti, E. Fibronectin and its Receptors, *Ann. Rev. Biochem.* 57:375–413 (1988).

Garcia-Pardo, A. et al. Primary Structure of Human Plasma Fibronectin. *J. Biol. Chem.* 260:10320–10325 (1985).

Hayashi, M. et al. Domain Structure of the Carboxyl-Terminal Half of Human Plasma Fibronectin. *J. Biol. Chem.* 258:3332–3340 (1983).

Erickson, H.P. et al., Fibronectin Molecule Visualized in Electron Microscopy: A Long, Thin, Flexible Strand *J. Cell. Biol.* 91:673–678 (1981).

Robbins, K.C., et al. Covalent Molecular Weight ~92000 Hybrid Plasminogen Activator Derived from Human Plasmin Amino–Terminal and Urokinase Carboxyl–Terminal Domains, *Biochemistry* 25:3603–3611 (1986).

Baron, M. et al., Protein Modules, *Trends in Biochemical Science (TIBS)* 16:13–17 (1991).

Stemberger, A. et al., Affinity Chromatography of Immobilized Fibrinogen and Fibrin Monomer. II—The Behavior of Cold–Insoluble Globulin. *Hoppe–Seyler's Z. Physiol. Chem.* 357:1003–1005 (1976).

McMullen, B.A. et al., Amino Acid Sequence Ofteh Heavy Chain of Human $\alpha$–Factor XIIa (Activated Hageman Factor). *J. Biol. Chem.* 260:5320–5341 (1985).

Mosher, D.F. Cross–Linking of Cold–Insoluble Globulin by Fibrin–Stabilizing Factor. *J. Biol. Chem.* 250:6614–6621 (1975).

Pennica, D. et al., Cloning and Expression of Human Tissue–Type Plasminogen activator cDNA in *E. coli Nature* 301:214–221 (1983).

Patthy, L., Evolution of the Proteases of Blood Coagulation and Fibrinolysis by Assembly from Modules, *Cell* 41:657–663 (1985).

Doolittle, R.F., The Genealogy of Some Recently Evolved Vertegrate Proteins, *Trends Biochem. Sci.* 10:233–237 (1985).

Ritchie, J.L. et al. Noninvasive Thrombus Imaging with Technetium 99$^m$ Monoclonal Antibodiy F(ab')$_2$ to Fibrin (T2G1s) *JACC* 15:170A (1990).

Jung, M. et al., Deep Vein Thrombosis: Scintigraphic Diagnosis with IN–111–Labeled Monoclonal Antifibrin Antibodies, *Radiology* 173:469–475 (1989).

Knight, L.C. et al., Tc–99m Antifibrin FAB'Fragments FO Rimaging Venous Thrombi: Evaluation in a Canine Model[1] *Radiology* 173:163–169 (1989).

(List continued on next page.)

*Primary Examiner*—David L. Fitzgerald
*Attorney, Agent, or Firm*—Browdy and Neimark

[57] ABSTRACT

Fibrin-binding molecules are provided which include at least one peptide essentially corresponding to one or both of the following portions of the natural fibronectin molecule. The first portion is that portion which includes the $^4$F1,$^5$F1 module pair of fibronectin and includes no more of the natural fibronectin molecule than the N-terminal 25.9 kDa proteolytic fragment. The second portion includes the $^{10}$F1,$^{11}$F1 module pair of fibronectin and includes no more of the natural fibronectin molecule than the C-terminal 11 kDa proteolytic fragment. Also disclosed are nucleic acid molecules encoding the fibrin-binding peptides, methods for making the peptides, methods for using the peptides in the diagnosis and treatment of cardiovascular, peripheral vascular, cerebrovascular, and other conditions associated with fibrin deposition, and assay methods for detecting a fibrin-binding molecule and for measuring fibrin.

13 Claims, 33 Drawing Sheets

OTHER PUBLICATIONS

Alavi, A. et al. Radiolabeled Antifibrin Antibody in the Detection of Venous Thrombosis: Preliminary Results *Radiology* 175:79–85 (1990).

Kornblihtt, A.R., et al., "Primary Structure of Human Fibronectin: Differential Splicing May Generate at Least 10 Polypeptides From a Single Gene", *EMBO J.*, vol. 4, No. 7, pp. 1755–1759, 1985.

Garcia–Pardo, A., et al. (1985) *J. Biol. Chem.* 260: 10320–25.

Heene, D. L., et al., "Adsorption of Fibrinogen Derivatives on Insolubilized Fibrinogen and Fibrinmonomer", *Thrombosis Res.*, vol. 2, pp. 137–154, 1973.

Stenman, S., et al., "Fibronectin and Atherosclerosis", *Acta. Med. Scand. (Suppl.)* , vol. 642, pp. 165–170, 1990.

Jensen, B.A., et al., "Demonstration of Fibronectin in Normal and Injured Aorta by an Indirect Immunoperoxidase Technique", *Histochem.* , vol. 77, pp. 395–403, 1983.

Wagner, D.D., et al., "Domain Structure of Fibronectin and Its Relation to Function", *J. Biol. Chem.*, vol. 254, No. 14, pp. 6746–6754, 25 Jul. 1979.

Sekiguchi, K., et al., "Domain Structure of Human Plasma Fibronectin", *J. Biol. Chem.*, vol. 258, pp. 3967–3973, 25 Mar. 1983.

Sekiguchi, K., et al., "Topological Arrangement of Four Functionally Distinct Domains in Hamster Plasma Fibronectin: A Study with Combination of S–Cyanylation and Limited Proteolysis", *Biochemistry*, vol. 22, pp. 1415–1422, 1983.

An, S.S.A., et al., "The Two Polypeptide Chains in Fibronectin Are Joined in Antiparallel Fashion: NMR Structural Characterization", *Biochemistry* . vol. 31, pp. 9927–9933, 1992.

Peterson, T.E., et al., "Partial Primary Structure of Bovine Plasma Fibronectin: Three Types of Internal Homology", *Proc. Natl. Acad. Sci. USA* , vol. 80, pp. 137–141, Jan. 1983.

Kaplan, J.E., et al., "Fibronectin Augments Binding of Fibrin to Macrophages", *J. Lab. Clin. Med.*, vol. 113, No. 2, pp. 168–176, Feb. 1989.

Sekiguchi, K., et al., "Identification of Two Fibrin–binding Domains in Plasma Fibronectin and Unequal Distribution of These Domains in Two Different Subunits: A Preliminary Note", *Biochem. Biophys. Res. Comm.*, vol. 97, No. 2, pp. 709–715, 28 Nov. 1980.

McDonagh, R.P., et al., "Amino Acid Sequence of the Factor XIII$_a$ Acceptor Site in Bovine Plasma Fibronectin", *FEBS Lett.*, vol. 127, No. 2, pp. 174–178, May 1981.

McKeown–Longo, P.J., et al., "Interaction of the 70,000–mol–wt Amino–terminal Fragment of Fibronectin with the Matrix–assembly Receptor of Fibroblasts", *J. Cell. Biol.*, vol. 100, pp. 364–374, Feb. 1985.

Sottile, J., et al., "Five Type I Modules of Fibronectin Form a Functional Unit That Binds to Fibroblasts and *Staphylococcus aureus*\*", *J. Biol. Chem.*, vol. 266, pp. 12840–12843, 15 Jul. 1991.

Schwarzbauer, J.E., "Identification of the Fibronectin Sequences Required for Assembly of a Fibrillar Matrix", *J. Cell Biol.* , vol. 113, No. 6, pp. 1463–1473, Jun. 1991.

Williams, M.J., et al., "Secondary Structure of a Pair of Fibronectin Type I Modules by Two–Dimensional Nuclear Magnetic Resonance", *Biochemistry*, vol. 32, pp. 7388–7395, 1993.

Bennett, W.F., et al., "High Resolution Analysis of Functional Determinants on Human Tissue–type Plasminogen Activator", *J. Biol. Chem.*, vol. 266, No. 8, pp. 5191–5201, 15 Mar. 1991.

Suzuki, S., et al., "Complete Amino Acid Sequence of Human Vitronectin Deduced from cDNA. Similarity of Cell Attachment Sites in Vitronectin and Fibronectin", *EMBO J.*, vol. 4, No. 10, pp. 2519–2524, 1985.

Gold, L.I., et al., "Subtilisin and Cyanogen Bromide Cleavage Products of Fibronectin that Retain Gelatin–Binding Activity", *Proc. Natl. Acad. Sci. USA*, vol. 76, No. 10, pp. 4803–4807, Oct. 1979.

Rostagno, A.A., et al., "Biochemical Characterization of the Fibronectin Binding Sites for IgG", *J. Immunol.*, vol. 143, No. 10, pp. 3277–3282, 15 Nov. 1989.

Gold, L.I., et al., "Biochemical and Immunological Characterization of Three Binding Sites on Human Plasma Fibronectin with Different Affinities for Heparin", *Biochemistry*, vol. 22, pp. 4113–4119, 1983.

Owens, R.J., et al., "Mapping the Collagen–binding Site of Human Fibronectin by Expression in *Escherichia coli*", *EMBO J.*, vol. 5, No. 11, pp. 2825–2830, 1986.

Patel, R.S., et al., "Organization of the Fibronectin Gene Provides Evidence for Exon Shuffling During Evolution", *EMBO J.*, vol. 6, No. 9, pp. 2526–2572, 1987.

Koteliansky, V.E., et al., "A Study of the Structure of Fibronectin", *Eur. J. Chem.*, vol. 113, pp. 619–624, 1981.

Sibanda, B.L., et al., "Conformation of β–Hairpins in Protein Structures: A Systematic Classification with Applications to Modelling by Homology, Electron Density Fitting and Protein Engineering", *J. Molec. Biol.*, vol. 206, pp. 759–777, 1989.

Banyai, L., et al., "Common Evolutionary Origin of the Fibrin–Binding Structures of Fibronectin and Tissue–Type Plasminogen Activator", *FEBS Letter*, vol. 163, No. 1, pp. 37–41, Oct. 1983.

Baron, M., et al., "Structure of the Fibronectin Type 1 Module", *Nature*, vol. 345, pp. 642–646, 14 Jun. 1990.

Baron, M. et al., "Towards the Structure of Mosaic Proteins: Use of Protein Expression and NMR Techniques", *Protein Production in Biotechnology*, T.J.R. Harris, Ed., Elsevier, London, pp. 49–60, 1990.

Bennett, W.F., et al., "High Resolution Analysis of Functional Determinants of Human Tissue–Type Plasminogen Activator", *J. Biol. Chem.*, vol. 266, No. 8, pp. 5191–5201, 15 Mar. 1991.

Garcia–Pardo, A., et al., "Primary Structure of Human Plasma Fibronectin", *J. Biol. Chem.*, vol. 258, No. 20, pp. 12670–12674, 25 Oct. 1983.

Hormann, H., et al., "Affinity Chromatography on Immobilized Fibrin Monomer, III$^{1b}$", *Hoppe–Seyler's Z. Physiol. Chem.* , Bd. 361.S., pp. 1449–1452, Sep. 1980.

Kwaan, H.C., "The Role of Fibrinolysis in Disease Processes", *Sem. Thrombos. Hemostas.*, vol. 10, No. 1, pp. 71–79, 1984.

Markus, G., "The Role of Hemostasis and Fibrinolysis in the Metastatic Spread of Cancer", *Sem. Thrombos. Hemostas.*, vol. 10, No. 1, pp. 61–70, 1984.

Merrifield, B., "Solid Phase Synthesis", *Science*, vol. 23, pp. 341–347, 18 Apr. 1986.

Pierschbacher, M.D., et al., "Cell Attachment Activity of Fibronectin Can Be Duplicated by Small Synthetic Fragments of the Molecule", *Nature*, vol. 309, pp. 30–33, 3 May 1984.

Shekhonin, B.V., et al., "Visualization of apo B, fibrinogen/fibrin, and fibronectin in the intima of normal human aorta and large arteries and during atherosclerosis", *Atherosclerosis*, vol. 82, pp. 213–226, 1990.

Skerrett, P.J., "Matrix Algebra' Heals Life's Wounds", *Science*, vol. 252, pp. 1064–1066, May 1991.

Williams, M.J., et al., "Solution Structure of a Pair of Fibronectin Type 1 Modules with Fibrin Binding Activity", *J. Mol. Biol.*, vol. 235, pp. 1302–1311, 1994.

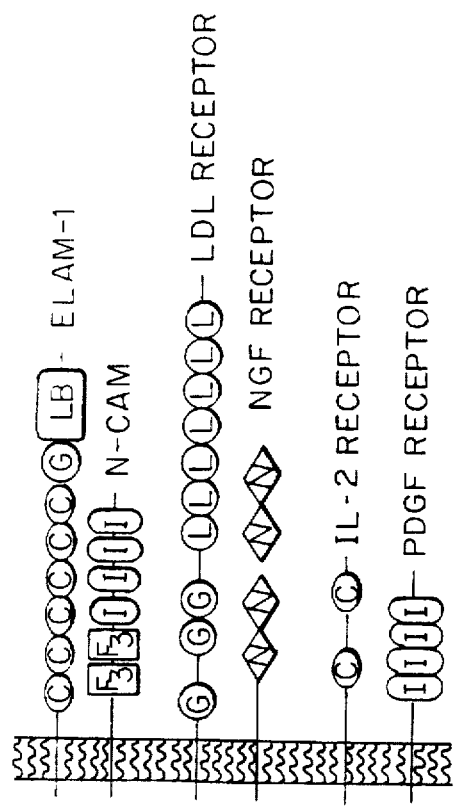

FIG. 5A

```
     1
     QAQQMVQPQSPVAVSQSKPG
                        20                    40                    60
                        CMDN..GKHVDINQQMERTY.LGNVLV.DTDYYGSRGL.FNCESKPEAEET
                        CFDKYTGNTVRVGDTVERPKDS..MIWDCTCIGARGRISCTIANR
                                        80                    100
                        CHEG..SQSYKIGDTWRRPHETGYMLEQVCLGNGKGEWTQKPIAEK
                                    120                    140
        I               CEHAAGTSYVVEITWEKPY.QGMMVDCTCLGEGSGRITCTSRNR
                                    160                    180
                        CNDQDTRTSYRIIGDTWSKKDNRGN.LLQCICTGNGRGEWKCER
                                        200                    220                    240
```

25.9 kDa fibrin-binding domain

FIBRIN
HEPARIN
S AUREUS

BINDING SITES

```
                        HTSVQTTSSGSGPFTDVRAAVYQPQPHPQPPPYGH
                            260                    280
     I                  CVTDS.GVVLSGVVMLKI..TQGNKQMLEICLENG...VSCQE
                                    300                    320
     II                 HAVTQTYFGNSNGEPCVLPFIYNGRTFYSCTTEGRQLGHLWCSTTSNYEQDQKYSFCTDH
                                    340                    360
                        IVLVQTQGGNSNGA.LCHFPFLVNNHNYTDCTSEGRIDNMKWCGTTDNYDADQKFGECPMAAHEEI
                                    380                    400                    420
     I                  CTTNE.GVMYRIGDQMFKQHD.MGHMMRCTCVGNGRGEWTCVAYSQLRDQ
                                    440                    460                    480
                        CIVD..DITYNVNDTFHKRHE.EGHMLNCTCFGQGRGRWKCDPVDQ
                                    500                    520
                        CQDSEIGTFYNDIGSWEK..YVHGVRYQCYCYGRGIGEWHCDPLQTYPSS
                                    540                    560                    580
```

COLLAGEN

```
     I[I] SGPVEVFITETPSQPNSHP.TQWNADQPSHISKILLRWREKNSVGRWKEATIPGHLNSV.TIKGILKPGVVTFEGQLISIQQ...YGHQEVTRFDFTTT
                                    600                    620                    640                    660
            STSTPVTSNTVTGETTPF
                                    680                    700
            SPLVATSESVTEITASSFV.MSWVSASDT.VSGFRVEYELSEEGDEPQYLDLPSTATSV.NTPDLLPGRKYINVYQISE....DGEQSLTLSTSQTT
                                    720                    740                    760
            APDAPDPTVDQVDTSIV.VRWSRPQAP.ITGYRIVYSPSVEGSSTELN.LPETANSV.TLSDLQPGVQYNITIYAVEE....NQE.STPVVIQQETTGTPRSD
                                    780                    800                    820                    840                    860
```

DNA

110 RESIDUES

POLYMERASE CHAIN REACTION
FIBRONECTIN DOMAIN DNA SEQUENCE SYNTHESIS

☐ COMPLEMENTARY PCR OLIGONUCLEOTIDE

THE OLIGONUCLEOTIDES FOR MODULE PAIR ($^4F1.^5F1$) INSERT (A) ($^4F1.^5F1$) A OLIGO:

5'- GCT-GAG-AAG-TGT-TTT-GAT-CAT-G-  (+)

1st
N-TERMINAL
CODON (B) ($^4F1.^5F1$) B OLIGO:

5'- TAAT-GGA-TCC-TTA-AGA-GGT-GTG-CCT CTC-ACA-CT- (-)

BamH1  STOP LAST
           CODON

FIG. 15
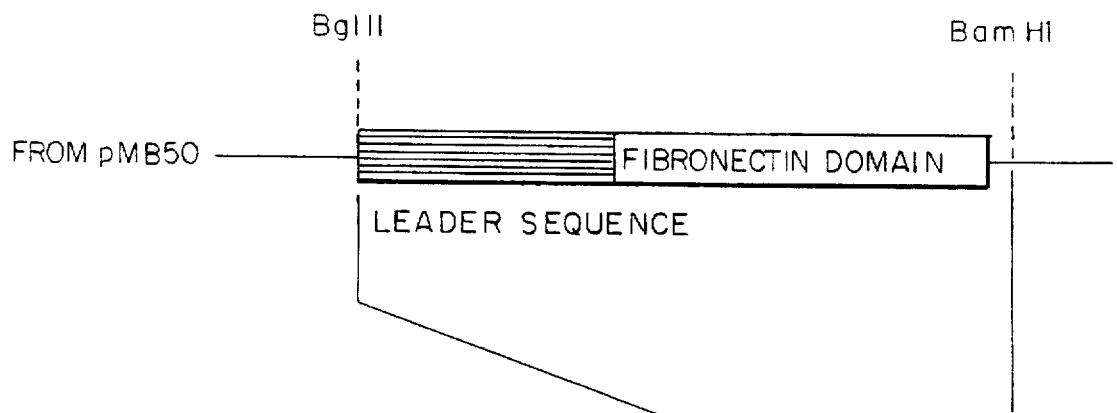
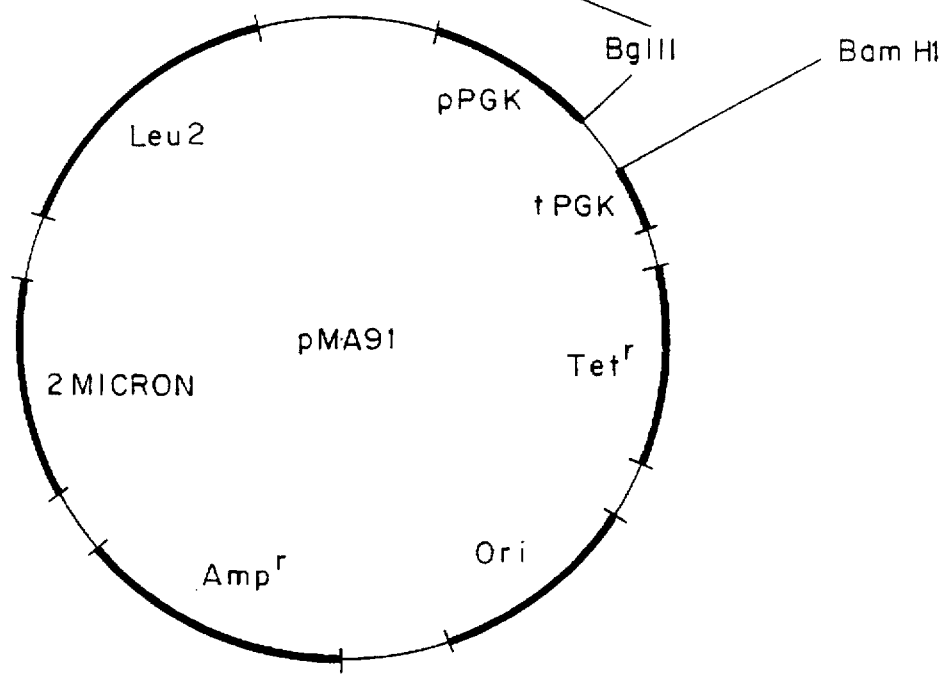
FIG. 16
ALPHA-FACTOR / Fn1 FUSION PEPTIDE
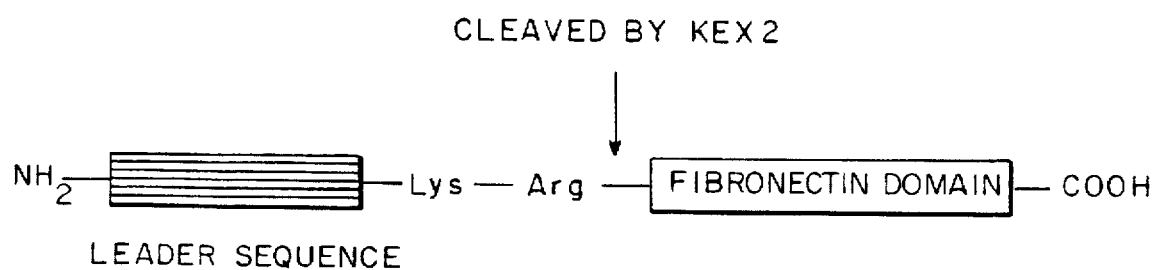

FIG. 19

```
consensus:   C--  ----  --y  --t-  -a-r-  ---t--  ---C-C  hG-t-tp  h-C  <linkers>

1F1  CYD  --NG  KHY  QINQ  QWERT  -YLGN-  VLVCTC  YGGSRG-  FNC  ESKPEAEET
 2F1  CFD  KYTG  NTY  RVGD  TYERP  -KDSM-  IWDCTC  IGAGRGR  ISC  TIANR
 3F1  CHE  --GG  QSY  KIGD  TWRRP  HETGGY  MLECVC  LGNGKGE  WTC  KPIAEK
 4F1  CFD  HAAG  TSY  VVGE  TWEKP  -YQGWM  MVDCTC  LGEGSGR  ITC  TSRNR
 5F1  CND  QDTR  TST  RIGD  TWSKK  DNRGN-  LLQCIC  TGNGRGE  WKC  ERHTS (32 residues)
 6F1  CVT  -DSG  VVY  SVGM  QWLKT  --QGNK  QMLCTC  LGNG---  VSC  Q (2xF2)
 7F1  CTT  -NEG  VMY  RIGD  QWDKQ  HDMGH-  MMRCTC  VGNGRGE  WTC  IAYSQLRDQ
 8F1  CIV  -DD-  ITY  NVND  TFHKR  HEEGH-  MLNCTC  FGQGRGR  WKC  DPVDQ
 9F1  CQD  SETG  TFY  QIGD  SWEKY  -VHGV-  RYQCYC  YGRGIGE  WHC  Q (15-17xF3)
10F1  CFD  PYTV  SHY  AVGD  EWERM  SESGF-  KLLCQC  LGFGSGH  FRC  DSSRW
11F1  CHD  --NG  VNY  KIGE  KWDRQ  GENGQ-  MMSCTC  LGNGKGE  FKC  DPHEAT
12F1  CYD  --DG  KTY  HVGE  QWQKE  -YLGA-  ICSCTC  FGGWRG-  WRC  DNC factor XII:  CFE  PQLL  RFF  HKNE  IWYRT  -EQAA-  VARCQC  --KGPD-  AHC  Q
t-PA:        CRD  EKTQ  MIY  QQHQ  SWLRP  VLRSNR  VEYCWC  ---NSGR  AQC  H -sheet residues  :..  :      :..   :      :..      :..              :..
-strand           A    B       C    C       C       C                E
``` factor XII:
t-PA:

-sheet residues
-strand

N-TERMINAL FIBRIN BINDING DOMAIN

46 AMINO ACIDS

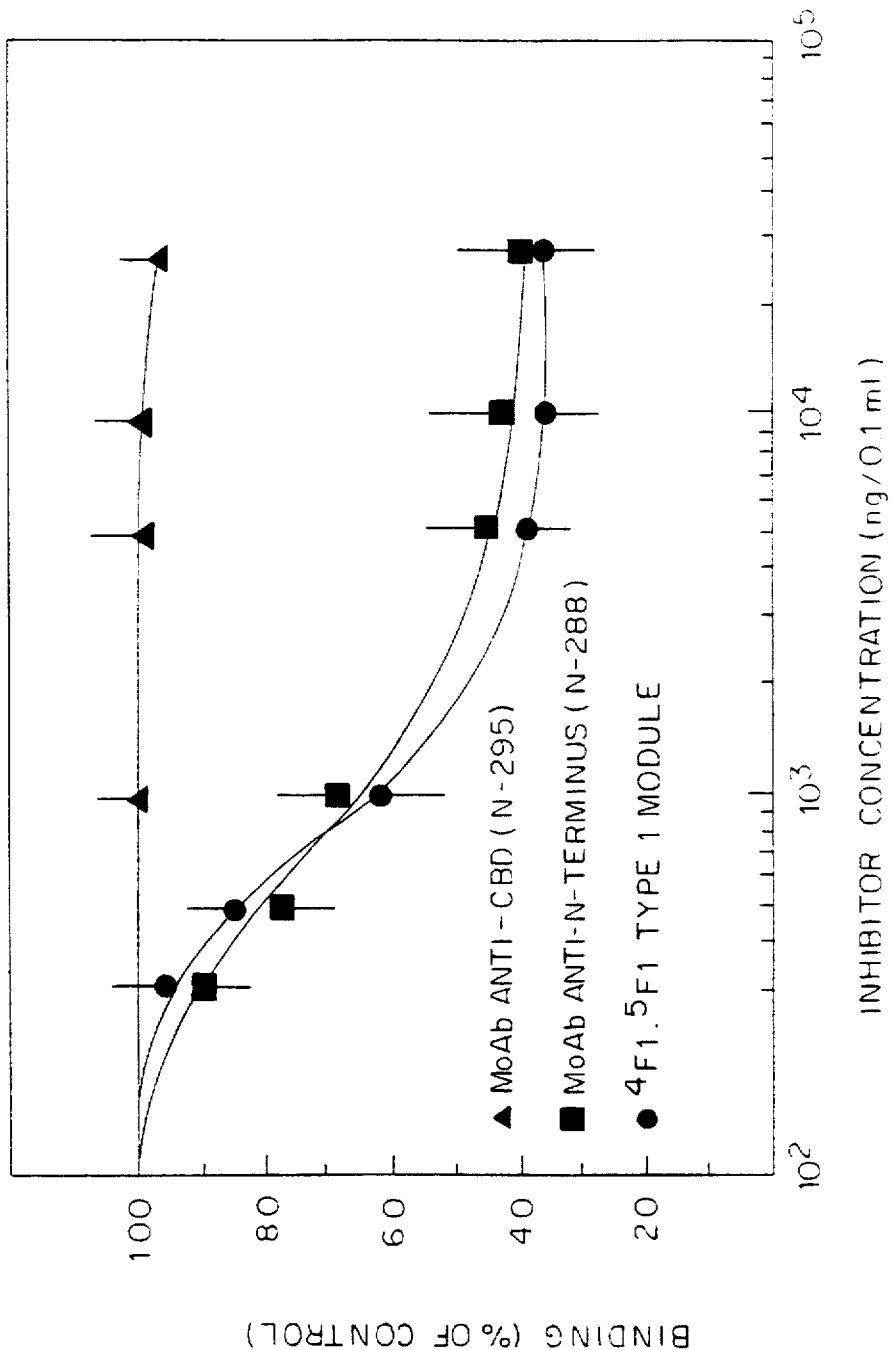

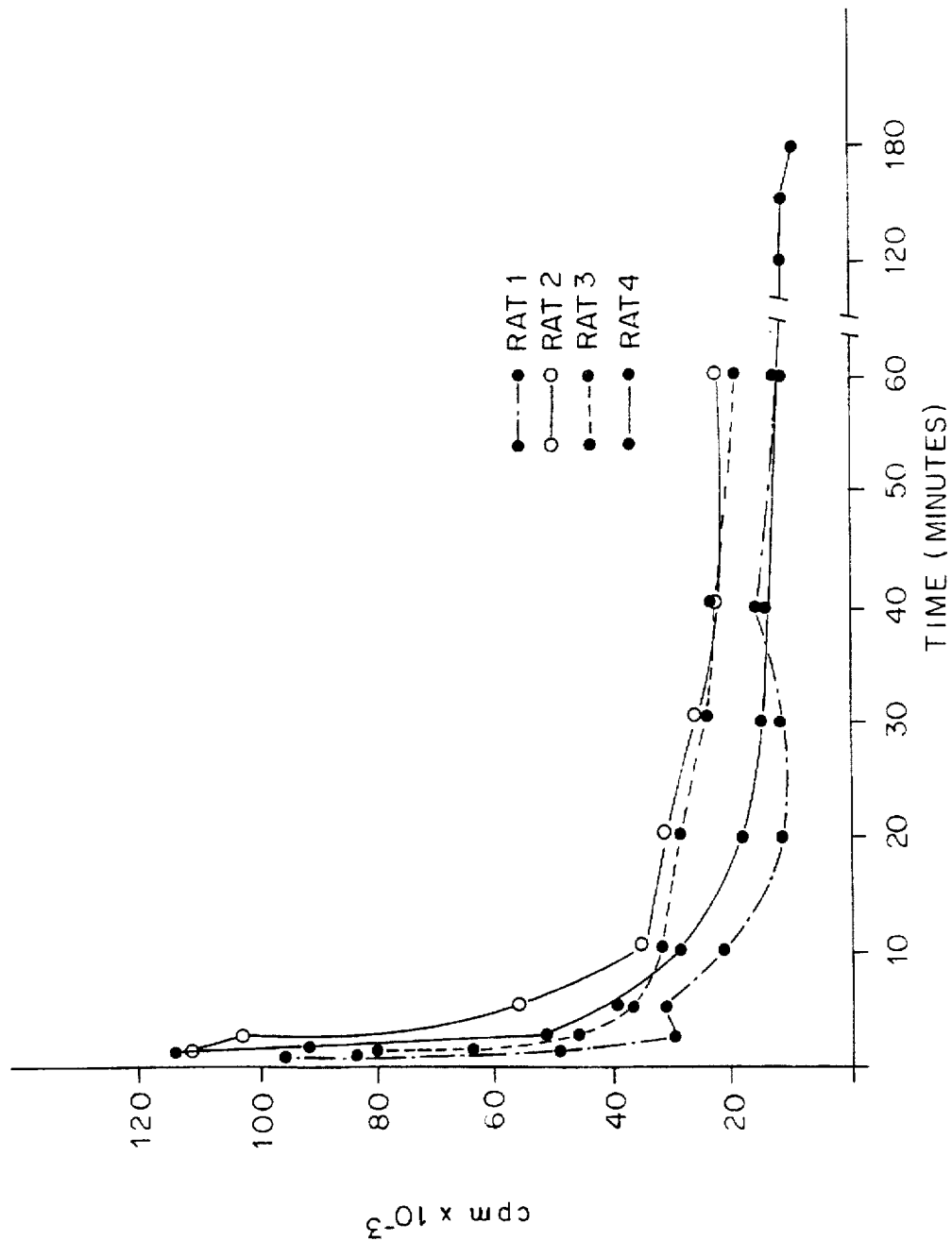

FIBRIN-BINDING PEPTIDE FRAGMENTS OF FIBRONECTIN

This application is a continuation-in-part of application Ser. No. 07/714,134, filed 14 Jun. 1991, now abandoned.

BACKGROUND OF THE INVENTION

1. Field of the Invention

The present invention relates to isolated fibrin-binding peptides (FBPs), DNA encoding these peptides, and methods for making and/or using such peptides in diagnosis and/or therapy, such as for detecting fibrin in or associated with any tissue (e.g., in a thrombus or atherosclerotic lesion) and measuring fibrin-binding biological activity.

2. Description of the Background Art

Fibronectin and Fibrin in Wound Healing, Thrombosis and Atherosclerosis. Fibronectin is a 440 kDa molecular weight glycoprotein, which is involved in blood clotting. Fibronectin's action in wound healing stems in part from its ability to bind both fibrin and the gpIIIa-IIb integrin receptors on platelets (Skerret, *Science* 252:1064–1066 (1991)). Fibrin is a component of both thrombi and atherosclerotic lesions. There is a great need for diagnostic and therapeutic agents with the ability to target fibrin and deliver agents capable of imaging or treating thrombi or atherosclerotic plaque (Stenman et al., *Acta. Med. Scand.* 642:165–170 (1980); Jensen et al. *Histochem.* 77:395–403 (1983)).

Fibronectin binds to the C-terminal portion of the fibrin A α-chain (Mosher, *J. Biol. Chem.* 250:6614–6621 (1975); Stemberger et al., *Hoppe-Seyler's Z. Physiol. Chem.* 357: 1003–1005 (1976); Iwanaga et al., *Ann. N.Y. Acad. Sci.* 312:56–73 (1978); Stathakis et al., *Blood* 51:1211–1222 (1978)). Two separate fibronectin domains are involved in fibrin binding, one in the N-terminal half and one in the C-terminal half of the molecule. Both sites are on each subunit of human plasma fibronectin. The fibrin-binding site in the N-terminal 29 kDa tryptic fragment of fibronectin has been identified (Erickson et al., *J. Cell Biol.* 91:673–678 (1981); Garcia-Pardo et al., *J. Biol. Chem.* 258:12670–12674 (1983); Hayashi et al., *J. Biol. Chem.* 258:3332–3340 (1983)). This domain lacks carbohydrate (Wagner et al., *J. Biol. Chem.* 254:6746–6754 (1979)), and has a surprisingly large number of other binding interactions.

A second fibrin-binding site, close to the C-terminus of both the A and B subunits of human plasma fibronectin, is a high affinity binding site (Hayashi, M. et al., *J. Biol. Chem.* 258:3332–3340 (1983); Sekiguchi, K. et al., *J. Biol. Chem.* 258:3967–3973 (1983); Sekiguchi, K. et al., *Biochemistry* 22:1415–1422 (1983); Garcia-Pardo, A. et al., *J. Biol. Chem.* 260:10320–10325 (1983)).

Fibronectin is a multifunctional protein (for general reviews see Ruoslahti, *Ann. Rev. Biochem,* 57:375–413, 1988, Mosher et al., *Fibronectin*, Academic Press, New York 1989 and Hynes, Fibronectins, Springer-Verlag, New York, 1990). The protein is secreted into the extracellular environment as a dimer of various different monomer isoforms joined near their C-termini by two anti-parallel disulfide bonds (An et al., *Biochem* 31:9927–9933, 1992). The dimer is found in plasma and as an insoluble matrix upon which cells attach and migrate. soluble plasma fibronectin plays an important role in wound healing, acting as a constituent of blood clots, due to its affinity for fibrin (Stathakis et al., 1978). The plasma and cellular forms are not identical due to differential alternative mRNA splicing of portions of the C-terminus, however, they both contain two fibrin-binding sites, i.e., the N-terminal and C-terminal sites, on each monomer.

Fn is a mosaic protein comprised of numerous members of three different protein module families, classified as module types 1 (F1), 2 (F2), and 3 (F3) (Petersen (1983) *Proc. Nat'l. Acad. Sci. USA* 80, 137–141; Kornbliht (1985) *EMBO J.* 4, 1755–1759), that are characterized by conserved consensus sequences of approximately 43–45, 60, and 90 amino acid residues, respectively. The nomenclature used herein with respect to such modules is as follows. Each single region of sequence homology expressed is called a "module". Two regions expressed together are called a "module pair", three would thus be called a "module triplet", and so on. The three types of module in fibronectin are identified as F1, F2 and F3. Particular modules in the fibronectin molecule can be identified by a number positioned to the top left-hand side of the module type identifier. This number is such that the first occurrence of that module type from the N-terminus is number 1, i.e., the fourth type 1 module is ($^4$F1). If more than one module are expressed together, a full stop (period) is used to separate the module identifiers for each repeat. Thus, for example the second type 2 module linked to the seventh type 1 module would be known as module pair ($^2$F2.$^7$F1).

Each Fn monomer consists of six consecutive N-terminal type 1 modules, followed by two type 2 modules and three further type 1 modules. Subsequently, a chain of 15–17 type 3 modules leads into three type 1 modules at the C-terminus. A major characteristic of the type 1 and 2 structures is the placement of cysteines resulting in specific disulfide bond formation. Type 3 modules typically do not contain cysteines; the Arg-Gly-Asp-Ser sequence that binds cell surface integrin receptors is within this structure in the tenth type 3 module ($^{10}$F3) (Piersbacher (1984) *Nature* 309, 30–33).

The three Fn module families have been studied extensively by nuclear magnetic resonance (NMR) techniques and solution tertiary structures for members of all three have been reported. These include the seventh type 1 module from Fn (Baron (1990) *Nature* 345, 6420–646), the single type 1 module from tissue-type plasminogen activator (Downing (1992) *J. Mol. Biol.* 225, 821–833), a type 2 module from PCD-109 (Constantine (1992) *J. Mol. Biol.* 223, 281–298) and the tenth type 3 module from Fn (Main (1992) *Cell* 71, 671–678). In addition, the crystal structure of a type 3 module of tenascin has been determined (Leahy (1992) *Science* 258, 987–991. These isolated structures provide characteristic conserved "consensus" folds for each class of module.

The modules of Fn are organized into several proteolytically resistant domains that harbor specific ligand binding activities (Hynes (1990) *Fibronectins*, Springer-Verlag, New York). Because of these various protein interactions, Fn plays important roles in many diverse biological activities including wound healing, phagocytosis, cell matrix assembly, and both cellular adhesion and migration. The role of Fn in wound healing is mediated through its affinity for fibrin (Stathakis (1978) *Blood* 51, 1211–1222; Mosher (1975) *J. Biol. Chem.* 250, 6614–6621) and by its ability to bind to integrins on platelets (Hynes (1990) *Fibronectins,* Springer-Verlag, New York). The interaction of Fn with fibrin is also important in augmenting the binding of fibrin to macrophages for subsequent phagocytosis (Kaplan (1989) *J. Lab. Clin. Med.* 113, 168–176), and in tissue debridement and wound repair. Both the $NH_2$- and COOH-terminal domains of Fn (consisting of five ($^1$F1–$^5$F1) and three ($^{10}$F1–$^{12}$F1) consecutive type 1 modules respectively) have previously been reported to bind to fibrin (Hormann (1980) *Hoppe-Seyler's Z. Physiol. Chem.* 361, 1449–1452; Sekiguchi (1980) *Biochem. Biophys. Res. Comm.* 97, 709–715;

Sekiguchi (1982) *J. Biol. Chem.* 258, 3967–3973; Hayashi (1983) *J. Biol. Chem.* 258, 3332–3340; Garcia-Pardo (1983) *J. Biol. Chem.* 258,12670–12674; Garcia-Pardo (1985) *J. Biol. Chem.* 260, 10320–10325. Although the level of affinity of the $NH_2$-terminal of Fn for fibrin is relatively low under physiological conditions (Garcia Pardo (1985) *J. Biol. Chem.* 260, 10320–10325), this domain can undergo transglutaminase catalyzed covalent cross-linking to fibrin between the Gln3 residue of Fn and a lysine residue from fibrin (McDonagh (1981) *FEBS Lett.* 127, 174–178). This acts to stabilize the interaction of Fn with fibrin within developing blood clots, allowing Fn to form a stable matrix at the wound site, upon which various cell types and extracellular matrix proteins can attach. Furthermore, the $NH_2$-terminal type 1 modules ($^1F1$–$^5F1$) mediate the binding of soluble Fn to cell surfaces and possess a site involved in autopolymerization; they are thereby involved in Fn fibril formation and matrix assembly (McKeown-Longo (1985) *J. Cell Biol.* 100, 364–374; Sottile (1991) *J. Biol. Chem.* 266, 12840–12843; Schwarzbbauer (1991) *J. Cell. Biol.* 113, 1463–1473.

The tertiary structures of two of these proteins, $^7F1$ and the $^4F1.^5F1$ module pair, have previously been determined by two dimensional $^1H$ nuclear magnetic resonance (NMR) techniques (Baron (1990) *Nature* 345, 642–646; Williams (1993) *Biochemistry* 32, 7388–7395). No functional characteristics were ascribed for either the module or module pair. The conserved type 1 "consensus" structure of these modules consists of an N-terminal double stranded antiparallel β-sheet to enclose a hydrophobic core of conserved residues. The fold is further constrained by two conserved disulfide bonds which link together in the pattern 1–3 and 2–4.

The single type 1 module from tissue plasminogen activator (t-PA-F1) has also been implicated in fibrin binding (Bennet et al., *J. Biol. Chem.*, 1991; Banjai et al., 1983; Sottile et al., *Biochem.* 32:1641–1647, 1991). The interaction between fibronectin and fibrin is further stabilized by Factor XIIIa transglutaminase-catalyzed crosslinking of $Gln^3$ from the N-terminus of fibronectin, to a lysine residue of fibrin (McDonagh et al., *FEBS Lett.* 127:174–178, 1981).

Other proteins have the capacity to bind to fibrin, such as tissue plasminogen activator (tPA), as above, lipoprotein a ((Lp(a)) and plasminogen (Lozcalzo, et al., *Arteriosclerosis* 10:240–245 (1990)). Fibrin has been identified in the intima of normal and atherosclerotic human aorta and large arteries, e.g., as show n using a monoclonal antibody (mAb) specific for the C-terminal region of human fibrinogen A α-chain (Shekhonin et al., *Atherosclerosis* 82:213–226 (1990)).

Clinical signs of thrombosis and atherosclerosis are unreliable and thus there is a compelling need for methods for early detection. Arterial thrombosis is a causative factor in unstable angina, acute myocardial infarction, sudden cardiac death, transient ischemic attacks, and stroke. Inaccurate diagnosis, ineffective therapeutic response, and restenosis following seemingly successful treatments, such as angioplasty, are all problems associated with acute arterial syndromes. Furthermore, emboli lodging in the cerebral as well as the pulmonary and peripheral vascular circulation are a major cause of morbidity and mortality. Unfortunately, all the existing techniques to localize thrombi have proven to have significant limitations and are inaccurate. Most of the problems associated with past methodologies could be solved by a small agent that could rapidly ($\leq 2$ hrs.) bind with high affinity to a component of thrombi, emboli, and a therosclerotic plaque.

There is a recognition in the art that plasminogen activators with greater specificity for fibrin are desired for the dissolution of intravascular clots, and one approach has been the preparation of chemically cross-linked or recombinant hybrid molecules. These have included: a cross-linked hybrid combining the fibrin-binding domain of plasminogen and the catalytic domain of urokinase (Robbins et al., *Biochemistry* 25:3603 (1986)); a hybrid linking the fibrin-binding A chain of plasminogen to the catalytic domain of tPA (Robbins et al., *Science* 222:4661 (1987)); a recombinant hybrid composed of the fibrin-binding domain of tPA and the low molecular weight form of scuPA (the catalytic site of urokinase) in a form that is resistant to plasminogen activator inhibitor-I (Nelles, L. et al., *J. Biol. Chem.* 262:10855 (1987)); and antibody-based molecules such as a hybrid between an anti-fibrin β chain mAb and tPA (Schnee, J. M., et al., *Proc. Natl. Acad. Sci. USA* 84:6904–6908 (1987)). Non-human monoclonal antibodies are foreign to a human patient and can induce a host vs. graft response.

Whereas current methods are sufficiently sensitive to detect pulmonary emboli, e.g., by angiography, there is no specific method for identification of the emboli. There thus exists in the art a long recognized need for a specific method that could be used repetitively in a subject that can better target imaging agents to fibrin-containing emboli. Moreover, since spontaneous release of thrombi in stenotic coronary vessels is believed to be a mechanism involved in unstable angina (Ambrose et al., *JACC* 13:1666–1671 (1989)), repetitive use of a fibrin-binding imaging agent to identify microthrombi would aid in monitoring the effects of administering anticoagulants (and vasodilators).

The identification and characterization of the sites of thrombosis, intravenous fibrin deposition or atherosclerosis are important for clinical diagnosis. In the case of early localized thrombosis, it is preferable to search for "hidden sites" in individuals who have not yet developed clinical symptoms. In individuals suffering from a disease or condition associated with thrombosis or intravascular fibrin, the capacity to identify the location and size of the involved sites and monitor changes following initiation of therapy is important for effective clinical treatment.

Whereas known techniques can provide some useful information, they result in an unacceptably high frequency of both false positive and false negative results, may be insensitive, require an unacceptable amount of handling and processing, or are accompanied by unacceptable side effects. Thus, there is a recognized need in the art for more direct, more sensitive and more specific methods for detecting and localizing sites of thrombosis, fibrin deposition or atherosclerotic plaque, particularly techniques that could be performed serially to assess the response to therapy over time.

SUMMARY OF THE INVENTION

The present invention is primarily directed toward novel fibrin-binding molecules which include fibrin-binding peptides derived from fibronectin. Such molecules have a number of utilities, such as for the diagnostic imaging of clots, thrombi, microthrombi, pulmonary emboli, atherosclerotic lesions or tumors, and the targeted delivery of therapeutic agents to thrombi, cancer cells and/or sites of certain bacterial infections. The fibrin-binding molecules of the present invention can also be used to treat, inter alia, a subject suffering from a disease or disorder involving abnormal fibrinolysis or fibrinogenesis. Thus, the present invention includes fibrin-binding molecules, diagnostic and pharmaceutical compositions comprising such molecules, methods for producing these molecules, DNA encoding such molecules, and methods of using such molecules and pharmaceutical compositions.

The fibrin-binding molecules of the present invention include at least one peptide essentially corresponding to one or both of the following portions of the natural fibronectin molecule. The first portion is that portion which includes the $^4$F1.$^5$F1 module pair of fibronectin but includes no more of the natural fibronectin molecule than the N-terminal 25.9 kDa proteolytic fragment. The second portion includes the $^{10}$F1.$^{11}$F1 module pair of fibronectin but includes no more of the natural fibronectin molecule than the C-terminal 11 kDa proteolytic fragment.

The fibrin-binding molecules may include, bound to the peptide, a diagnostic marker or a therapeutic agent. The diagnostic marker may be a detectable label for use in imaging of areas of the body to which the fibrin-binding molecules of the present invention may bind. The therapeutic agent may be a thrombolytic or fibrinolytic agent in order to lyse the clots which are bound by the fibrin-binding portions of the molecules. Alternatively, the therapeutic agent may be a cytotoxic agent for use, for example, when the cells which are bound by the fibrin-binding portion of the molecules are tumor cells.

The fibrin-binding molecules of the present invention may be formulated into pharmaceutical compositions with an appropriate pharmaceutically acceptable carrier.

Methods for making the fibrin-binding molecules of the present invention include recombinant DNA techniques, peptide synthesis or proteolytic cleavage from the intact fibronectin molecule. For the purpose of producing the molecules of the present invention by recombinant DNA techniques, a DNA molecule encoding the fibrin-binding molecule must first be obtained, which DNA molecule is also an embodiment of the present invention. Vectors containing such DNA and hosts transfected by such vectors and capable of expressing the fibrin-binding molecules of the present invention are also embodiments of the present invention.

A method for the production of the fibrin-binding molecules of the present invention by recombinant DNA techniques preferably comprises:

(a) culturing a host capable of expressing the peptide under culturing conditions, (b) expressing the peptide; and (c) recovering the peptide from the culture.

The process can additionally comprise: (d) purifying the peptide.

The present invention is also directed to a method of detecting a site of fibrin deposition, such as thrombosis, emboli, tumor, wounds, infection, or atherosclerotic plaque in an individual which comprises administering to the individual a diagnostically effective amount of a detectably labeled peptide as above, which substantially accumulates at the site and does not substantially accumulate at a site which does not have the thrombosis, fibrin deposition, or atherosclerotic plaque, and detecting the fibrin-binding peptide.

Also provided is a method for preventing or treating a cardiovascular, cerebrovascular or peripheral vascular disease by administering to a subject an effective amount of a peptide, either by itself or attached or bound to a fibrinolytic or thrombolytic agent or pharmaceutical composition as above.

Antibodies specific for a fibrin-binding domain of the molecules of the present invention are also an embodiment of the present invention. Such antibodies may be used to interfere with the binding of fibronectin to fibrin or for immunoassays for the fibrin-binding epitopes of fibronectin.

In yet another embodiment, the invention provides an immunoassay method for detecting the presence or measuring the concentration of a substance capable of binding to fibrin in a sample, comprising (a) contacting a sample suspected of containing the fibrin-binding substance with fibrin bound to a carrier under conditions which allow the substance to bind to the fibrin;

(b) contacting a binding partner specific for the fibrin-binding substance with the bound fibrin-binding substance under conditions which allow the binding partner to bind to the substance; and (c) measuring the binding partner bound or unbound to the carrier, thereby detecting or measuring the fibrin-binding substance.

An alternative embodiment is provided, wherein a competitive immunoassay method for detecting the presence or measuring the concentration of a substance capable of binding to fibrin in a sample, comprises (a) incubating a sample suspected of containing the fibrin-binding substance with:
  (i) a known fibrin-binding protein or peptide; and
  (ii) a fibrin-binding peptide bound to a carrier, under conditions which allow the substance to bind to the carrier-bound fibrin, wherein the binding of the substance will competitively inhibit the binding of the known fibrin-binding protein or peptide;

(b) contacting a binding partner specific for the known fibrin-binding peptide or protein with the bound fibrin-binding substance under conditions which allow the binding partner to bind to the substance; and (c) measuring the binding partner bound or unbound to the carrier, wherein a decrease in the amount of binding partner bound is directly related to the concentration of the substance in the sample, thereby detecting or measuring the fibrin-binding substance.

BRIEF DESCRIPTION OF THE DRAWINGS

FIG. 2 shows a representative selection of some of the known proteins that comprise mosaics of modules. Proteins (a)–(d) are associated with blood clotting/fibrinolysis; proteins (e)–(h) are associated with complement; proteins (i) and (j) are in the extracellular matrix; twitchin (k) is an intracellular protein associated with muscle; proteins (l) and (m) are cell adhesion molecules; proteins (n)–(q) are various cell-surface receptors. Individual modules are depicted by letters and different shapes. With the exception of twitchin, all the proteins shown are found on the cell surface and/or in extracellular spaces and are usually glycosylated. Most of the modules are stabilized by disulfide bridges although the third fibronectin module, F3, which appears in numerous proteins both inside and outside the cell, usually is not.

FIG. 4A is the standard specification for showing the peaks while FIG. 4B is set to show the centroid heights of the peaks. The number of shots averaged 47 and the laser energy was 2:186. Two picomoles of sample and 10 picomoles of β-lactoglobulin were used.

FIG. 5 presents the amino acid sequence (SEQ ID NO:1) of a human plasma fibronectin molecule and shows the localization of the fibrin-binding peptides within this sequence. Noted is the sequence of the N-terminal fibrin-binding domain that possesses a molecular mass of 25,873 Da as determined by laser desorption mass spectrometry. By amino acid sequence analysis, determination of the molecular mass, and analysis of the theoretical masses by the computer program General Protein Mass Analysis for Windows, it was determined that the N-terminal FBP commences at $Ser^{17}$ and terminates at $Gln^{246}$ (residues 17–246 of SEQ ID NO:1). Also indicated is the sequence of the 11 kDa C-terminal fibrin-binding fragment beginning at $Gln^{2123}$ (residues 2123–2232 of SEQ ID NO:1).

FIG. 6 presents the amino acid sequence of the entire 11 kDa C-terminal fibrin-binding peptide (residues 2123–2232 of SEQ ID NO:1).

FIG. 15 shows a schematic diagram of the pMA91 yeast/shuttle/expression vector. The BglII/BamHI fragment from pMB50 (see FIG. 15) is ligated between the Phosphoglycerate Kinase (PGK) promoter and terminator, which direct expression. Ampicillin resistance is used to select for positive *E. coli* clones and the leu2 gene for positive yeast transformants. Vector construction and expression for the $^1F1$ and $^1F1.^2F1$ type 1 modules are performed as described for the $^4F1.^5F1$. In the case of the $^{10}F1$ module the expression plasmid is constructed using the pSW6 vector with a galactose inducible promoter. The fibronectin DNA insert is ligated directly into the single BglII site of the pSW6 yeast expression vector, downstream and in phase with the α-factor leader sequence. Competent yeast cells (*Saccharomyces cerevesiae* MC2) were transformed with pSW6-$^{10}F1$ and selected by their ability to grow on leucine-minus medium.

FIG. 16 schematically illustrates the initial fusion protein product containing the fibronectin type 1 $^4F1.^5F1$ structural domain. The 60 residue signal leader sequence directs peptide secretion. It is separated from the fibronectin type 1 domain by Lys-Arg. The fusion product is cleaved at the C-terminal side of Arg by KEX2, a yeast cathepsin B-like protease, during secretion, leaving an authentic N-terminus.

FIG. 19 presents an alignment of human type 1 module sequences from modules 1–12 of fibronectin (residues 21–65, 66–109, 110–154, 155–199, 200–244, 277–311, 439–486, 487–529, 530–569, 2144–2188, 2189–2232, and 2233–2271, respectively, of SEQ ID NO:1), factor XII (SEQ ID NO:4) and tPA (SEQ ID NO:5). The sequences are aligned to maintain homologous positions for highly conserved residues in the secondary structure. Consensus features are displayed according to the following code: uppercase, invariant residues; y, tyrosine or phenylalanine; r, arginine or lysine; a, aromatics; t, turn forming or polar; p, exclusively polar; h, hydrophobic. Linker sequences between the last and first cysteine residues of consecutive modules are shown. The $^5$F1 and $^6$F1 modules are separated by a 37 amino acid residue sequence. $^6$F1 and $^7$F1 are separated by 2 type 2 modules. A total of 15 to 17 type 3 modules plus the IIICS sequence separate $^9$F1 and $^{10}$F1. The 93 amino acid residue sequence of $^4$F1.$^5$F1 is underlined. Filled circles underscore conserved regions of β-sheet, identified from NMR structures of $^4$F1, $^5$F1, $^7$F1 and t-PA-F1.

FIG. 26A represents the ELISA binding of the $^4$F1.$^5$F1 module pair to fibrin-coated plates. FIG. 26B shows the binding of the $^4$F1.$^5$F1 module pair to a fibrin-SEPHAROSE™ affinity matrix. FIG. 26C shows the elution profile of the $^1$F1.$^2$F1 module pair, employed as a negative control, from a fibrin-SEPHAROSE™ affinity matrix. In FIGS. 26B and 26C, the arrows denote change in buffer. Pooled fractions from the affinity chromatography matrices were analyzed by SDS-PAGE composed of a gradient of acrylamide monomer 5–20% (not shown). For the experiments of both FIGS. 26B and 26C, the lanes which included recombinant fibronectin modules before application to fibrin-SEPHAROSE™ and those with the unbound fraction to the fibrin-affinity matrices showed the presence of the recombinant fibronectin modules. However, while the lanes with the fractions obtained following warming the fibrin-SEPHAROSE™ to 22° C. and with the fractions eluted with 0.5M NaCl, 6M urea, showed the presence of module in the experiment of FIG. 26B, none was present in the experiment of FIG. 26C.

FIG. 27A is a graph showing the binding of increasing concentrations of fibronectin to fibrin-coated microtiter plates. FIG. 27B is a graph showing the competition of binding of fibronectin to fibrin by specified recombinant type 1 modules.

FIG. 28A is a graph showing the direct binding of increasing concentrations of biotinylated fibronectin to fibrin-coated microtiter wells. FIG. 28B shows the competitive inhibition of biotinylated fibronectin binding to fibrin by unlabeled intact fibronectin, the 25.9 kDa N-terminal proteolytic fragment and recombinant type 1 modules.

FIG. 29 is a graph showing the inhibition of the binding of biotinylated fibronectin to fibrin by a monoclonal antibody to the N-terminal domain of fibronectin and by the recombinant $^4$F1.$^5$F1.

FIGS. 30A and B are graphs showing the results of the image analysis and quantitation of the optical density of the autoradiograms from $^{35}$S-methionine labeled $^4$F1.$^5$F1 and $^{10}$F1-end, respectively. The relative amounts of protein represented by the radiolabel which eluted at 22° C. with 0.5M NaCl, 6M urea are displayed.

FIG. 31 is a graph showing the pharmacokinetics of $^{125}$I labeled and purified 11 kDa FBP which were injected into four rats (430–500 g). Following injection of 49.3 μCi (6.9×10$^7$ cpm)/0.36 ml/13.2 μg 11 kDa FBP/rat into the right femoral vein, plasma (0.1 ml) was withdrawn at various time points and TCA ppt. counts obtained with a 50 μl aliquot thereof. Counts were from 75–80% TCA precipitable, for each time point, indicating that no degradation of the $^{125}$I-11 kDa FBP occurred in the plasma.

DETAILED DESCRIPTION OF THE PREFERRED EMBODIMENTS

Figure 1:
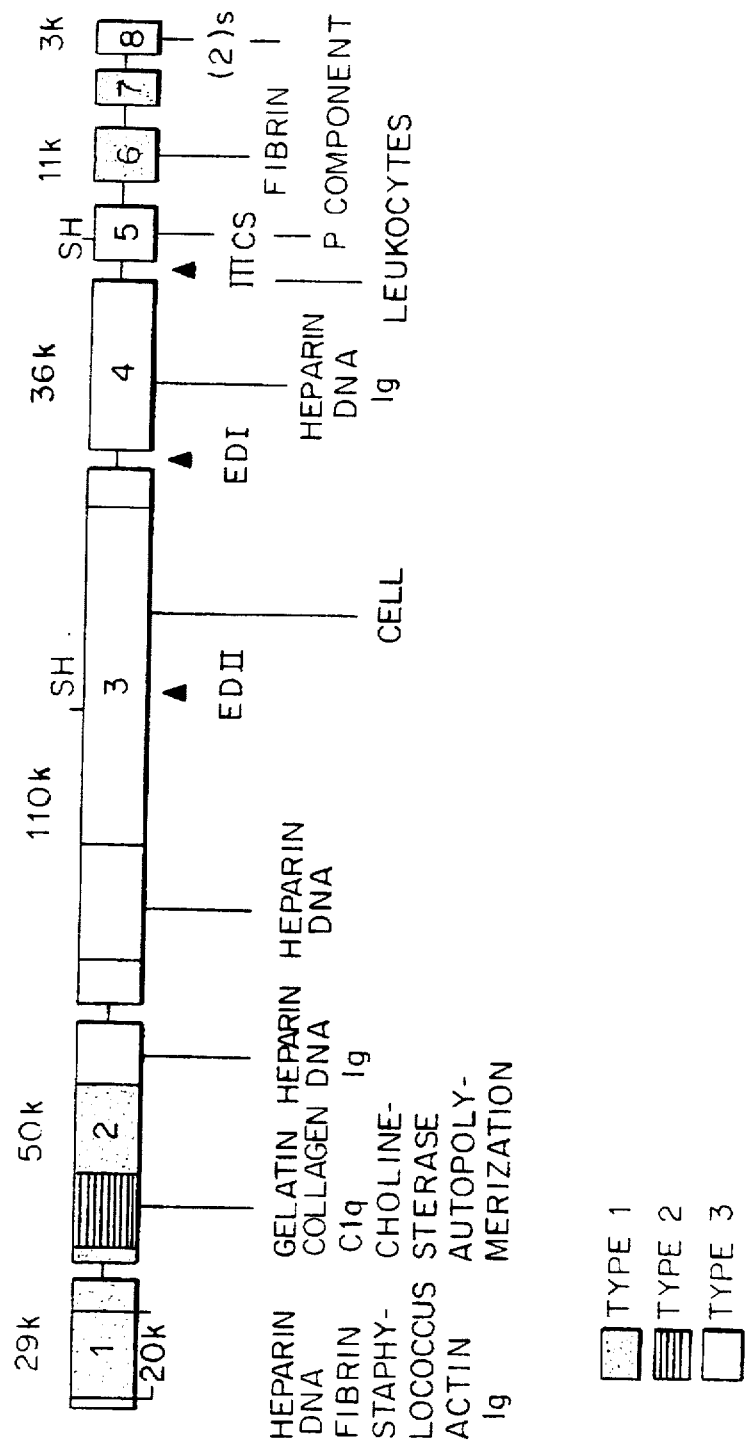
FIG. 1 presents a depiction of a three-dimensional model of the domain structure of human plasma fibronectin.

The present invention is directed to fibrin-binding peptides (FBPs) having fibrin-binding activity. These FBPs have utility in methods for detecting the presence of fibrin in a subject, for example, in the imaging of thrombi, intravascular fibrin, or atherosclerotic lesions in vivo. The peptides of the present invention also have utility for the delivery of thrombolytic or fibrinolytic agents to fibrin-containing sites, for example, in the treatment of vascular disorders or occlusions, wounds or trauma, cancer, bacterial infection, pulmonary embolisms, and thrombi. FBPs are thus also useful for treating clotting disorders, e.g. inter alia, by either preventing tPA-mediated thrombolysis or dysregulated fibrinogenesis.

Some of the advantages of the peptides of the present invention (as therapeutic agents or as imaging or targeting devices) over anti-fibrin antibodies or "fibrin-binding peptides" of the related art, include, inter alia, (1) faster clearance relative to the entire human protein, a larger fibrin-binding peptide and/or a murine, human or chimeric antibody, because of relatively much shorter length, thereby providing a smaller signal to noise ratio in diagnostic applications; (2) faster diffusion, improved binding because of higher affinity, and slower dissociation from fibrin, due to the use of a shorter but active sequence; and (3) constant and defined binding affinity for fibrin, whereas different antibodies vary in their affinity for fibrin.

Anti-FBP antibodies of the present invention are also useful for biological assays of fibrin binding, and as in vitro or in vivo reagents to detect fibronectin or fibrin to which FBPs are bound. Such antibodies can be employed in any other tests requiring the localization of the intact fibronectin molecule or a fibrin-binding portion thereof. Antibodies of the present invention can also be used as inhibitors to confirm the specificity of fibrin-binding and for quantitative analysis, such as in ELISA.

FBPs can also be used in immunoassays, most preferably ELISAs, for the detection of unknown fibrin-binding substances. In a preferred embodiment, the unknown fibrin-binding substance is tested for its ability to compete with the binding of the peptide of the present invention to fibrin.

FIBRIN-BINDING PEPTIDES (FBPs).

A fibrin-binding peptide can refer to any subset of a fibronectin molecule that has the capability of binding to fibrin. A peptide fragment according to the present invention can be prepared by proteolytic digestion of the intact fibronectin molecule or a fragment thereof, by chemical peptide synthesis methods well-known in the art, by recombinant DNA methods discussed in more detail below, and/or by any other method capable of producing a peptide corresponding to a fibrin-binding peptide of fibronectin and having the required conformation for fibrin-binding activity. While the repeating modules of fibronectin are remarkably similar, it has surprisingly been found that the N-terminal fibrin-binding region of fibronectin resides only in the $^4$F1.$^5$F1 module pair and the C-terminal fibrin-binding region of fibronectin resides only in the $^{10}$F1.$^{11}$F1 module pair.

With respect to the $^4$F1.$^5$F1 module pair, the precise beginning and ending amino acid residues of the smallest fragment retaining the fibrin-binding activity has not yet been determined. However, the first fully conserved residue of the $^4$F1 module is Cys$^{155}$ of SEQ ID NO:1 and the last fully conserved residue of $^5$F1 is Cys$^{239}$ of SEQ ID NO:1 (see FIG. 19). Thus, it is presumed that the smallest fragment to retain fibrin-binding activity is residues 155–239 of SEQ ID NO:1. As will be described in greater detail hereinbelow, however, it can readily be determined by routine experimentation if one or more additional residues may be removed from either end of this module pair and still allow the module pair to retain its fibrin-binding activity. Thus, for the purpose of the present specification and claims, the term "$^4$F1.$^5$F1 module pair" is intended to include the smallest portion of the 93 amino acid module pair of FIG. 21 (residues 152–244 of SEQ ID NO:1) which retains fibrin-binding activity.

Figure 21:
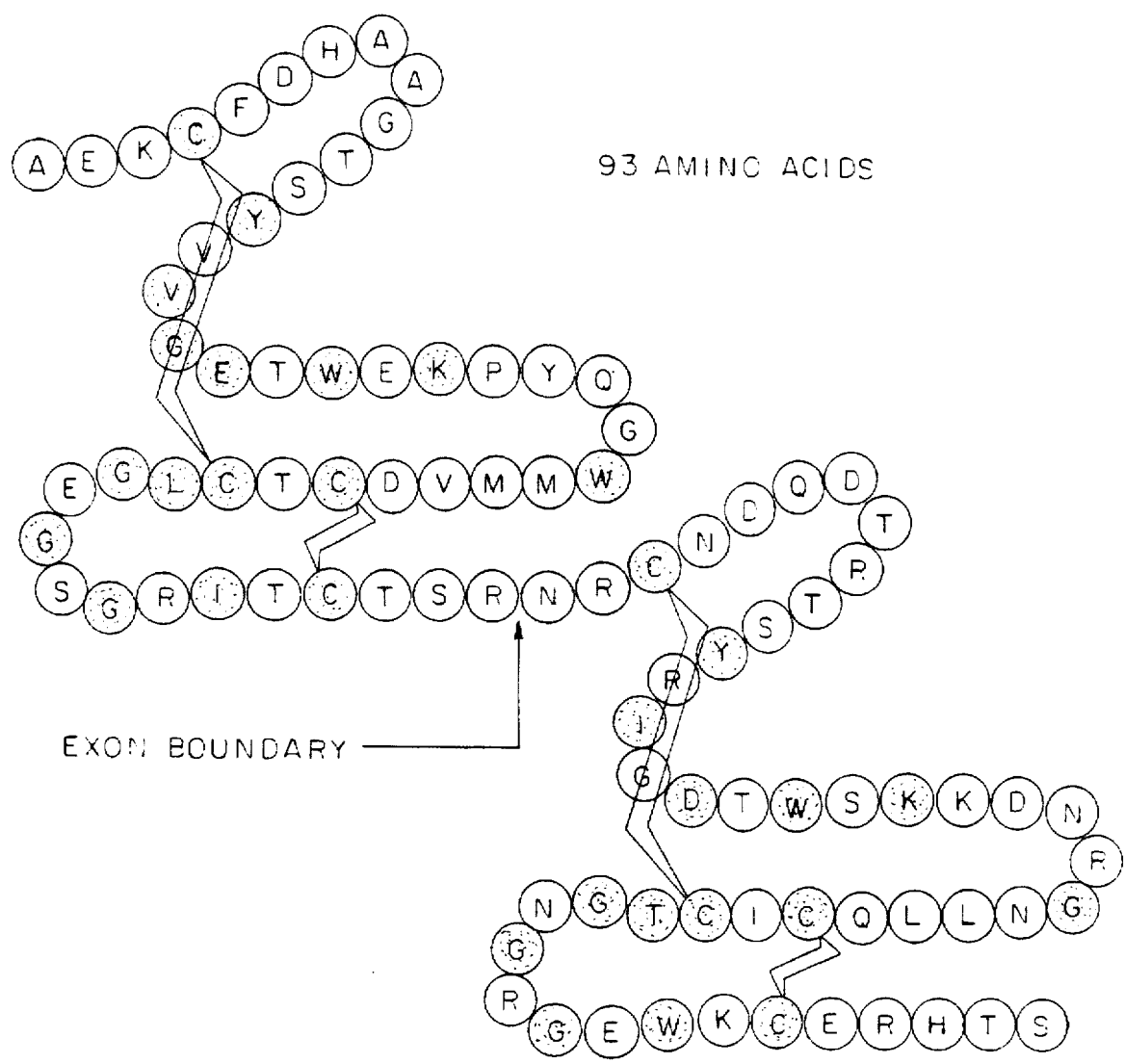
FIG. 21 shows a model of the secondary structure of the type 1 module pair including the 4th and 5th modules (fibronectin module pair $^4$F1.$^5$F1) from human fibronectin. (residues 152–244 of SEQ ID NO:1). Shaded residues are highly conserved in aligned sequences or show predominantly conservative replacements. The module pair includes 93 amino acids. The exon boundary is shown.

In a preferred embodiment, the peptide of the present invention has the sequence of residues 152–244 of SEQ ID NO:1 (see FIG. 21).

While the preferred FBP of the present invention has the smallest structure which retains its fibrin-binding properties, the present invention also comprehends larger fragments of fibronectin which include the $^4$F1.$^5$F1 module pair and yet are smaller than any such fragment known to the prior art. The smallest proteolytic fragment found by the present inventors to include the N-terminal fibrin-binding properties of fibronectin is the 25.9 kDa N terminal fragment which has been shown to include residues 17–246 of SEQ ID NO:1. Thus, the present invention is intended to comprehend this 25.9 kDa fragment as well as any fragment smaller than the 25.9 kDa fragment which includes the $^4$F1.$^5$F1 module pair and thus will also retain fibrin-binding activity.

With respect to the $^{10}$F1.$^{11}$F1 module pair, the precise beginning and ending amino acid residues of the smallest fragment retaining the fibrin-binding activity has not yet been determined. However, the first fully conserved residue of the $^{10}$F1 module is Cys$^{2144}$ of SEQ ID NO:1 and the last fully conserved residue of $^{11}$F1 is Cys$^{2226}$ of SEQ ID NO:1 (see FIG. 19). Thus, it is presumed that the smallest fragment to retain fibrin-binding activity is residues 2144–2226 of SEQ ID NO:1. These numbers correspond to the sequence as set forth in SEQ ID NO:1, which is a Fn monomer that does not contain extra domains due to mRNA splicing. It should be understood that the corresponding numbers will be shifted if such extra domains are present. As will be described in greater detail hereinbelow, however, it can readily be determined by routine experimentation if one or more additional residues may be removed from either end of this module pair and still allow the module pair to retain its fibrin-binding activity. Thus, for the purpose of the present specification and claims, the term "$^{10}$F1.$^{11}$F1 module pair" is intended to include the smallest portion of the 90 amino acid module pair of FIGS. 23–24 (residues 2141–2230 of SEQ ID NO:1) which retains fibrin-binding activity.

Figure 23:
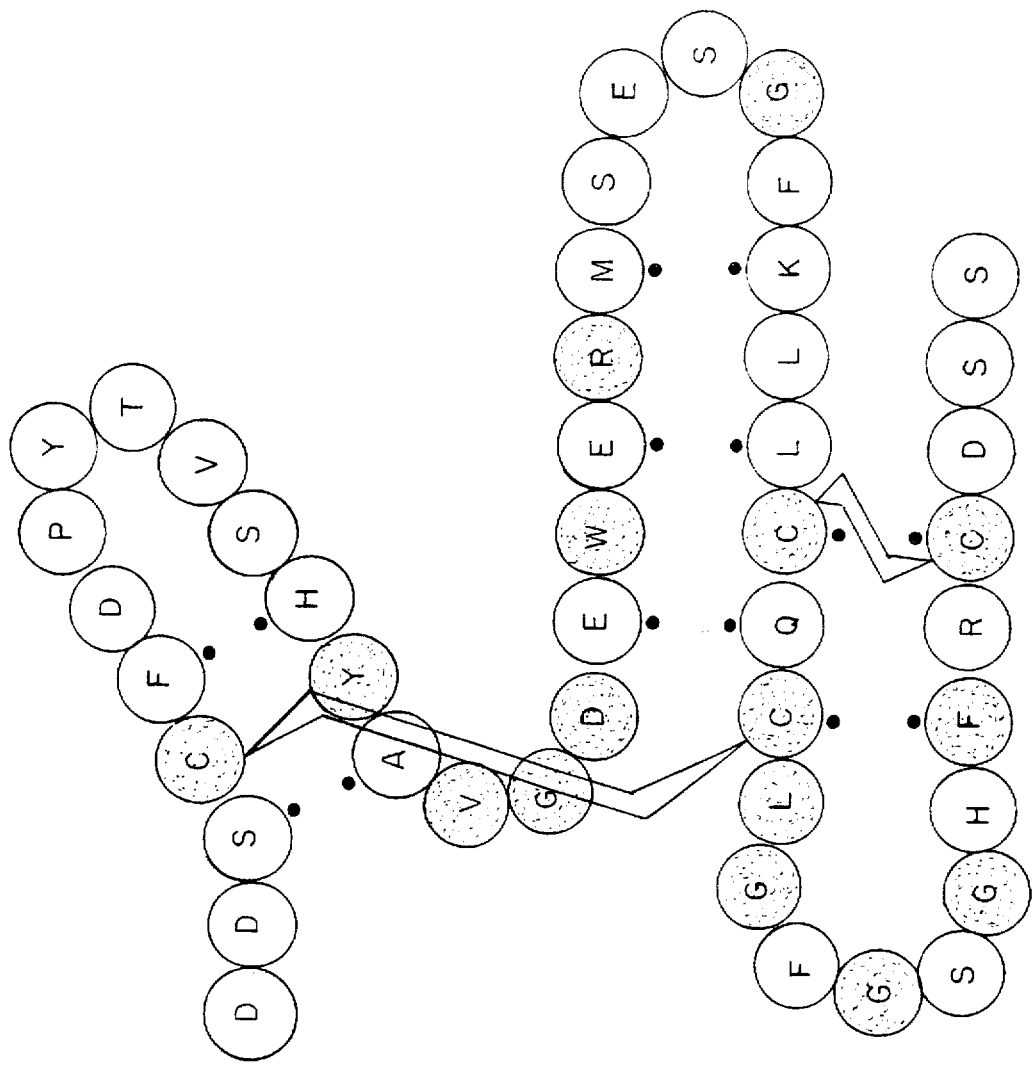
FIG. 23 shows a model of the secondary structure of the 46 amino acid tenth type 1 module from human fibronectin (fibronectin module $^{10}$F1) (residues 2141–2186 of SEQ ID NO:1). Shaded residue are highly conserved in aligned sequences or show predominantly conservative replacements.
Figure 24:
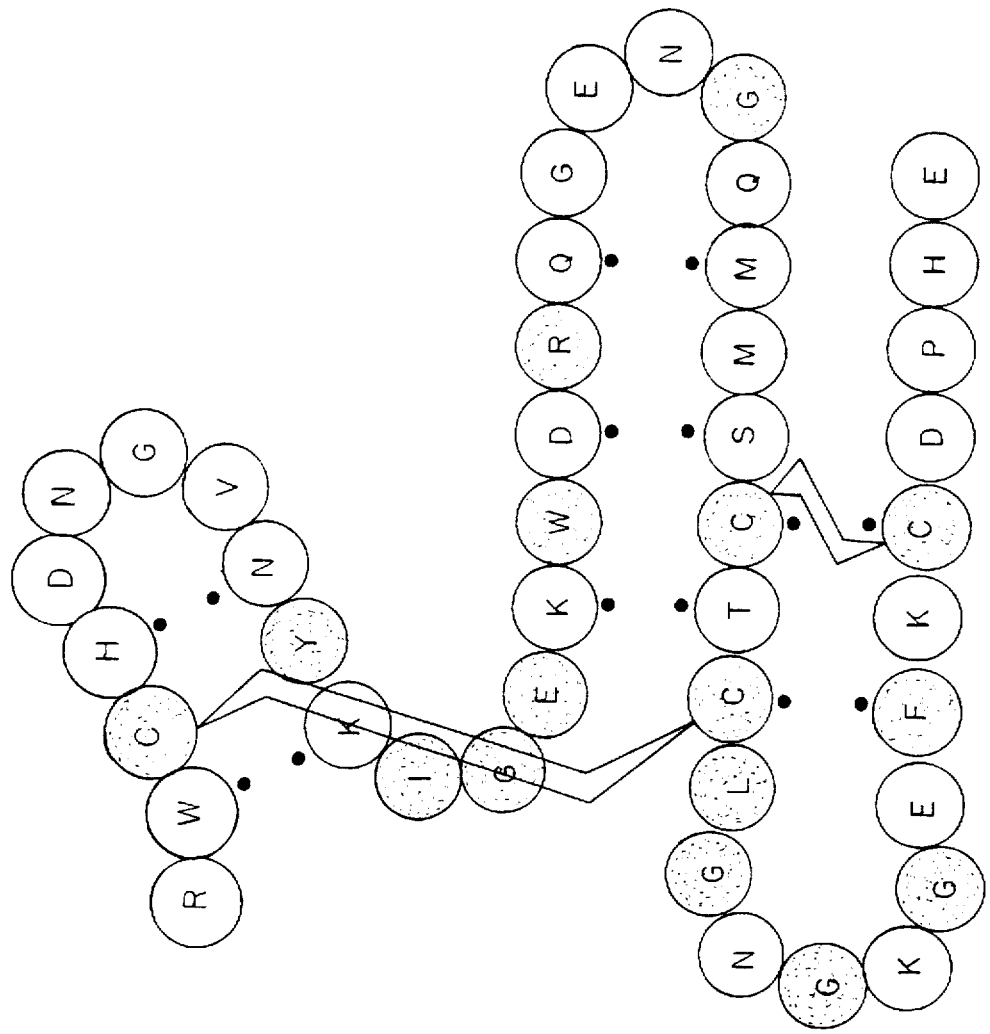
FIG. 24 shows a model of the secondary structure of the 44 amino acid eleventh type 1 module from human fibronectin (human fibronectin module $^{11}$F1) (residues 2187–2230 of SEQ ID NO:1). Shaded residues are highly conserved in aligned sequences or show predominantly conservative replacements.

In a preferred embodiment, the peptide of the present invention has the sequence of residues 2141–2230 of SEQ ID NO:1 (see FIGS. 23 and 24).

While the preferred FBP of the present invention has the smallest structure which retains its fibrin-binding properties, the present invention also comprehends larger fragments of fibronectin which include the $^{10}$F1.$^{11}$F1 module pair and yet are smaller than any such fragment known to the prior art. The smallest proteolytic fragment found by the present inventors to include the C-terminal fibrin-binding properties of fibronectin is the 11 kDa N terminal fragment which has been shown to include residues 2123–2232 of SEQ ID NO:1. Thus, the present invention is intended to comprehend this 11 kDa fragment as well as any fragment smaller than the 11 kDa fragment which includes the $^{10}$F1.$^{11}$F1 module pair and thus will also retain fibrin-binding activity.

A fibrin-binding peptide (FBP) of the present invention also includes a variant wherein at least one amino acid residue in the polypeptide has been conservatively replaced by a different amino acid. An amino acid or nucleic acid sequence of a fibrin-binding polypeptide of the present invention is said to "essentially correspond" to another amino acid or nucleic acid sequence respectively, if the sequence of amino acids or nucleic acid in both molecules provides polypeptides having biological activity that is essentially similar, qualitatively or quantitatively, to the corresponding fragment of at least one fibrin-binding functional domain. Such "essentially corresponding" fibrin-binding sequences include conservative amino acid or nucleotide substitutions, or degenerate nucleotide codon substitutions wherein individual amino acid or nucleotide substitutions are well known in the art.

Accordingly, fibrin-binding polypeptides of the present invention, or nucleic acid encoding therefor, include a finite set of essentially corresponding sequences as substitution peptides or polynucleotides which can be routinely obtained by one of ordinary skill in the art, without undue experimentation, based on the teachings and guidance presented herein. For a detailed description of protein chemistry and structure, see Schulz, G. E. et al., *Principles of Protein Structure*, Springer-Verlag, New York, 1978, and Creighton, T. E., *Proteins: Structure and Molecular Properties*, W. H. Freeman & Co., San Francisco, 1983, which are hereby incorporated by reference. For a presentation of nucleotide sequence substitutions, such as codon preferences, see Ausubel et al, eds, CURRENT PROTOCOLS IN MOLECULAR BIOLOGY, Greene Publishing Assoc., New York, N.Y. (1987, 1988, 1989, 1990, 1991, 1992, 1993, 1994) at §§ A.1.1–A.1.24, and Sambrook et al, *Molecular Cloning: A Laboratory Manual*, Second Edition, Cold Spring Harbor Press, Cold Spring Harbor, N.Y. (1989), at Appendices C and D.

Thus, one of ordinary skill in the art, given the teachings and guidance presented in the present specification, will know how to substitute other amino acid residues in other positions of the fibrin-binding sequence to obtain a fibrin-binding peptide.

AMINO ACID SUBSTITUTIONS OF NATIVE FIBRIN-BINDING REGIONS FOR A FIBRIN-BINDING POLYPEPTIDE.

Conservative substitutions of a fibrin-binding polypeptide of the present invention include variants wherein at least one amino acid residue in the polypeptide has been conservatively replaced by a different amino acid.

Such substitutions preferably are made in accordance with the following list as presented in Table I, which substitutions can be determined by routine experimentation to provide modified structural and functional properties of a synthesized or recombinant polypeptide molecule, while maintaining FBP binding biological activity, as determined by known FBP activity assays. In the context of the present invention, the term "essentially corresponding to" includes such substitutions.

TABLE I (A)

| Original Residue | Exemplary Substitution |
| --- | --- |
| Ala | Gly;Ser |
| Arg | Lys |
| Asn | Gln;His |
| Asp | Glu |
| Cys | Ser |
| Gln | Asn |
| Glu | Asp |
| Gly | Ala;Pro |
| His | Asn;Gln |

TABLE I (A)-continued

| Original Residue | Exemplary Substitution |
| --- | --- |
| Ile | Leu;Val |
| Leu | Ile;Val |
| Lys | Arg;Gln;Glu |
| Met | Leu;Tyr;Ile |
| Phe | Met;Leu;Tyr |
| Ser | Thr |
| Thr | Ser |
| Trp | Tyr |
| Tyr | Trp;Phe |
| Val | Ile;Leu |

Non-limiting examples of specific substitutions of FBPs of the present invention can include the following.

TABLE I(B)

(1): FBP ESSENTIALLY CORRESPONDING TO THE $^4$F1.$^5$F1 MODULE PAIR OF FIBRONECTIN (152-244 of SEQ ID NO:1)
Ala-Glu-Lys-Cys-Phe-Asp-His-Ala-Ala-Gly-Thr-Ser-Tyr-Val-Val-Gly-
Gly-Asp-Arg   Met Glu Asn Gly Gly Ala Ser Thr Trp Ile Ile Ala
Ser       Gln    Leu       Gln Ser Ser Pro Phe Leu Leu Pro
          Glu    Tyr
Glu-Lys-Pro-Tyr-Gln-Gly-Trp-Met-Met-Val-Asp-Cys-Thr-Cys-Leu-Gly-
Asp Arg   Trp Asn Ala Tyr Leu Leu Ile Glu  Ser         Ile Ala
    Gln   Phe                     Tyr Tyr Leu Lys     Val
    Glu                               Ile Ile
Glu-Gly-Ser-Gly-Arg-Ile-Thr-Cys-Thr-Ser-Arg-Cys-Asn-Asp-Gln-Asp-
Asp Ala Thr Ala Lys Leu Ser    Ser Thr Lys    Gln Glu Asn Glu
                           Val                    His
Thr-Arg-Thr-Ser-Tyr-Arg-Ile-Gly-Asp-Thr-Trp-Ser-Lys-Lys-Asp-Asn-
Ser Lys Ser Thr Trp Lys Leu Ala Glu Ser Tyr Thr Arg Arg Glu Gln
            Phe         Val Pro         Gln Gln         His
                                            Glu Glu
Arg-Gly-Asn-Leu-Leu-Gln-Cys-Ile-Cys-Thr-Gly-Asn-Gly-Arg-Gly-Glu-
Lys Ala Gln Ile Ile Asn      Leu     Ser Ala Gln Ala Lys Ala Asp
        Pro His Val Val      Val     Pro His Pro     Pro
Trp-Lys-Cys-Glu-Arg-His-Thr-Ser
Tyr Arg       Asn Lys Asn Ser Thr
    Gln       Gln
    Glu (2): FBP ESSENTIALLY CORRESPONDING TO $^{10}$F1.$^{11}$F1 MODULE PAIR OF FIBRONECTIN (2141-2230 OF SEQ ID NO:1)

Asp-Asp-Ser-Cys-Phe-Asp-Pro-Tyr-Thr-Val-Ser-His-Tyr-Ala-Val-Gly-
Glu Glu Thr   Met Glu    Trp Ser Ile Thr Asn Trp Gly Ile Ala
              Leu        Phe Leu    Gln Phe Ser Leu Pro
              Tyr
Asp-Glu-Trp-Glu-Arg-Met-Ser-Glu-Ser-Gly-Phe-Lys-Leu-Leu-Cys-Gln-
Glu Asp Tyr Asp Lys Leu Thr Asp Thr Ala Met Arg Ile Ile        Asn
                Tyr                Pro Leu Gln Val Val
                Ile                    Tyr Glu
Cys-Leu-Gly-Phe-Gly-Ser-Gly-His-Phe-Arg-Cys-Asp-Ser-Ser-Arg-Trp-
        Ile Ala Met Ala Thr Ala Asn Met Lys Glu Thr Thr Lys Tyr
        Val Pro Leu Pro        Pro Gln Leu
                    Tyr                         Tyr
Cys-His-Asp-Asn-Gly-Val-Asn-Tyr-Lys-Ile-Gly-Glu-Lys-Trp-Asp-Arg-
        Asn Glu Gln Ala Ile Gln Trp Arg Leu Ala Asp Arg Tyr Glu Lys
        Gln        His Pro Leu His Phe Gln Val Pro     Gln
                                        Glu            Glu
Gln-Gly-Glu-Asn-Gly-Gln-Met-Met-Ser-Cys-Thr-Cys-Leu-Gly-Asn-Gly-
Asn Ala Asp Gln Ala Asn Leu Leu Thr    Ser    Ile Ala Gln
        Pro      His     Tyr Tyr            Val His Ala
                         Ile Ile
Lys-Gly-Glu-Phe-Lys-Cys-Asp-Pro-His-Glu
Arg Ala Asp Met Arg    Glu        Asn Asp
Gln         Leu Gln              Gln
Glu         Tyr Glu

Accordingly, based on the above example of specific substitutions, alternative substitutions can be made by routine experimentation, to provide alternative FBPs of the present invention, e.g., by making one or more conservative substitutions. Preferably, even such conservative substitutions should be in the non-conserved portions of the modules, as shown in FIG. 19. Thus, a residue or residue type which is conserved in all F1 modules should not be changed from the conserved residue or residue type. It would be expected that any such substitutions would retain fibrin-binding activity, which activity can be checked with routine experimentation, as will be described below.

Alternatively, another group of substitutions of FBPs of the present invention are those in which at least one amino acid residue in the protein molecule has been removed and a different residue inserted in its place according to the following Table II. The types of substitutions which can be made in the protein or peptide molecule of the present invention can be based on analysis of the frequencies of amino acid changes between a homologous protein of different species. Based on such an analysis, alternative conservative substitutions are defined herein as exchanges within one of the following five groups:

TABLE II

| | |
|---|---|
| 1. | Small aliphatic, nonpolar or slightly polar residues: Ala, Ser, Thr (Pro, Gly); |
| 2. | Polar, negatively charged residues and their amides: Asp, Asn, Glu, Gln; |
| 3. | Polar, positively charged residues: His, Arg, Lys; |
| 4. | Large aliphatic, nonpolar residues: Met, Leu, Ile, Val (Cys); and |
| 5. | Large aromatic residues: Phe, Tyr, Trp. |

The three amino acid residues in parentheses above have special roles in protein architecture. Gly is the only residue lacking any side chain and thus imparts flexibility to the chain. This, however, tends to promote the formation of secondary structure other than α-helical. Pro, because of its unusual geometry, tightly constrains the chain. It generally tends to promote β-turn-like structures. In some cases Cys can be capable of participating in disulfide bond formation which is important in protein folding. Note that Schulz et al. would merge Groups 1 and 2 above. Note also that Tyr, because of its hydrogen bonding potential, has significant kinship with Ser, and Thr, etc. Knowledge of the secondary structure (FIGS. 21, 23 and 24) and of the tertiary structure (FIG. 18) will assist those of ordinary skill in the art in determining which such substitutions would not be expected to affect the binding capability of the peptide. Again, however, changes from the conserved residues or residue types noted in FIG. 19 should be avoided.

Conservative amino acid substitutions, included in the term "essentially corresponding", according to the present invention, e.g., as presented above, are well known in the art and would be expected to maintain the binding properties of the polypeptide after amino acid substitution. Most deletions and insertions, and substitutions according to the present invention are those which do not produce radical changes in the characteristics of the protein or peptide molecule. "Characteristics" is defined in a non-inclusive manner to define both changes in secondary structure, e.g., α-helix or β-sheet, as well as changes in physiological activity, e.g., in receptor binding assays.

However, when the exact effect of the substitution, deletion, or insertion is to be confirmed, one skilled in the art will appreciate that the effect of the substitution or substitutions will be evaluated by routine screening assays, such as protein blotting, driver protein blotting, immunoassays, bioassays, etc., to confirm biological activity, such as, but not limited to, fibrin binding.

The present invention is directed not only to fibrin-binding peptides having a sequence corresponding or essentially corresponding to that of the fibrin-binding domains of fibronectin, but also to functional derivatives thereof.

By "functional derivative" is meant a derivative which retains at least a portion of the fibrin-binding function of the peptide which permits its utility in accordance with the present invention.

A "functional derivative" of the fibrin-binding peptide may contain additional chemical moieties not normally a part of the peptide. Covalent and/or non-covalent modifications of the chemical derivativitized peptide are also included within the scope of this invention. Such modifications can be introduced into the molecule by reacting targeted amino acid residues of the peptide with an organic derivatizing agent that is capable of reacting with selected side chains of the residues or terminal amino groups.

Covalent modifications of the fibrin-binding peptide of the present invention are included within the scope of the functional derivatives which are part of the present invention. Such modifications can be introduced into the molecule by reacting targeted amino acid residues of the FBP with an organic derivatizing agent that is capable of reacting with selected side chains or N-terminal residues of the FBP. The resulting covalent derivatives are useful in programs directed at identifying residues important for biological activity. The specific reactions and techniques described below are not intended to be limiting, but exemplify well-known means for chemically modifying peptides.

Derivatization with bifunctional agents is useful for crosslinking the fibrin-binding peptide to a water-insoluble support matrix or surface, or to reactive water-insoluble matrices such as cyanogen bromide-activated carbohydrates, dextrans and/or their reactive substrates, e.g., described in U.S. Pat. Nos. 3,969,287; 3,691,016; 4,195,128; 4,247,642; 4,229,537; and 4,330,440 and employed for protein immobilization.

Amino acid sequence insertions include amino and/or carboxyl-terminal fusions of from one residue to polypeptides of essentially unrestricted length. An example of a terminal insertion includes a fusion of a signal sequence, whether heterologous or homologous to the host cell, to the N-terminus of the fibrin-binding peptide to facilitate secretion from recombinant hosts.

Most deletions and insertions, and substitutions of FBPs according to the present invention are those which maintain or improve the fibrin-binding characteristics of the peptide molecule. However, when it is difficult to predict the exact effect of the substitution, deletion, or insertion in advance of doing so, one skilled in the art will appreciate that the effect will be evaluated by routine screening assays. For example, a variant made by site-specific mutagenesis of the peptide molecule-encoding nucleic acid and expression of the variant FBP in cell culture or, alternatively, by chemical synthesis, can be tested for binding by affinity chromatography using a fibrin-SEPHAROSE™ column (e.g., as described herein). The activity of the cell lysate or purified peptide variant can be screened in a suitable screening assay for the desired characteristic, for example fibrin binding in any of the several binding assays disclosed herein, e.g., protein blotting, affinity chromatography, ELISA, RIA, preformed or forming fibrin clot assay, or any other assay developed to test fibrin-binding capability (in vitro and in vivo).

Modifications of peptide properties, such as redox or thermal stability, hydrophobicity, susceptibility to proteolytic degradation or the tendency to aggregate with carriers or into multimers, are assayed by methods well known to the ordinarily skilled artisan.

Also included in the scope of the invention are salts of the fibrin-binding peptides of the invention. As used herein, the term "salts" refers to both salts of carboxyl groups and acid addition salts of amino groups of the protein or peptide molecule.

Amino acid sequence variants of the fibrin-binding peptide can also be prepared by mutations in the DNA. Such variants include, for example, deletions from, or insertions or substitutions of, residues within the amino acid sequence. Any combination of deletion, insertion, and substitution can also be made to arrive at expressing and producing the final peptide construct, provided that the final peptide construct possesses some fibrin-binding activity. Preferably improved fibrin-binding activity is found over that of the non-variant peptide. Obviously, the mutations that will be made in the DNA encoding the variant must not place the sequence out of reading frame and preferably will not create complementary regions that could produce secondary MRNA structure (see, e.g., EP Patent Application Publication No. 75,444, Ausubel, supra; Sambrook, supra.

At the genetic level, these variants ordinarily are prepared by site-directed mutagenesis of nucleotides in the DNA encoding the fibrin-binding peptide, thereby producing DNA encoding the variant, and thereafter synthesizing the DNA and expressing the protein in recombinant cell culture. The variants typically exhibit the same qualitative biological activity as the naturally occurring analogue. Ausubel, supra; Sambrook. supra.

DETERMINATION OF FBP STRUCTURAL AND PHYSICAL CHARACTERISTICS.

The present inventors have discovered that the $^4$F1.$^5$F1 and the $^{10}$F1.$^{11}$F1 module pairs of fibronectin prepared either by proteolytic cleavage of fibronectin or by genetic engineering (e.g., as described herein), possess substantial affinity for binding to fibrin, such affinity being equal to or greater than that of any previously known fibrin-binding peptide derived from, or corresponding to, fibronectin. This increased affinity is a key advantage and is of particular importance to the variety of uses included in the present invention. It is noteworthy that peptides of the present invention have higher affinity for fibrin than do high-affinity plasminogen activator preparations (Husain, S. S. et al., Proc. Natl. Acad. Sci. USA 78:4265–4269 (1981)). This can be seen from the fact that the tPA preparation of Husain et al. were eluted from solid phase fibrin with 0.2 mM arginine, whereas 1.0M arginine was required to only partially (25%) elute the 11 kDa peptide of the present invention from such a matrix, indicating significantly higher affinity for fibrin. The requirement for denaturing conditions (e.g., urea) for disruption of the binding between the peptide of the present invention and fibrin suggests that the interaction is hydrophobic. A fibrin-binding peptide having such high affinity is most particularly advantageous due to its rapid association with fibrin and lower likelihood of dissociation, which, in vivo, translates into more rapid delivery, longer half-life, and lower signal to noise background.

Knowledge of the three-dimensional structures of proteins is crucial in understanding how they function. The three-dimensional structures of more than 400 proteins are currently available in the protein structure database (in contrast to around 200,000 known protein and peptide sequences in sequence databases, e.g., Genbank, Chemical Abstracts, etc.). Analysis of these structures shows that they fall into recognizable classes or motifs. It is possible to model the three-dimensional structure of protein based on homology to a related protein of known structure. Examples are known where two proteins that have relatively low sequence homology, are found to have almost identical three dimensional structure.

Database analysis has revealed that a particular class of proteins, termed "modular" or "mosaic" proteins (Doolittle, Trends Biochem. Sci. 10:233–237 (1985); Pathy, Cell 41:657–663 (1985)), consist of a number of different types of repeated sequences represented by different shaped boxes (FIG. 2; Baron, M. et al. Trends Biochem. Sci. 16:13–17 1991). These sequence repeats are generally between 30 and 100 amino acids long and can be divided into different classes. Members of the same class of repeat have almost certainly evolved from a common ancestral gene sequence. The sequences of all the members of a particular class are not identical but are related in that certain key residues are conserved. These key residues are known as the "consensus sequence".

Both fibronectin and tPA are modular proteins composed of several such consensus sequences. Fibronectin consists largely of three types of modules (F1, F2 and F3 in FIG. 2). The diverse biological roles of fibronectin are attributable to the structural features of these modules (see, for review, Ruoslahti, supra; Hynes et al., supra ). One of these modules, called the type 1 repeat module of F1, has a specific placement of cysteine residues, that, upon disulfide bond formation, results in "fingerlike" domains.

There are 12 copies of the type 1 module (F1) in fibronectin. This module also appears in tPA and has fibrin-binding activity (Pennica et al., Nature 301:214–221 (1983); Bennet et al., J. Biol. Chem. 266:5191–5201 (1991)) and in the blood clotting protein, factor XII (McMullen, et al., J. Biol. Chem. 260:5328–5341 (1985)). These type 1 modules do not have identical sequences but are characterized by a "consensus sequence" or hydrophobic core consisting of a small number of highly conserved residues. These residues include four invariant cysteines, some highly conserved hydrophobic residues; tyrosines, valines, arginines, tryptophans, leucines, isoleucines phenylalanines, alanines, glycines and a lysine or arginine residue (FIG. 19). All of the type 1 sequences contain the majority of the "consensus sequence" or hydrophobic core sequence and thus can have similar three dimensional shapes (see Williams et al, Biochemistry 32:7388–7395 (1993) and Williams et al, J. Mol. Biol. 235:1302–11 (1994)). The present invention includes fibrin-binding peptides from type 1 repeat modules, such as the 4th, 5th, 10th, or 11th type repeat of fibronectin or any combination thereof, preferably the $^4$F1.$^5$F1 and the $^{10}$F1.$^{11}$F1 module pairs.

In recent years it has become possible to determine the structures of proteins of limited molecular weights by nuclear magnetic resonance (NMR). The technique only requires a concentrated solution of pure protein. No crystals or isomorphous derivatives are needed. The structures of a number proteins have been determined in the present inventors' laboratory by this method. The details of NMR structure determination are well-known in the art (Wuthrich, NMR of Proteins and Nucleic Acids, Wiley, N.Y., 1986; Wuthrich. K. Science 243:45–50 (1989); Clore et al., Crit. Rev. Bioch. Molec. Biol. 24:479–564 (1989); Cooke et al. Bioassays 8:52–56 (1988), which references are hereby incorporated by reference).

In applying this approach, a variety of $^1$H NMR 2D data sets are collected. These are of two main types: COSY (Correlated Spectroscopy) identifies proton resonances that are linked by chemical bonds. These spectra provide information on protons that are linked by three or less covalent bonds. NOESY (nuclear Overhauser enhancement spectroscopy) identifies protons which are close in space (less than 0.5 nm). Following assignment of the complete spin system, the secondary structure is defined by NOESY. Cross peaks (nuclear Overhauser effects or NOE's) are found between residues that are adjacent in the primary sequence of the peptide and can be seen for protons less than 0.5 nm apart. The data gathered from sequential NOE's combined with amide proton coupling constants and NOE's from non-adjacent amino acids, that are adjacent to the secondary structure, are used to characterize the secondary structure of the polypeptides. Aside from predicting secondary structure, NOE's indicate the distance that protons are in space in both the primary amino acid sequence and the secondary structures. Tertiary structure predictions are determined, after all the data are considered, by a "best fit" extrapolation.

Types of amino acids are first identified using through-bond connectivities. The second step is to assign specific amino acids using through-space connectivities to neighboring residues, together with the known amino acid sequence. Structural information is then tabulated and is of three main kinds: The NOE identifies pairs of protons which are close in space, coupling constants give information on dihedral angles and slowly exchanging amide protons give information on the position of hydrogen bonds. The restraints are used to compute the structure using a distance geometry type of calculation followed by refinement using restrained molecular dynamics. The output of these computer programs is a family of structures which are compatible with the experimental data (i.e. the set of pairwise <0.5 nm distance restraints). The better that the structure is defined by the data, the better the family of structures can be superimposed, i.e., the better the resolution of the structure. In the better defined structures using NMR, the position of much of the backbone (i.e. the amide, $\alpha C$ and carbonyl atoms), and the side chains of those amino acids that lie buried in the core of the molecule, can be defined as clearly as in structures obtained by crystallography. The side chains of amino acid residues exposed on the surface are frequently less well defined, however. This probably reflects the fact that these surface residues are more mobile and can have no fixed position. (In a crystal structure this might be seen as diffuse electron density).

Thus, according to the present invention, use of NMR spectroscopic data is combined with computer modeling to arrive at a structural understanding of the topography of fibrin-binding peptides derived from or corresponding to a fibronectin domain. Using this information, one of ordinary skill in the art will know how to achieve rational-based amino acid substitutions (e.g., as presented herein) allowing the production of peptides in which the fibrin-binding affinity is modulated (e.g., increased or decreased) or has greater specificity in accordance with the requirements of the expected therapeutic or diagnostic use of the molecule, preferably, the achievement of greater specificity in fibrin binding.

FBP PRODUCTION.

Once fibrin-binding peptide structure or characteristics have been determined using the above analysis, FBPs can be recombinantly or synthetically produced, or optionally purified, to provide commercially useful amounts of FBPs for use in therapeutic, diagnostic or research applications, according to known method steps, see, e.g., Ausubel et al, eds. *Current Protocols in Molecular Biology*, Wiley Interscience, New York, (1987, 1992, 1993, 1994); and Sambrook et al, *Molecular Cloning, A Laboratory Manual*, 2nd edition, Vols. 1–3, Cold Spring Harbor Press, (1989), which references are herein entirely incorporated by reference.

RECOMBINANT CLONING AND/OR PRODUCTION OF FBPs.

Known method steps for synthesizing oligonucleotide probes useful for cloning and expressing DNA encoding a fibrin-binding peptide of the present invention, based on the teaching and guidance presented herein, are disclosed by, for example, Ausubel, supra Sambrook, supra, and Wu, R., et al., *Prog. Nucl. Acid. Res. Molec. Biol.* 21:101–141 (1978)), which references are entirely incorporated herein by reference.

As a non-limiting example, protein molecules can be fragmented with cyanogen bromide, or with proteases such as papain, chymotrypsin, trypsin, etc. (Oike, Y., et al., *J. Biol. Chem.* 257:9751–9758 (1982); Liu, C., et al., *Int. J. Pept. Protein Res.* 21:209–215 (1983)). Because the genetic code is degenerate, one or more different oligonucleotides can be identified, each of which would be capable of encoding the fragment. The probability that a particular oligonucleotide will, in fact, constitute the actual XXX-encoding sequence can be estimated by considering abnormal base pairing relationships and the frequency with which a particular codon is actually used (to encode a particular amino acid) in the particular host cell used. Such "codon usage rules" are disclosed by Lathe, R., et al., *J. Molec. Biol.* 183:1–12 (1985), and can be used to identify a single oligonucleotide, or a set of oligonucleotides, that contains a theoretical "most probable" nucleotide sequence capable of encoding the fibrin-binding peptide sequence. Although occasionally an amino acid sequence can be encoded by only a single oligonucleotide, frequently the amino acid sequence can be encoded by any of a set of similar oligonucleotides. Importantly, whereas all of the members of this set contain oligonucleotides which are capable of encoding the peptide fragment and, thus, potentially contain the same oligonucLeotide sequence as the native fibronectin gene, only one member of the set contains the nucleotide sequence that is identical to the nucleotide sequence of the gene. Because this member is present within the set, and is capable of hybridizing to DNA even in the presence of the other members of the set, it is possible to employ the unfractionated set of oligonucleotides in the same manner in which one would employ a single oligonucleotide to clone the gene that encodes the peptide.

The oligonucleotide, or set of oligonucleotides, containing the theoretical "most probable" sequence capable of encoding the fibrin-binding peptide is used to identify the sequence of a complementary oligonucleotide or set of oligonucleotides which is capable of hybridizing to the "most probable" sequence, or set of sequences. An oligonucleotide containing such a complementary sequence can be employed as a probe to identify and isolate a DNA sequence encoding the fibrin-binding peptide (Sambrook et al., supra).

A suitable oligonucleotide, or set of oligonucleotides, which is capable of encoding (or which is complementary to a sequence encoding) a fibrin-binding peptide fragment of the fibronectin gene is identified as above, synthesized, and hybridized by means well known in the art, against a DNA or, more preferably, a cDNA preparation derived from cells which are capable of expressing the fibronectin gene. Single stranded oligonucleotide probes complementary to the "most probable" fibrin-binding peptide-encoding sequences can be synthesized using procedures which are well known to those of ordinary skill in the art (Belagaje. R., et al., *J. Biol. Chem.* 254:5765–5780 (1979); Maniatis, T., et al., In: *Molecular Mechanisms in the Control of Gene Expression,* Nierlich et al., Eds., Acad. Press, New York (1976); Wu et al., *Prog. Nucl. Acid Res. Molec. Biol.* 21:101–141 (1978); Khorana, R. G., *Science* 203:614–625 (1979)).

Such a labeled, detectable probe can be used by known procedures for screening a genomic or CDNA library as described above, or as a basis for synthesizing PCR probes for amplifying a CDNA generated from an isolated RNA encoding a target nucleic acid or amino acid sequence. As a further non-limiting example, transformants can be selected for expression by a host cell of a target protein, by use of selection media appropriate to the vector used, or screened by RNA analysis or by the use of antibodies specific for a target protein as a FBP used in a method according to the present invention.

A detectably labeled target probe of this sort can be a fragment of an oligonucleotide that is complementary to a polynucleotide encoding a target protein, as a FBP. Alternatively, a synthetic oligonucleotide can be used as a target probe which is preferably at least about 10 nucleotides in length, in order to be specific for a targeted nucleic acid to be detected, amplified or expressed. The probe can correspond to such lengths of a DNA or RNA encoding a fibronectin molecule, such as SEQ ID NO:1, wherein the probe sequence is selected according to the host cell containing the DNA, e.g., as presented in Table A1.4 of Ausubel et al., supra.

Nucleic acids, or protein encoded thereby, to be detected by a method of the present invention, can be contained in samples isolated from any tissue sample of an animal subject or patient, such as blood, lymph, saliva, urine, CNS, amniotic fluid, skin, hair, feces, or any other tissue, and analyzed by hybridization to labeled probes or reactivity to antibodies. Such probes preferably hybridize to target protein-encoding nucleotides under high stringency conditions or medium stringency conditions, depending on the presence or possible presence of other non-target nucleic acids which also may bind the probes specific for the target nucleic acids. For probe design, hybridization, and stringency conditions, see, e.g., Ausubel supra, sections 6.3 and 6.4, and Sambrook et al, supra. Additional approaches to probe design and detection can also be used, e.g., ligase-mediated gene detection (LMGD), as disclosed, e.g., by Landegren et al., *Science* 241:1077–80 (1988) and fluorescence resonance energy transfer (FRET), as disclosed, e.g., by Wolfe et al., *Proc. Nat. Acad. Sci. USA* 85:8790–94 (1988). See, e.g., Ausubel, supra, at §§9.5.2 (selectable markers), §9.8 (RNA analysis), §§10.6–8 (detection of proteins), §§11.1–1.2 (immunoassays) and §§11.3–.16 (preparation and use of monoclonal, polyclonal and antipeptide antibodies for protein detection).

Additionally, DNA synthesis can be achieved through the use of automated synthesizers. Techniques of nucleic acid hybridization are disclosed by Sambrook et al. (supra), and by Haymes et al. (In: *Nucleic Acid Hybridization,* A Practical Approach, IRL Press, Washington, D.C. (:1985)), which references are herein incorporated by reference. Techniques such as, or similar to, those described above have successfully enabled the cloning of genes for human fibronectin (Suzuki, S. et al., *EMBO J.* 4:2519–2524 (1985), tissue-type plasminogen activator (Pennica, D., et al., *Nature* 301:214–221 (1983)) and others.

In an alternative way of cloning the DNA encoding the fibronectin fibrin-binding peptide, a gene library is prepared by cloning DNA or, more preferably, cDNA from a cell capable of expressing the fibronectin gene into expression vectors. The library is then screened for members either capable of expressing a protein which binds to an antibody specific for the peptide or having a nucleotide sequence that is capable of encoding a peptide that has the same amino acid sequence as a fibrin-binding peptide. In this embodiment, DNA, or more preferably cDNA, is extracted and purified from a cell which is capable of expressing the fibronectin gene. The purified DNA or cDNA is fragmentized (by shearing, endonuclease digestion, etc.) to produce a pool of DNA or cDNA fragments. DNA or cDNA fragments from this pool are then cloned into expression vectors in order to produce a genomic or cDNA library whose members each contain a unique cloned DNA or cDNA fragment.

An "expression vector" is a vector which (due to the presence of appropriate transcriptional and/or translational control sequences) is capable of expressing a DNA (or cDNA) molecule which has been cloned into the vector and thereby being capable of producing a polypeptide or protein. Expression of the cloned sequences occurs when the expression vector is introduced into an appropriate host cell. If a prokaryotic expression vector is employed, then the appropriate host cell would be any prokaryotic cell capable of expressing the cloned sequences. Similarly, if a eukaryotic expression vector is employed, then the appropriate host cell would be any eukaryotic cell capable of expressing the cloned sequences. Importantly, since eukaryotic DNA can contain intervening sequences, and since such sequences cannot be correctly processed in prokaryotic cells, it is preferable to isolate cDNA from a cell which is capable of expressing fibronectin in order to produce a cDNA prokaryotic expression vector library. Alternatively, if the protein is not in its appropriate natural conformation, it will preferably be expressed in a eukaryotic expression system. Procedures for preparing cDNA and for producing a cDNA library are disclosed by Sambrook et al. (supra).

Preferred expression vectors, according to the present invention, are yeast expression vectors such as pMA91, described in the Examples below.

A DNA sequence encoding a fibrin-binding peptide of the present invention, or its functional derivatives, can be recombined with vector DNA in accordance with conventional techniques, including blunt-ended or staggered-ended termini for ligation, restriction enzyme digestion to provide appropriate termini, filling in of cohesive ends as appropriate, alkaline phosphatase treatment to avoid undesirable joining, ligation with appropriate ligases, or the synthesis of fragments by the polymerase chain reaction (PCR). Techniques for such manipulations are disclosed by Sambrook et al., supra, and are well known in the art.

The "polymerase chain reaction or "PCR" is an in vitro enzymatic method capable of specifically increasing the concentration of a desired nucleic acid molecule (reviewed in: Mullis, *Cold Spring Harbor Symp. Quant. Biol.* 51:263–273 (1986); Saiki et al., *Bio/Technology* 3:1008–1012 (1985); and Mullis, K. B. et al., *Meth. Enzymol.* 155:335–350 (1987); see, also, Erlich, H. et al., EP 50,424; EP 84,796, EP 258,017, EP 237,362; Mullis EP 201,184; Mullis et al., U.S. Pat. No. 4,683,202; Erlich, U.S. Pat. No. 4,582,788; and Saiki et al., U.S. Pat. No. 4,683,194).

A nucleic acid molecule, such as DNA, is said to be "capable of expressing" a polypeptide if it contains nucleotide sequences which contain signals for transcriptional and translational initiation, and such sequences are "operably linked" to nucleotide sequences which encode the polypeptide.

Two DNA sequences (such as a promoter sequence and a fibrin-binding peptide-encoding sequences) are said to be operably linked if the nature of the linkage between the two DNA sequences does not (1) result in the introduction of a frame-shift mutation, (2) interfere with the ability of the promoter region sequence to direct the transcription of the peptide-encoding DNA sequence, or (3) interfere with the ability of the peptide-encoding sequence to be transcribed by the promoter region sequence. A promoter region would be operably linked to a DNA sequence if the promoter were capable of effecting transcription of that DNA sequence. Thus, to express the protein, transcriptional and translational signals recognized by an appropriate host are necessary. In order to be "operably linked" it is not necessary that two sequences be immediately adjacent to one another.

The promoter sequences of the present invention can be either prokaryotic, eukaryotic or viral, depending upon the expression system selected. Suitable promoters are repressible, or, more preferably, constitutive, and/or as known in the art. See, e.g. Sambrook, supra; Ausubel, supra.

Preparation of a fibrin-binding peptide having sequences which vary from, but essentially correspond to, portions of native fibronectin, is preferably achieved by site-specific mutagenesis of DNA that encodes an earlier prepared variant, or a nonvariant version, of the peptide. Site-specific mutagenesis allows the production of peptide variants through the use of specific oligonucleotide sequences that encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 20 to 25 nucleotides in length is preferred, with about 5 to 10 residues on either side of the sequence being altered. In general, the technique of site-specific mutagenesis is well known in the art, as exemplified by publications such as Ausubel, supra, and Adelman et al., *DNA* 2:183 (1983), the disclosure of the above references are incorporated herein by reference.

As will be appreciated, the site-specific mutagenesis technique typically employs a phage vector that exists in both a single-stranded and double-stranded form. Typical vectors useful in site-directed mutagenesis include vectors such as the M13 bacteriophage, for example, as disclosed by Messing et al., *Third Cleveland Symposium on Macromolecules and Recombinant DNA*, Editor A. Walton, Elsevier, Amsterdam (1981); Ausubel, supra; and Sambrook, supra, the disclosures of which are entirely incorporated herein by reference. These phages are commercially available and their use is generally well known to those skilled in the related arts. Alternatively, plasmid vectors that contain a single-stranded phage origin of replication (Veira et al., *Meth. Enzymol.* 153:3 (1987)) can be employed to obtain single-stranded DNA.

In general, site-directed mutagenesis in accordance herewith is performed by first obtaining a single-stranded vector that includes within its sequence a DNA sequence that encodes the relevant protein. An oligonucleotide primer bearing the desired mutated sequence is prepared, generally synthetically, for example, by the method of Crea et al., *Proc. Natl. Acad. Sci.* (*USA*) 75:5765 (1978); Ausubel, supra; and Sambrook, supra. This primer is then annealed with the single-stranded protein-sequence-vector carrying the protein-encoding DNA sequence, and then subjected to DNA-polymerizing enzymes such as *E. coli* polymerase I Klenow fragment, to complete the synthesis of the mutation-bearing strand. Thus, the protein-encoding sequence is mutated and the second strand now bears the desired mutation. This heteroduplex vector is then used to transform appropriate cells such as *E. coli* JM101 cells and transformants are selected or screened for the presence of recombinant vectors bearing the mutated sequence arrangement.

After such a clone is isolated, the DNA sequence encoding the mutated protein region can be removed and placed in an appropriate vector for protein production, generally an expression vector of the type that can be employed for transformation of an appropriate host, e.g., bacteria, yeast, insect or mammalian host cell.

ORGANIC SYNTHESIS OF FBPs.

As an alternative to recombinant DNA production, the peptides of the present invention, or fragments, variants or analogues thereof, can be produced by chemical synthesis. Chemical peptide synthesis is a rapidly evolving area in the art, and methods of solid phase peptide synthesis are well-described in the following references, hereby incorporated by reference: Merrifield, *J. Amer. Chem. Soc.* 85:2149–2154 (1963); Merrifield, B., *Science* 232:341–347 (1986); Wade et al., *Biopolymers* 25:S21–S37 (1986); Fields, G. B., *Int. J. Peptide Prot. Res.* 35:161 (1990).

A fibrin-binding peptide can be synthesized as a single chain using the above methods, or can be synthesized in the form of several shorter fragments which themselves lack activity but which can be linked together to form the fibrin-binding peptide.

In general, as is known in the art, such methods involve blocking or protecting reactive functional groups, such as free amino, carboxyl and thiol groups. After polypeptide bond formation, the protective groups are removed (or de-protected). Thus, the addition of each amino acid residue requires several reaction steps for protecting and deprotecting. Current methods utilize solid phase synthesis, wherein the C-terminal amino acid is covalently linked to an insoluble resin particle large enough to be separated from the fluid phase by filtration. Thus, reactants are removed by washing the resin particles with appropriate solvents using an automated programmable machine. The completed polypeptide chain is cleaved from the resin by a reaction which does not affect peptide bonds.

In the more classical method, known as the "tBoc method," the amino group of the amino acid being added to the resin-bound C-terminal amino acid is blocked with tertbutyloxycarbonyl chloride (tBoc). This protected amino acid is reacted with the bound amino acid in the presence of the condensing agent dicyclohexylcarbodiimide, allowing its carboxyl group to form a peptide bond with the free amino group of the bound amino acid. The amino-blocking group is then removed by acidification with trifluoroacetic acid (TFA); with the removed blocking group subsequently decomposing into gaseous carbon dioxide and isobutylene. These steps are repeated cyclically for each additional amino acid residue. A more vigorous treatment with hydrogen fluoride (HF) or trifluoromethanesulfonyl derivatives is common at the end of the synthesis to cleave the benzyl-derived side chain protecting groups and the peptide-resin bond.

More recently, the preferred "Fmoc" technique has been introduced as an alternative synthetic approach, offering milder reaction conditions, simpler activation procedures and compatibility with continuous flow techniques. This method was used, e.g., to prepare the peptide sequences disclosed in the present application. Here, the α-amino group is protected by the base labile 9-fluorenylmethoxycarbonyl (Fmoc) group. The benzyl side chain protecting groups are replaced by the more acid labile t-butyl derivatives. Repetitive acid treatments are replaced by deprotection with mild base solutions, e.g., 20% piperidine in dimethylformamide (DMF), and the final HF cleavage treatment is eliminated. A TFA solution is used instead to cleave side chain protecting groups and the polypeptide resin linkage simultaneously. At least three different polypeptide-resin linkage agents can be used: substituted benzyl alcohol derivatives that can be cleaved with 95% TFA to produce a polypeptide acid, methanolic ammonia to produce a polypeptide amide, or 1% TFA to produce a protected polypeptide which can then be used in fragment condensation procedures, as described by Atherton, E. et al., *J. Chem. Soc. Perkin Trans.* 1:538–546 (1981) and Sheppard, R. C. et al., *Int. J. Polypeptide Prot. Res.* 20:451–454 (1982). Furthermore, highly reactive Fmoc amino acids are available as pentafluorophenyl esters or dihydro-oxobenzotriazine esters derivatives, saving the step of activation used in the tBoc method.

FIBRIN ACTIVITY SCREENING ASSAYS.

The fibrin-binding activity of a given lot of FBP or anti-fibronectin or anti-peptide antibody (as described below), can be determined according to well known method steps. Those skilled in the art will be able to determine operative and optimal assay conditions for each determination by employing routine experimentation.

Several assays are particularly useful for detecting the binding to fibrin of the fibrin-binding peptide of the present invention: (1) by the ability to bind to fibrin coated surfaces, using an ELISA assay developed by the present inventors or by a similar RIA; (2) by ligand affinity chromatography on fibrin-SEPHAROSE™; and (3) in an in vitro fibrin clot binding assay (Thorsen et al., *Thrombos. Diathes. Haemorrh.*, 28, 65–74 (1972)), (4) protein blotting reaction, as well as other clot assays.

For the fibrin-binding ELISA, microplates are coated with fibrin using known methods (Christman et al., *Biochim. Biophys. Acta.* 340:339–347 (1974); Unkeless et al., *J. Biol. Chem.*, 249, 4295–4305 (1974)). In a preferred embodiment, microtiter (e.g., IMMULON-2) plates are coated with fibrinogen at a concentration of 50–1000 ng/well/0.1 ml of Tris buffered saline (TBS). The plates are allowed to dry for 24 hours at 37° C. and 0.1 ml of thrombin (20 NIH units/100 ml) containing TRASYLOL (aprotinin, 400 K.I. units/100 ml) in TBS are added to each well and the plates incubated for 2 hours at 37° C. Each well is washed one time with phosphate buffered saline (PBS) or TRIS-buffered saline (TBS) and the plates are blocked for 1.5 hours with 1% bovine serum albumin (BSA) in TBS to prevent non-specific binding. If a binding partner for the fibrin-binding peptide is available, such as, for example, an antibody according to the present invention, a direct binding assay can be performed. The putative fibrin-binding peptide under assay is preferably diluted in 0.05M Tris containing 0.1% BSA, 0.05% TWEEN-20 (polysorbate-20), 0.1M NaCl, pH 7.6 (TBST-BSA) and incubated at concentrations ranging, for example, from 25–1000 ng for 2 hours to overnight (at either 4° C., 37° C., or room temperature). The wells are then washed with TBST-BSA and incubated with the binding partner, such as the antibody specific for the fibrin-binding peptide (0.05 µl) to the putative FBP suspected of having fibrin-binding activity for 1 hour. Optimal final concentrations can be readily determined by one of ordinary skill in the art without undue experimentation. Following washes with TBST-BSA, the wells are incubated for 1 hour with an enzyme-conjugated second binding partner, preferably biotinylated, fluorescinated, or alkaline phosphatase- or peroxidase-conjugated second binding partner which can bind specifically to the first binding partner. Thus, for example, if the first binding partner is a rabbit antibody specific for the 11 kDa fibrin-binding peptide, the second binding partner will be, for example, goat antibodies specific for rabbit-IgG. The reaction is developed with a chromogenic substrate for the particular enzyme used. Thus, if alkaline phosphatase is the enzyme used, a preferred substrate is p-nitrophenyl phosphate (Sigma phosphatase substrate tablets Sigma Chemical Co.) dissolved in 10% diethanolamine containing 1.0 mM $MgCl_2$, pH 9.8. Binding is assessed spectrophotometrically, preferably using an ELISA plate reader, e.g., at 410 nm.

As an alternative to using a tagged second antibody to detect the bound fibrin-binding antibody one can alternatively use a enzyme conjugated antibody specific for the fibrin-binding peptide, such as, preferably, by biotinylating such antibody. This will obviate the necessity of a second antibody.

In another embodiment, binding can be measured using a competitive inhibition assay. In this case, the sample being assayed for fibrin-binding activity is incubated with either intact fibronectin or the 11 kDa fragment or any other known fibrin-binding fragment/peptide, at various concentrations, for an appropriate time period (usually one hour) and inhibition of binding is determined. If intact fibronectin is used, only partial inhibition of binding should be observed with a particular fibrin-binding peptide corresponding to a single fibronectin binding site, since fibronectin has two fibrin-binding sites. Alternatively, the sample being assayed can be allowed to react with the fibrin on the plate for a certain interval, followed by addition of fibronectin or another known fibrin-binding peptide after the unknown has been allowed to bind. If the sample contains a fibrin-binding peptide in sufficient concentration, it will competitively inhibit binding of the known fibrin-binding protein or peptide. Also, an Ab to either Fn or the FBP can be used to competitively inhibit the FBP or Fn binding to fibrin. The Ab can be preincubated with the FBP or Fn to inhibit binding by blocking the specific site involved in fibrin binding.

The bound fibronectin can be detected by any known method such as by directly biotinylating or otherwise enzyme conjugating or radiolabelling the fibronectin directly, or by using a labelled antibody against fibronectin which does not cross-react with any of the fibrin-binding peptides used in the competitive assay.

An alternate method for measuring binding to fibrin is through the use of fibrin affinity chromatography. In this approach, for example, a sample containing a fibrin-binding peptide is added to fibrin coupled to a solid support, for example, fibrin-SEPHAROSE™. Incubations are preferably performed at 4° C. to promote binding. The FBP is either incubated with the matrix with end over rotation or applied to the fibrin-matrix in a column. Although fibrin binding does occur at room temperature and at 37° C., maximum binding is obtained at 4° C. Because of its affinity for fibrin, the fibrin-binding peptide will bind to the fibrin matrix while non-fibrin-binding proteins and peptides will not bind. The fibrin-binding peptide can be removed and thereby purified by elution with any reagent that disrupts the specific binding to the fibrin matrix.

FIBRIN CLOT BINDING ASSAYS.

Fibrin binding is also routinely determined using an assay which can mimic the physiological binding of a fibrin-binding peptide to fibrin, based on detecting fibrin binding to prepared fibrin clots and subsequent microscopic examination. For example, the fibrin-binding peptide can be labeled with fluorescein (Dickler, H. et al., *J. Exp. Med.* 140: 508 (1974)) or by radiolabeling, for example with a radioactive isotope of iodine. In an in vitro assay, if the FBP is radiolabeled, for example, one can simply determine the counts per minute (CPMs) bound to the experimental clot, which will be directly related to the amount of FBP bound to the clot (specific activity).

The method for fibrin clot formation is described by Thorsen et al., (supra ). Preferably, a mixture of 0.2%, bovine plasminogen-free fibrinogen is incubated with thrombin in saline barbital buffer (SBB) and the fibrin is separated from the solution by winding on a glass rod at room temperature. All fluid is released from the clot by pressure and the clot incubated with the labeled fibrin-binding peptide for various periods of time. Following gentle washing of the clot in SBB to remove unbound labeled protein, the clot is quickly frozen at $-20°$ C., cut in cryostat to sections 6–8 microns thick, and collected on acid washed and 3-aminopropyltriethoxysilane treated microscope slides. The slides are preferably fixed in 10% formalin solution for 60 minutes, rinsed with water, stained (Hematoxylin or toluidine blue or another appropriate stain) and either mounted with a water or solvent insoluble slide mounting solution, depending on the chosen stain (e.g., Aquamount or Permount).

If a fluorescent label is used, the slides are examined using conventional fluorescence microscopy. If a radiolabel is used, the slides are subjected to autoradiography to detect binding. Attachment of the label is expected only around the periphery of the clot with such procedures. Controls for such assays include similarly labeled proteins which do not bind to fibrin and known fibrin-binding proteins or peptides of similar molecular mass.

Non-limiting examples of methods for detecting fibrin-binding activity of FBPs of the present invention also include other fibrin clot binding assays, which method steps are well known in the art, and based on the teaching and guidance presented herein, include the following.

One alternative method of detecting fibrin binding is to test the binding of radiolabeled FBPs to clots prepared in vitro. Radiolabeled FBPs are stored for no longer than two weeks at $-20°$ C. in 0.1% BSA-PBS. Fibrin binding of $^{125}$Iodine-FBPs or other radiolabeled FBPs is performed in at least one of two ways: 1) during clot formation and 2) at various time periods after clot formation. This determines the efficacy of FBPs in binding to both newly forming clots (thrombi) and old clots in vivo. If FBPs continue to be incorporated into forming thrombi with time and remain relatively unchanged in their binding to preformed (old) thrombi over time, then radiolabeled FBPs are used in vivo to distinguish old thrombi from actively forming thrombi.

The specificity of FBPs binding to clots will be determined by competing radiolabeled FBPs with unlabeled intact Fn, such as, but not limited to the 11 kDa and 25.9 kDa FBPs, as well as recombinant FBPs of the present invention which have been shown to have fibrin-binding activity. Preferably, all or substantially all of the fibrin-binding sites (optimally 75%) are saturated in order to observe competition. Thus, clot size will be varied until saturation is obtained (binding of radiolabeled FBPs has reached a plateau). For these experiments, various concentrations of cold FBPs will be added together with the radiolabeled FBPs to the clot, and inhibition of binding determined. This will demonstrate the relative affinities of various FBPs (by displacement) and specificity of the interaction. Binding of $^{125}$I-FBPs to preformed fibrin clots will be performed as above, except the $^{125}$I-FBP will not be added until after the clot has been formed and terminated at 30 minutes. The $^{125}$I-FBP will be added for various time periods, during or after clot formation, and fibrin binding quantitated as described above.

FLUORESCENCE FIBRIN CLOT BINDING ASSAYS.

Another method for determining FBPs binding to prepared fibrin clots is to label the FBP with either fluorescein according to known method steps, e.g., according to Kluftinger, et al., *Infect. Immun.* 57, 817, (1989) or by radiolabel with $^{125}$Iodine, and determine fibrin binding histologically. The method for fibrin clot formation will be performed according to known method steps, as described, e.g., according to Engvall, et al. (*J. Exp. Med.* 147, 1584–1595 (1978)). Controls can be predetermined labeled non-fibrin-binding proteins and known FBPs of similar molecular masses. Alternatively, fresh frozen sections of a formed clot will be incubated in humido with the fluorescein or radioiodinated FBP. If the FBP is immunoreactive with any of our antisera, it will not need to be labeled and the procedure will follow with fluorescein labeled goat anti-rabbit IgG. $^{125}$I labeled protein A may also be used as a detection system.

Radiolabeled FBP binding to developing and preformed clots is also performed in the presence of effectors of clot formation. Fibrin binding experiments are performed in the presence of thrombin, hirudin (inhibitor of thrombin), calcium (clot formation is calcium dependent), and heparin (inhibitor of clot formation) to determine their effects on $^{125}$I-FBP binding to both forming and preformed clots. Many patients that would receive FBP for imaging, etc., will be heparinized and thus, it is important to determine the extent that heparin would inhibit FBPs from binding to thrombi. The effect of plasma transglutaminase (Factor XIII) cross-linking on FBPs binding to fibrin clots is also determined. The addition of the primary amines spermidine and/or putrescine, which are inhibitors of Factor XIII, will indicate the contribution of Factor XIII, in blood, to FBPs binding to fibrin clots, according to the present invention.

FBP HAVING FIBRIN-BINDING ACTIVITY.

Once FBPs of the present invention have been produced by recombinant or synthetic methods, or by proteolytic cleavage from the intact fibronectin molecule, and shown to have activity by one or more of the assays presented herein, such FBPs of the present invention are then used in compositions, diagnostic methods or therapeutic methods, as further described herein.

FIBRIN-BINDING PEPTIDE DIAGNOSTIC METHODS

In detecting an in vivo site of thrombosis, fibrin deposition, atherosclerotic plaque, cancer, or a bacterial infection in a subject, a detectably labeled fibrin-binding peptide of the present invention is advantageously given in a dose which is diagnostically effective. The term "diagnostically effective" means that the amount of detectably labeled fibrin-binding peptide administered is sufficient to enable detection of the site of thrombosis, fibrin deposition, atherosclerotic plaque, cancer or bacterial infection, compared to the background signal.

Generally, the dosage of detectably labeled fibrin-binding peptide for diagnosis will vary depending on considerations such as age, condition, sex, and extent of disease in the patient, contraindications and/or the presence of other medications, if any, and other variables, to be adjusted by the individual physician. Dosage can vary from 0.1 µg/kg to 100 mg/kg, preferably 0.01 mg/kg to 10 mg/kg.

The term "diagnostically labeled" means that the fibrin-binding peptide has attached to it a diagnostically detectable label. There are many different labels and methods of labeling known to those of ordinary skill in the art. Examples of the types of labels which can be used in the present invention include radioactive isotopes, paramagnetic isotopes, and compounds which can be imaged by positron emission tomography (PET). Those of ordinary skill in the art will know of other suitable labels for binding to the fibrin-binding peptides used in the present invention, or will be able to ascertain such, using routine experiments. Furthermore, the binding of these labels to the fibrin-binding peptide can be done using standard techniques common to those of ordinary skill in the art, such as crosslinking, covalent attachment, non-covalent attachment, or complexing.

For diagnostic in vivo imaging, the type of detection instrument available is a major factor in selecting a given label, such as radionuclide, paramagnetic isotope or PET imaging agent. For example, the radionuclide chosen must have a type of decay which is detectable by a given type of instrument. In general, any conventional method for visualizing diagnostic imaging can be utilized in accordance with this invention.

Another important factor in selecting an imaging label for use in in vivo diagnosis is that the half-life of a radionuclide be long enough so that it is still detectable at the time of maximum uptake by the target tissue, but short enough so that deleterious radiation of the host is minimized. In one preferred embodiment, a radionuclide used for in vivo imaging does not emit particles, but produces a large number of photons in a 140–200 keV range, which can be readily detected by conventional gamma cameras.

For in vivo diagnosis, radionuclides can be bound to a fibrin-binding peptide either directly or indirectly by using an intermediary functional group. Intermediary functional groups which are often used to bind radioisotopes existing as metallic ions to fibrin-binding peptides are the chelating agents, diethylene triamine pentaacetic acid (DTPA) and ethylene diamine tetracetic acid (EDTA). Non-limiting examples of metallic ions which can be bound to fibrin-binding peptides are $^{99}$Tc, $^{123}$I, $^{111}$In, $^{131}$I, $^{97}$Ru, $^{67}$Cu, $^{67}$Ga, $^{125}$I, $^{68}$Ga, $^{72}$As, $^{89}$Zr, and $^{201}$Tl.

In addition to identifying and characterizing sites or sizes of thrombosis or fibrin deposition, methods of the invention can be used to monitor the course of thrombosis, fibrin deposition, atherogenesis, thrombolysis and/or atherogenolysis in an individual. Thus, by measuring the increase or decrease in the size or number of binding sites for the peptide of the invention, it is also possible to determine whether a particular therapeutic regimen is effective, e.g., when aimed at ameliorating the condition, or directed to the development of thrombosis, fibrin deposition or atherogenesis, or to regulation of thrombolysis or atherogenolysis.

THERAPEUTIC METHODS.

In another embodiment, fibrin-binding peptides of this invention, directly as pharmaceutical compositions, containing at least one FBP and a pharmaceutically acceptable carrier or diluent, or a FBP in "therapeutically conjugated" form, are used for therapy either by their own action or by targeted delivery of the therapeutic agent to fibrin at the site of a fibrin related pathology, such as but not limited to thrombosis, fibrin deposition, atherosclerosis, tumor, cancer, wound, infection, other vascular disease.

The term "therapeutically conjugated" means that the fibrin-binding peptide is conjugated to a therapeutic agent. Therapeutic agents used in this manner are preferably thrombolytic or fibrinolytic agents, such as, but not limited to tPA or analogues thereof, urokinase, streptokinase, prourokinase, or anisoylated plasminogen-streptokinase activator complex (EMINASE™). Other therapeutic agents which can be coupled to the fibrin-binding peptides according to the present invention are chemicals, compounds, compositions, drugs, radioisotopes, lectins, and toxins, which are not limited to those listed here. Alternatively, a cloned recombinant "hybrid" molecule can be synthesized/produced by using the amino acid sequence of a FBP and a known protease or protease domain (e.g., of plasminogen activators) to be used for fibrin-binding and clot lysis.

Also intended within the scope of the present invention, e.g., to target growth factors specifically to areas of fibrin binding deposition for therapy or diagnosis, are fibrin-binding peptides bound to growth factors such as epidermal growth factor (EGP), platelet-derived growth factor (PDGF), transforming growth factor-α (TGF-α), transforming growth factor-β (TFG-β), fibroblast growth factor (FGF), tumor necrosis factor-α or -β (TNFα or TNFβ), any of the interleukins (IL-1 to IL-13) or interferons, erythropoietin (EPO), or colony stimulating factors (CSFs). FBPs can also be bound to albumin, a blood factor such as Factor VIIIa or XIIIb, polyethylene glycol, superoxide dismutase, or other proteins having a desired biological activity.

The therapeutic dosage of therapeutic compounds and compositions to be administered is an amount which is therapeutically effective, and will be known or routinely determinable by one skilled in the related arts. The dose is also dependent upon the age, health, and weight of the recipient, kind of concurrent treatment, if any, frequency of treatment, and the nature of the effect desired as determined according to known methods.

Other therapeutic agents which can be coupled to the fibrin-binding peptides or specific antibodies of this invention are known, or can be easily ascertained, by those of ordinary skill in the art. Examples of radioisotopes which can be bound to the fibrin-binding peptide for therapeutic purposes, used according to the method of the invention, are $^{125}$I, $^{131}$I, $^{90}$Y, $^{67}$Cu, $^{217}$Bi, $^{211}$At, $^{212}$Pb, $^{47}$Sc, and $^{109}$Pd.

The present invention also provides a method for treating a subject with vascular disease, such as, but not limited to, cardiovascular, cerebrovascular and/or peripheral vascular disease, such as that associated with thrombosis, fibrin deposition and/or atherosclerotic plaque, which method comprises administering to the subject a therapeutically effective amount of the fibrin-binding peptide, composition and/or therapeutic conjugate of the FBP, as described herein. Non-limiting examples of subjects who can benefit from the treatment compositions and methods of the present invention are patients with cerebrovascular pathologies, cardiovascular disorders, including acute myocardial infarction or angina, patients which have been subjected to angioplasty or coronary bypass surgery, patients receiving other thrombolytic therapy, or patients with thrombotic and/or fibrinolytic disease or clotting disorders.

The present invention also provides a method for treating a subject with a wound, comprising administering to the subject a therapeutically effective amount of a fibrin-binding peptide or therapeutic conjugate of the peptide, as described herein, to achieve improved healing of the wound relative to not administering any FBP. The wound can be superficial, lacerated, contused, incised, open, penetrating or punctured, as an external or internal wound anywhere in the body. Non-limiting examples can include a cutaneous wound, such as an incision, a skin deficit, a skin graft, or a burn. The wound can also be an eye wound such as a corneal epithelial wound or a corneal stromal wound, or a tendon injury. Growth factors, such as presented herein, bound to a FBP, can be used to target a wound to promote healing of the wound topically, systematically or parenterally.

By administering a fibrin-binding peptide of the present invention, it is possible to prevent further fibrinogenesis because, e.g., by binding to fibrin, a FBP can prevent further fibrin-fibrin interactions and thereby, e.g., preventing increase in size of a growing thrombus or developing plaque. Thus, FBPs of the present invention are useful, e.g., in preventing disseminated intravascular coagulation (DIC), which occurs in end-stage cancer and in other disease states.

The relationship between primary tumors, metastatic tumors, and the fibrinogen/fibrin and plasminogen/plasmin systems is complex (Markus, Sem. Thrombos. Hemostas. 10:61–70 (1984); Kwaan, Sem. Thrombos. Hemostas, 10:71–79 (1984)). It is clear that clotting is dysregulated in metastatic cancer, in part because of chelation or consumption of various clotting factors. The peptides of the present invention can be used to regulate the clotting system in cancer by preventing further fibrinolysis. Because of the fibrin associated with tumors, FBPs of the present invention can be used as diagnostic agents to image certain tumors. In conjunction with thrombolytic agents, as described herein, the peptides can be used to break up clots. Thus, one of ordinary skill in the art will appreciate how to make judicious use of the peptides of the present invention to regulate the clotting system in the treatment of cancer patients.

The fibrin-binding peptides of the present invention can also be administered as a countermeasure to thrombolytic therapy, e.g., to regulate one or more undesired side effects, such as plasma fibrinogen breakdown which leads to bleeding disorders. For example, an effective dose of a FBP can be administered following tPA administration to stop the thrombolytic action of the tPA because tPA activity requires fibrin binding. They can also be used to treat diseases with similar effects,such as α-2 plasmin inhibitor deficiency in which there is constant fibrinolysis.

The fibrin-binding peptides of the present invention can also be used to inhibit the adhesion of bacteria to the extracellular matrix, as in wounds. This property can be assessed in a competition assay (Vogel, T. et al., infra) in which adherence of *Staphylococcus aureus* organisms to a fibronectin-coated plastic surface is measured. It is known that a recombinant 31 kDa fibrin-binding domain corresponding to part of the N-terminal half of fibronectin inhibits such adhesion (Vogel et al., infra).

Because of the ability of fibrin-binding peptides to bind certain bacteria, the present invention provides a method for preventing or treating a bacterial infection, which comprises administering to a subject a therapeutically effective amount of a fibrin-binding peptide corresponding to the N-terminal part of fibronectin, preferably the $^4$F1.$^5$F1 module or the $^4$F1 module. This method can be particularly useful to treat catheter sepsis associated with the presence of a bronchial or other catheter, or other type of implant which is susceptible to staphylococcal infection.

The present invention also includes a method for treating a subject with cancer, which comprises administering a therapeutically effective amount of the fibrin-binding peptide or therapeutic conjugate of the peptide, as described above, which is effective in retarding metastasis.

This invention can also be utilized to detect thrombosis or fibrin deposition, such as that associated with atherosclerotic plaques or microthrombi as in myocardial infarction, thrombo-emboli, and the like, at a wide variety of body sites including, but not limited to organs such as the heart, abdomen, or lungs, or cerebrovascular or vascular walls anywhere in the body.

The invention is also useful as a means to evaluate the efficacy of, and responses to, therapeutic treatment of thrombosis or fibrin deposition.

PHARMACEUTICAL COMPOSITIONS.

Preparations of the imaging fibrin-binding peptides or therapeutically-conjugated fibrin-binding peptides for parenteral administration include sterile aqueous or non-aqueous solutions, suspensions, and emulsions. Examples of non-aqueous solvents are propyleneglycol, polyethyleneglycol, vegetable oil such as olive oil, and injectable organic esters such as ethyloleate. Aqueous carriers include water, alcoholic/aqueous solutions, emulsions or suspensions, including saline and buffered media, parenteral vehicles including sodium chloride solution, Ringer's dextrose, dextrose and sodium chloride, lactated Ringer's, or fixed oils. Intravenous vehicles include fluid and nutrient replenishers, such as those based on Ringer's dextrose, and the like. Preservatives and other additives can also be present, such as, for example, antimicrobials, antioxidants, chelating agents, and inert gases and the like. See, generally, *Remington's Pharmaceutical Science*, 16th ed., Mac Eds, 1980.

Preparations of the imaging Eibrin-binding peptides or therapeutically-conjugated fibrin-binding peptides of the present invention can be administered by any means that achieve their intended purpose. For example, administration can be by parenteral, including subcutaneous, intravenous, intramuscular, intra-arterial, intraperitoneal, or transdermal routes. Alternatively, or concurrently, administration can be by the oral route. A preferred route of administration of the detectably labeled fibrin-binding peptides for imaging is the intravenous route. The fibrin-binding peptide can be administered in a single bolus, or by gradual perfusion, which is preferably intravenous and uses peristaltic means to accomplish the gradual perfusion.

ANTIBODIES AND METHODS.

The term "antibody" as used herein is meant to include polyclonal antibodies, monoclonal antibodies (mAbs), chimeric antibodies, single-chain antibodies, recombinantly produce humanized antibodies, and anti-idiotypic (anti-Id) antibodies.

Polyclonal antibodies are heterogeneous populations of antibody molecules derived from the sera of animals immunized with an antigen.

Monoclonal antibodies are a substantially homogeneous population of antibodies to specific antigens. MAbs can be obtained by methods known to those skilled in the art. See, e.g., Sambrook, supra; Ausubel, supra, e.g., §11; Harlow and Lane, *ANTIBODIES: A LABORATORY MANUAL* Cold Spring Harbor Laboratory (1988); Colligan et al., eds., *Current Protocols in Immunology*, Greene Publishing Assoc. and Wiley Interscience, New York, (1992, 1993, 1994), the contents of which references are incorporated entirely herein by reference. Such antibodies can be of any immunoglobulin class including IgG, IgM, IgE, IgA and any subclass thereof. The hybridoma producing the mAbs of this invention can be cultivated in vitro or in vivo. Production of high titers of mAbs by in vivo production makes this the presently preferred method of production. Briefly, cells from the individual hybridomas are injected intraperitoneally into pristane-primed BALB/c mice to produce ascites fluid containing high concentrations of the desired mAbs. MAds of isotype IgM or IgG can be purified from such ascites fluid, or from culture supernatants, using column chromatography (e.g., protein A-Sepharose or Gamma-Bind™) or other known method steps.

Chimeric antibodies are molecules to different portions of which are derived from different animal species, such as those having a variable region derived from a murine mAb and a human immunoglobulin constant region. Chimeric antibodies and methods for their production are known in the art (Harlow, supra, Colligan, supra ; Cabilly et al, *Proc. Natl. Acad. Sci. USA* 81:3273–3277 (1984); Morrison et al., *Proc. Natl. Acad. Sci. USA* 81:6851–6855 (1984); Boulianne et al., *Nature* 312:643–646 (1984); Neuberger et al., *Nature* 314:268–270 (1985); Taniguchi et al., European Patent Application 171496 (published Feb. 19, 1985); Robinson et al., International Patent Publication No. PCT/US86/02269 (published 7 can 1987); Liu et al., *Proc. Natl. Acad. Sci. USA* 84:3439–3443 (1987); Better et al., *Science* 240:1041–1043 (1988)). These references are hereby entirely incorporated by reference.

An anti-idiotypic (anti-Id) antibody is an antibody which recognizes unique determinants generally associated with the antigen-binding site of an antibody. An anti-Id antibody can be prepared by immunizing an animal of the same species and genetic type (e.g. mouse strain) as the source of the mAb with the mAb to which an anti-Id antibody is to be prepared. The immunized animal will recognize and respond to the idiotypic determinants of the immunizing antibody by producing an antibody to these idiotypic determinants (the anti-Id antibody).

Accordingly, mAbs generated against the fibrin-binding peptide of the present invention can be used to induce anti-Id antibodies in suitable animals, such as BALB/c mice. Spleen cells from such immunized mice are used to produce anti-Id hybridomas secreting anti-Id mAbs.

The anti-Id mAbs thus have their own idiotypic epitopes, or "idiotopes" structurally similar to the epitope being evaluated, such as an epitope of a fibrin-binding peptide. Such anti-Id antibodies can also be used to target to fibrin-binding peptides.

The term "antibody" is also meant to include both intact molecules as well as fragments thereof, such as, for example, Fab and F(ab')₂, which are capable of binding antigen. Fab and F(ab')₂ fragments lack the Fc fragment of intact antibody, clear more rapidly from the circulation, and can have less non-specific tissue binding than an intact antibody (Wahl et al., *J. Nucl. Med.* 24:316–325 (1983)).

It will be appreciated that Fab and F(ab')₂ and other fragments of the antibodies useful in the present invention can be used for the detection and quantitation of fibronectin or a fibrin-binding peptide corresponding thereto, according to the methods disclosed herein for intact antibody molecules. Such fragments are typically produced by proteolytic cleavage, using enzymes such as papain (to produce Fab fragments) or pepsin (to produce F(ab')₂ fragments).

The antibodies (or fragments thereof) useful in the present invention can be employed histologically to detect or visualize the presence of fibronectin or a fibrin-binding peptide corresponding thereto. Such an assay typically comprises incubating a biological sample from a subject in the presence of a detectably labeled antibody capable of identifying fibronectin or a fibrin-binding peptide, and detecting the antibody bound in a sample.

The antibodies according to the present invention are useful for immunoassays to detect or quantitate the presence of fibronectin, or a fibrin-binding peptide of the present invention. Similarly, the fibrin-binding peptides of the present invention can be used in immunoassay-like binding assays to detect or quantitate the amount of fibrin in a sample. Assays using these two separate compositions of the present invention, antibodies and fibrin-binding peptides, will be discussed together below, since the basic approach is essentially the same.

Such an immunoassay typically comprises incubating a biological sample from a subject in the presence of a detectably labeled antibody (or fibrin-binding peptide) capable of reacting with and thereby identifying the antigen or binding partner, and detecting the antibody (or fibrin-binding peptide) which is bound in a sample.

Thus, in this aspect of the invention, a biological sample can be incubated with nitrocellulose, or other solid support or carrier (e.g., microtiter plates) which is capable of immobilizing cells, cell particles or soluble proteins. The support can then be washed with suitable buffers followed by treatment with the detectably labeled antibody (or fibrin-binding peptide). The carrier can then be washed with the buffer a second time to remove unbound antibody or peptide. The amount of bound label on the solid support can then be detected by conventional means.

By "solid phase support" or "carrier" is intended any support capable of binding antigen or antibodies. Well-known supports, or carriers, include glass, polystyrene, polypropylene, polyethylene, dextran, nylon, amylases, natural and modified celluloses, polyacrylamides, agaroses, and magnetite. The nature of the carrier can be either soluble to some extent or insoluble for the purposes of the present invention. The support material can have virtually any possible structural configuration so long as the coupled molecule is capable of binding to an antigen or antibody. Thus, the support configuration can be spherical, as in a bead, or cylindrical, as in the inside surface of a test tube or microtiter well, or the external surface of a rod. Alternatively, the surface can be flat such as a sheet, test strip, etc. Preferred supports include polystyrene beads or polystyrene wells treated appropriately by the manufacturer so as to bind the desired antigens. Those skilled in the art will know many other suitable carriers for binding antibody or antigen, or will be able to ascertain the same by use of routine experimentation.

As regards to use of the antibody of the present invention, a preferred immunoassay is an enzyme immunoassay (EIA), or enzyme-linked immunosorbent assay (ELISA). An enzyme is conjugated directly to the antibody of the present invention or to a second binding partner for the antibody. This enzyme, in turn, when later exposed to its substrate, will react with the substrate in such a manner as to produce a chemical moiety which can be detected, for example, by spectrophotometric, fluorometric or by visual means. Enzymes useful for labeling the antibody or fibrin-binding peptide according to the present invention include, but are not limited to, maleate dehydrogenase, staphylococcal nuclease, delta-V-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase.

Detection can be accomplished using any of an alternate variety of immunoassays, such as radioimmunoassay (RIA) See, for example, Chard, T., In: Work. T. S., et al., *Laboratory Techniques and Biochemistry in Molecular Biology*, North Holland Publishing Company, New York, (1978), incorporated by reference herein. The radioactive isotope can be detected by such means as the use of a gamma counter or a scintillation counter or by autoradiography. Isotopes which are particularly useful for the purpose of the present invention are well-known in the art.

For assays in which the detectable label is a fluorescent compound, the antibody or peptide of the invention can be labeled with any of a number of fluorescent compounds, such as fluorescein isothiocyanate, rhodamine, phycoerythrin, phycocyanin, allophycocyanin, o-phthaldehyde and fluorescamine. The antibody or peptide can also be detectably labeled using fluorescence emitting metals such as $^{152}$Eu, or others of the lanthanide series. These metals can be attached to the protein using such metal chelating groups as diethylenetriaminepentaacetic acid (DTPA) or ethylenediaminetetraacetic acid (EDTA).

The antibody or peptide also can be detectably labeled by coupling it to a chemiluminescent compound. The presence of the chemiluminescent-tagged antibody or fibrin-binding peptide is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound can be used to label the antibody or peptide of the present invention. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

Detection of binding of the antibody or peptide can be accomplished using a liquid scintillation counter for a label which is a β-emitter, a gamma counter for a radioactive gamma emitter, or by a fluorometer, for example, if the label is a fluorescent material. In the case of an enzyme label, the detection is preferably by calorimetric (spectrophotometric) methods. Detection can also be accomplished by visual comparison of the extent of enzymatic reaction of a substrate in comparison with similarly prepared standards.

The immunoassays of the present invention can be forward assays, simultaneous or reverse, sandwich assays or competitive assays, using single antibodies or combinations or antibodies, as is well-known in the art.

Having now generally described the invention, the same will be more readily understood through reference to the following examples which are provided by way of illustration, and are not intended to be limiting of the present invention, unless specified.

EXAMPLE I

Purification of Fibrin-Binding Peptides from Fibronectin a). Proteolytic digestion of Fn.

Fibronectin was obtained from the Nelysink Blood Center and further purified by lysine-SEPHAROSE™ chromatography, to remove contaminating enzymes (plasmin), followed by gelatin affinity chromatography (0.1M Tris, pH 7.6) (Gold et al. *Proc. Natl. Acad. Sci.* 76:4803–4807 (1979); Rostagno et al., *J. Immunol.* 143:3277–3282 (1989)). Purified Fn (1 mg/ml in 0.1M Tris-HCl buffer, pH 7.6) was incubated with subtilisin Carlsberg type VIII (Sigma), at an enzyme substrate ratio of 1:100 (w/w) for 1 hour at 37° C. The reaction was terminated by the addition of PMSF (Sigma Chem. Co.) to a final concentration of $10^{-3}$, and the digested Fn subjected to sequential affinity chromatography through gelatin-SEPHAROSE™ (Heene, et al., (1973) *Thrombosis Res* 2, 137–154) and fibrin-SEPHAROSE™ (Gold et al., *Biochemistry* 22:4113–4119 (1983); Stathakis, N. E. et al., *Blood* 51:1211–1222 (1978)).

b). Preparation of fibrin-SEPHAROSE™.

Bovine fibrinogen was cross-linked to CNBr-activated SEPHAROSE™ (5 mg/ml beads) according to the manufacturer's instructions. Coupled fibrinogen was subsequently converted to fibrin by incubation with human thrombin to a final concentration of 5 NIH units/ml and 100 K.I. (kallikrein inhibitory) units/ml of aprotinin (in 0.05M Tris-HCl buffer, pH 7.6, containing 0.1M NaCl and 0.01M EDTA) for three hours, at room temperature (Gold, et al. (1983) *Biochemistry* 22, 4113–4119).

c). Isolation of 25.9 kDa fibrin-binding fragment.

Figure 3:
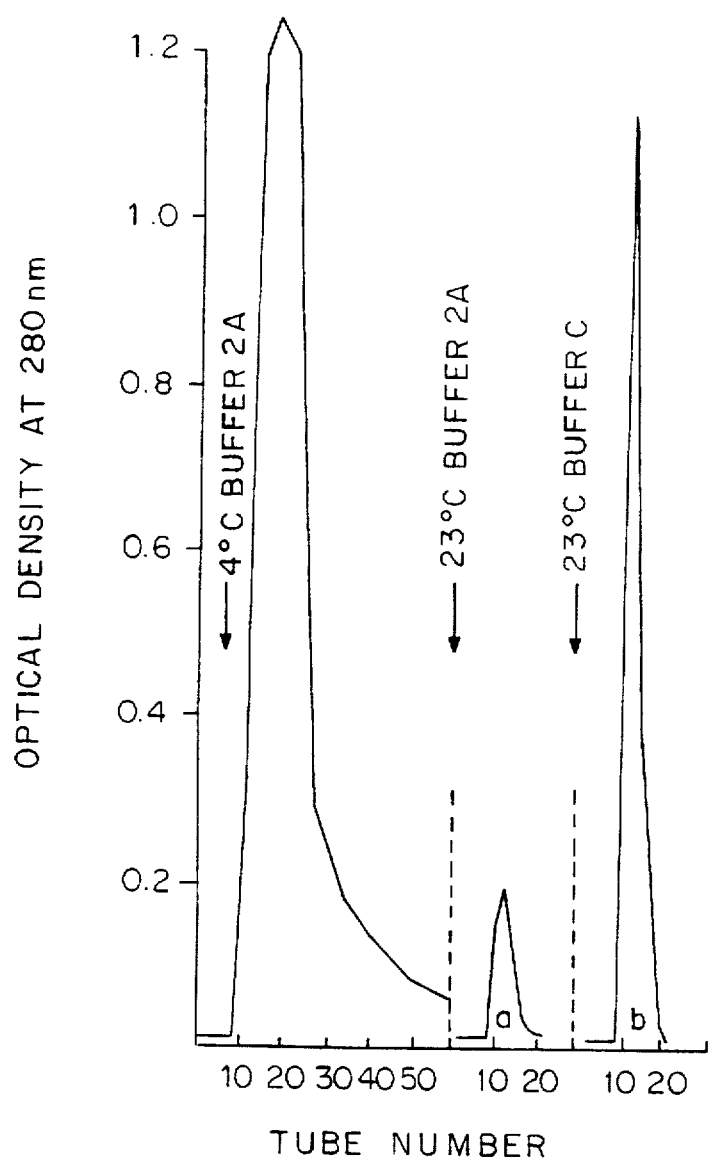
FIG. 3 is a graph showing the purification of fibrin-binding peptides, derived from fibronectin, by affinity chromatography on a fibrin-SEPHAROSET™ column; an SDS-PAGE gel pattern, not shown, indicates that the fibrin-binding peptides eluted from the affinity column had in this example molecular masses of 25 kDa (peak a) and 11 kDa (peak b).

The effluent unbound fraction of digested Fn from the gelatin-SEPHAROSE™ affinity chromatography was combined with a fibrin-SEPHAROSE™ affinity matrix (80 mg/15 ml beads) in a batchwise manner, incubated overnight at 4° C. with end over rotation, poured into a column, and washed with equilibration buffer (fibrin-binding buffer (FBB), 0.05M Tris-HCl, 0.1M NaCl buffer, pH 7.6). Upon warming the column to room temperature, a 25.9 kDa fragment was eluted with FBB (Peak a, FIG. 3). Under these conditions, a portion of the 25.9 kDa fragment remained bound to the fibrin-SEPHAROSE™ and was recovered from the affinity matrix together with an 11 kDa fragment that was considered to have higher fibrin-binding affinity because it required denaturing conditions for elution (0.05M tris, 6.0M urea, 0.1M NaCl, ph 7.6) (FIG. 3, Peak b). For amino acid analysis and amino acid sequencing, the 25.9 kDa fragment was further purified by heparin affinity chromatography. The 25.9 kDa fragment was previously shown to possess heparin-binding activity of "intermediate" affinity (Baron, et al. (1990) Protein Production in Biotechnology (T. J. R. Harris, Ed.), pp 49–60, Elsevier, London). The 25.9 kDa fragment eluted with 0.25M NaCl using a gradient from 0. 1.0M NaCl in 0.05M tris buffer, pH 8.0. The yield of the 11 kDa fragment from the intact molecule was approximately 5% (w/w). This is the same as the theoretical yield. The extinction coefficient has been determined to be approximately 4.5, based on a comparison between $A_{280}$ and protein concentration determination by Coomassie Protein Assay (Pierce Chemical Co.).

Thus, the binding of the 25.9 kDa fragment appeared to be of lower affinity because it was eluted from the column by a change in temperature. The affinity of the 11 kDa fragment for fibrin was markedly higher, since it required denaturing conditions (6M urea or 50% ethylene glycol) for its elution from the fibrin affinity matrix.

To obtain smaller fragments of fibronectin that retain fibrin-binding activity, the 11 kDa fragment can be further digested with a variety of enzymes, e.g., plasmin (Sigma), generated by urokinase (American Diagnostica) digestion of plasminogen, Staphylococcal V8 (Sigma), Endoproteinase Lys-C and Endoproteinase Asp-N (Boehringer-Mannheim).

To test for fibrin-binding activity, the digested 11 kDa protein is subjected to fibrin-SEPHAROSE™ chromatography (as described herein) or employed in the ELISA described below to competitively inhibit either the 11 kDa fragment or intact fibronectin from binding to fibrin on microtiter plates. The smaller fragment may also be directly bound to the ELISA plate using an appropriate method of detection (e.g., an antibody).

Fibrin-binding fragment(s) can require further purification by HPLC. The amino acid sequence can be obtained by electroblotting a fragment that binds to fibrin, by the method of Matsudaira et al., *J. Biol. Chem.* 262:10035 (1987) followed by N-terminal by amino acid sequencing; this will allow identification of its location within the intact fibronectin molecule.

EXAMPLE II

SDS-PAGE Analysis of the Purified 11 kDa Fibrin-Binding Peptide

The concentration of acrylamide monomer was 14% in the SDS-PAGE gel. 15 µg of 11 kDa fibrin-binding peptide, either reduced or unreduced, dissolved in sample buffer, was passed into the gel. The molecular weight (molecular mass) of 11 kDa was determined by comparison with cytochrome c, which has a molecular mass of 12.7 kDa. The unreduced 11 kDa peptide was shown to contain higher molecular weight material that was reduced to 11 kDa by dithiothreitol. It is therefore reasoned that the high molecular weight material represents disulfide bonded multimers of the 11 kDa peptide and that this peptide can be at least 96% purified by a one step chromatographic procedure through fibrin-SEPHAROSE™.

EXAMPLE III

Figure 5B:
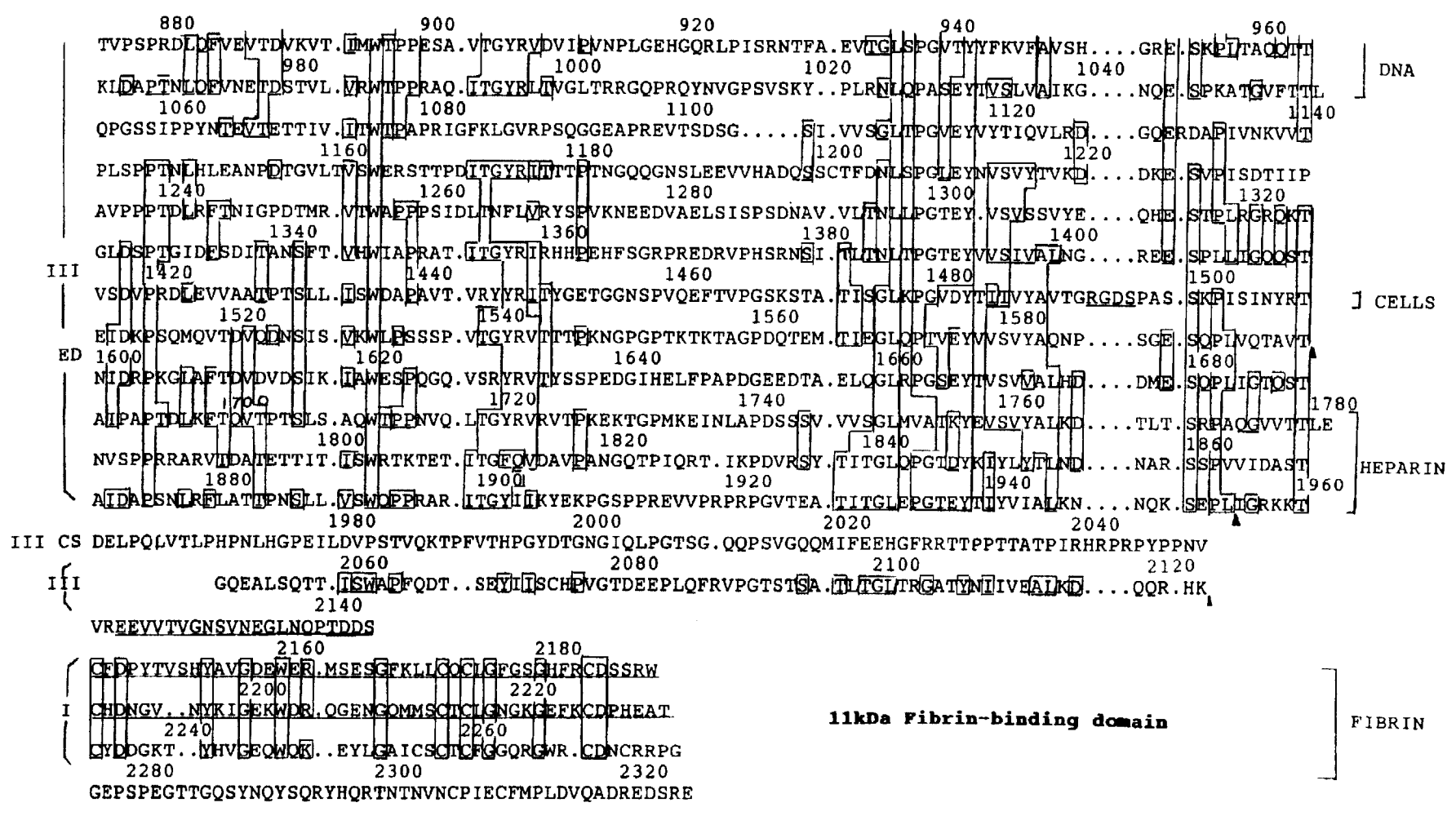

Amino Acid Sequences and Localization of the Fibrin-Binding Peptides Within the Fibronectin Molecule The entire amino acid sequence of fibronectin has been deduced from the cDNA and is presented in FIG. 5 as a contiguous sequence, albeit grouped and aligned by domains and modules (Kornblihtt, et al. *EMBO, J.* 4:1755–1759 (1985)).

Figure 4A:
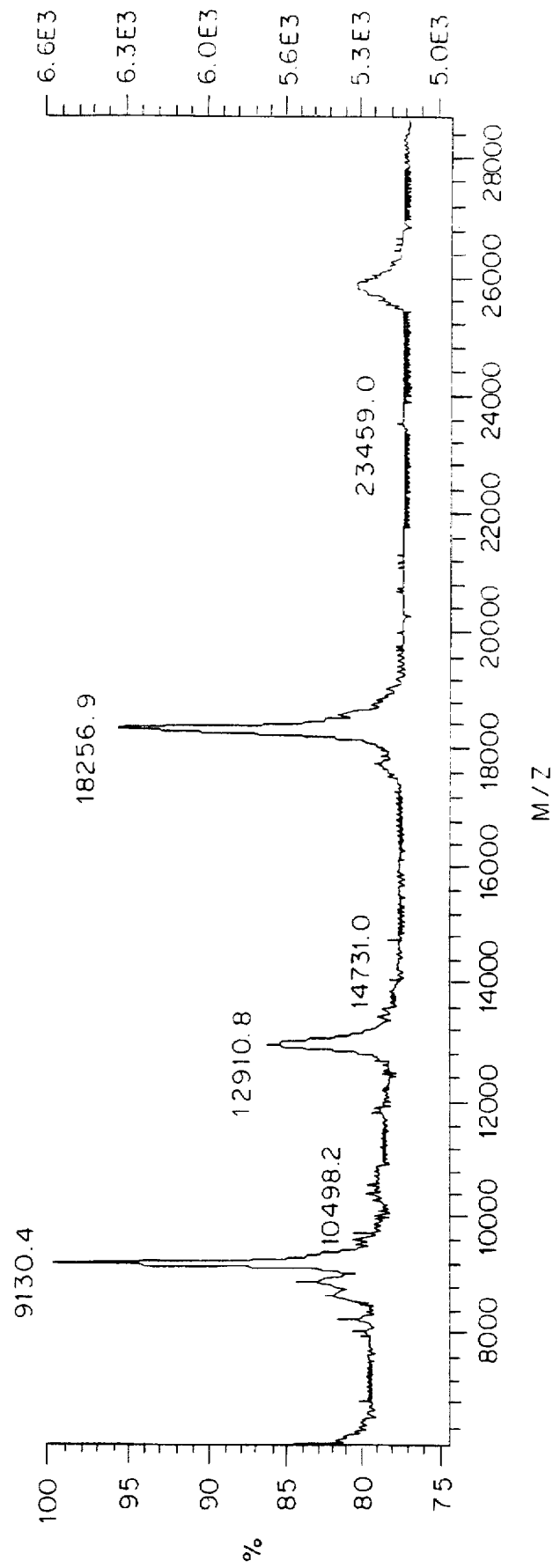
FIGS. 4A and 4B are graphs showing the laser desorption mass spectrometry profile of the N-terminal fibrin-binding peptide from fibronectin obtained on a VG Analytical Tof-Spec instrument. Also shown are the doubly-charged species (peaks) corresponding to β-lactoglobulin that was employed as an internal standard.
Figure 4B:
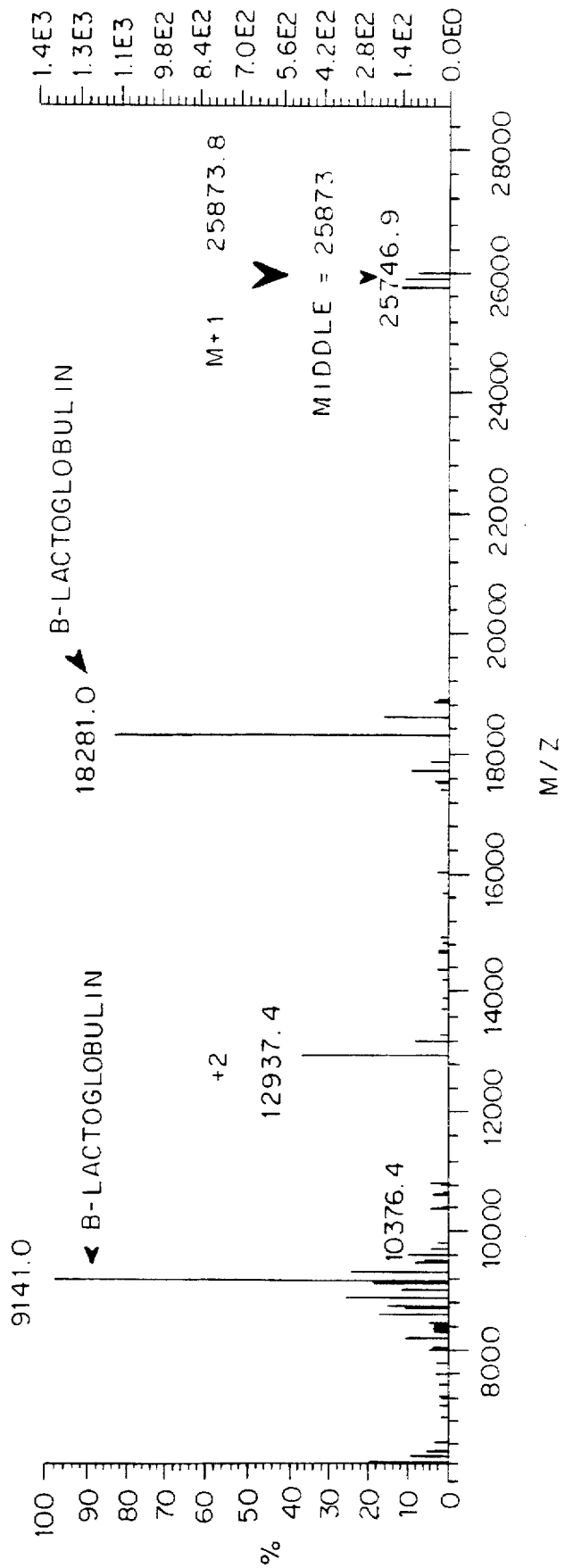

Following fibrin-SEPHAROSE™ affinity chromatography, the 25.9 kDa peptide was further purified by high pressure liquid chromatography. The molecular mass of the $NH_2$-terminal fibrin-binding fragment derived by proteolysis of the Fn molecule was determined using laser desorption mass spectrometry (LDMS) (FIG. 4). Following dilution of a lyophylized purified fragment in water, 2 picomoles were applied to a α-Cyano-4-hydroxycinnamic acid matrix. The LDMS was performed on a VG Analytical instrument (Fison Instruments, Manchester, UK) with 10 picomoles of β-lactoglobulin added as an internal standard. The mass calculation, performed on the doubley-charged unknown species revealed that the $NH_2$-terminal FBP from fibronectin was 25,875 Da. The COOH-terminal residue of the fragment was deduced by comparing the observed mass with theoretical masses of fragments extending from the known $NH_2$-terminal residue, determined as described below. Theoretical mass values were determined using General Protein Mass Analysis/Windows (GPMAW).

N-terminal amino acid sequencing.

The N-terminal amino acid sequence of the 25.9 kDa FBP was determined after electroblot onto polyvinylidene diflouride (PVDF) membranes on a 477A Protein Sequencer equipped with an on-line 120A PTH analyzer (Applied Biosystems) (Method: Matsudaira et al. *J. Biol. Chem.* 762:10035 (1987)). The 25.9 kDa FBP commences at amino acid 17 from the N-terminus of the mature Fn. Using a computer program that calculates molecular masses from specified amino acid sequences (GPMAW) together with the N-terminal amino acid sequencing, it was possible to deduce that the fragment corresponds to residues Ser17 to Gln$^{246}$.

A "magnified" version of the 11 kDa fibrin-binding peptide from the C-terminal of the fibronectin molecule is presented in FIG. 6 (SEQ ID NO:1).

Based on the structural features of fibronectin, it was concluded that both the 25.9 kDa and 11 kDa fibrin-binding peptides contained consensus sequences of a type I repeat module.

During the course of isolation of the 11 kDa fibrin-binding peptide, it was noted that elution from the affinity matrix with 6.0M urea partially destroyed the fibrin-binding activity. Thus, although 100% of the 11 kDa peptide that was applied to the column could be eluted, only 40–50% of the protein rebound to a second fibrin column at 4° C., and only 20% bound at 37° C.

Since complete recovery of fibrin-binding activity was desired for use of the molecule in clinical application, various buffers were tested in an attempt to optimize recovery of the peptide while retaining maximal biological activity.

Table III summarizes the results and lists the buffers used in these experiments. It was found that a solution of 50% ethylene glycol performed optimally in eluting the 11 kDa peptide from fibrin-SEPHAROSE™. It should be noted here that both extreme and subtle changes in pH and salt concentration did not disrupt the binding to fibrin.

TABLE III

ELUTION OF 11 kDa FIBRIN-BINDING FRAGMENT WITH VARIOUS AGENTS

| AGENT | % ELUTED |
| --- | --- |
| 1.0M KBr | 55–65 |
| 1.0M Arginine | 26 |
| 50% ethylene glycol, pH 11.5 | 77 |
| 2.0M Urea | 32 |
| 4.0M Urea | 50–60 |
| 6.0M Urea | 100 |

(All samples were rotated in the cold overnight)
REBINDING OF ELUTED 11 kDa FRAGMENT TO FIBRIN

| BUFFER | % Rebound at: | |
| --- | --- | --- |
|  | 37° C. | 4° C. |
| Ethylene glycol | 49.5* | 80 |
| 2.0M Urea | ND | 60 |
| 4.0M Urea | ND | 45–52 |
| 6.0M Urea | ND | 40–50 |
| 6.0M Urea (step dialysis) | ND | 40–50 |
| 1.0M KBr | ND | 7–10 |
| 1.0M Arginine | ND | ND |

*At 37° C., 4–5% of the applied material bound to a fibrinogen-SEPHAROSE ™ column (ethylene glycol)

EXAMPLE IV

Expression of Fibronectin Type I Modules

The expression in yeast (*Saccharomyces cerevisiae*) and the purification of the seventh type 1 module of human fibronectin (⁷F1) was described by the present inventors (Baron, M. et al., In: *Protein Production in Biotechnology*, Harris (ed), pp 49–60, Elsevier, London, 1990)). A phosphoglycerate kinase promoter (Mellor et al., *Gene* 24:1–14 (1983); Kingsman et al., *Biotech. Genet Eng. Rev.* 3:377–416 (1985)) and the α-factor leader sequence (Kurjan et al., *Cell* 30:933–943 (1982); Brake et al., *Proc. Natl. Acad. Sci. USA* 81:4642–4646 (1984)) were used to direct the expressed protein into the culture medium. The expressed module corresponded to amino acids 431–478 (Owens et al., *EMBO J.* 5:2825–2830 (1986)) (referred to here as residues 1–48) and included all the type 1 consensus sequence and the linker connecting this module to the preceding type 2 repeat.

a.) Construction of expression vectors

The molecular cloning strategies were used to produce DNA sequences (inserts) corresponding to the relevant type 1 domains are described below:

(1) The insert required for expression of the ⁷F1 module was isolated from the cloned human fibronectin gene as a NcoI/NsiI restriction fragment.

Figure 13:
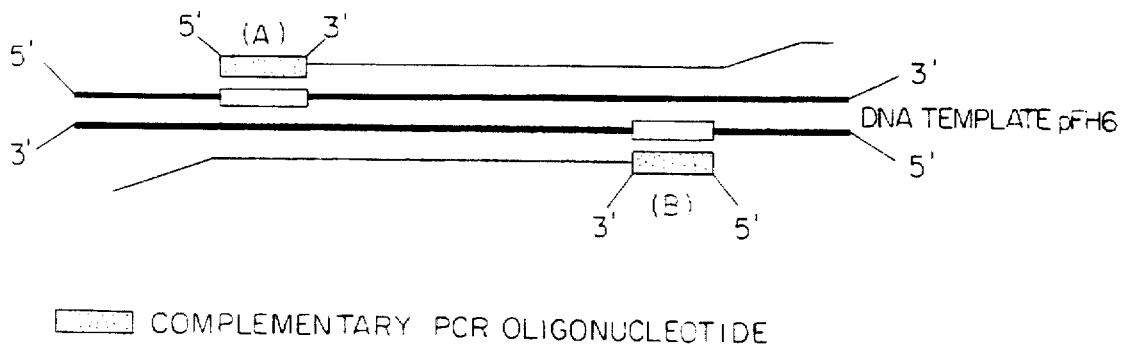
FIG. 13 illustrates aspects of the synthesis of DNA inserts by PCR. Two synthetically prepared oligonucleotides ((A) and (B)), complementary to a cloned fragment of the human fibronectin gene were used in a standard PCR reaction: DNA melting, 1 min at 92° C.; single strand annealing, 1 min at 56° C.; extension, 3 min at 72° C. This cycle was repeated 25 times. The oligonucleotides for the $^4F1.^5F1$ DNA insert are shown. Oligonucleotide A (SEQ ID NO:2) corresponds to the N-terminus of the domain, giving a blunt end. Oligonucleotide B (SEQ ID NO:3) corresponds to the C-terminus, with a stop codon followed by a BamHI site and a short 5' tail to aid enzymatic cleavage by restriction endonucleases.
Figure 20:
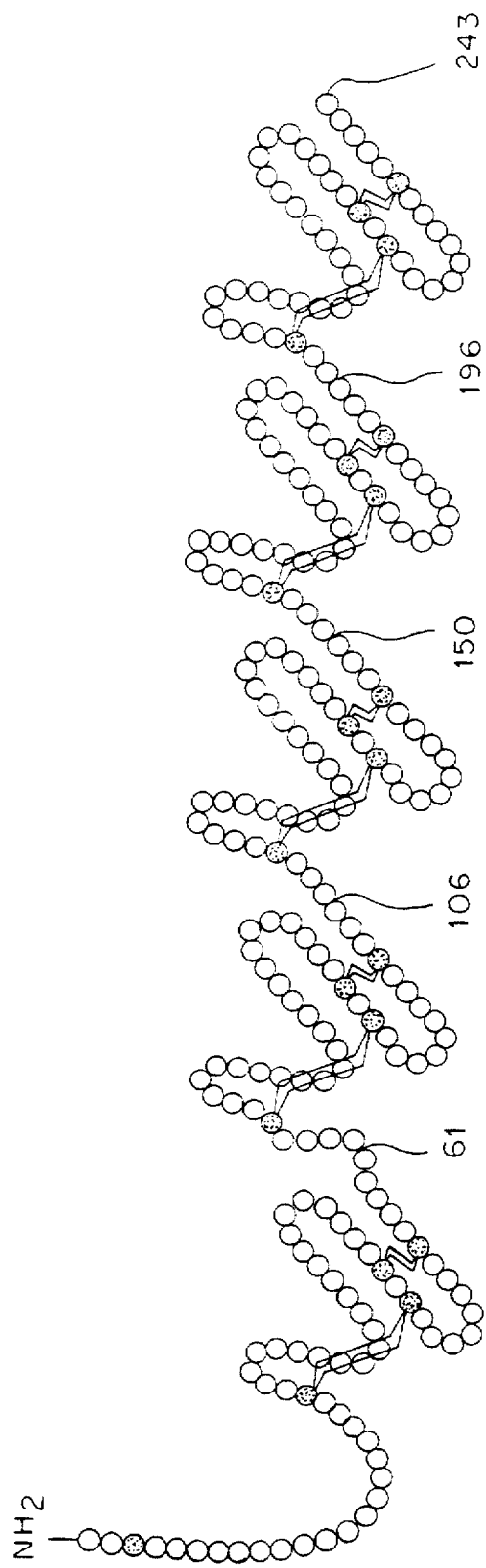
FIG. 20 is a schematic illustration of the N-terminal fibrin-binding domain of fibronectin, showing the finger-like structure and the location of the various modules and module pairs. Module $^1$F1: amino acids 1–61; Module pair $^1$F1.$^2$F1: amino acids 1–106; module pair $^4$F1.$^5$F1: amino acids 150–243 or to 250 (including linker). The amino acid numbers refer to those of SEQ ID NO:1.

(2) For both module pairs (¹F1.²F1 and ⁴F1.⁵F1) (see FIGS. 19 and 20) and module (¹F1), inserts were synthesized by the polymerase chain reaction (PCR), using a cloned fibronectin gene template and synthetically prepared oligonucleotide primers (FIG. 13).

Figure 14:
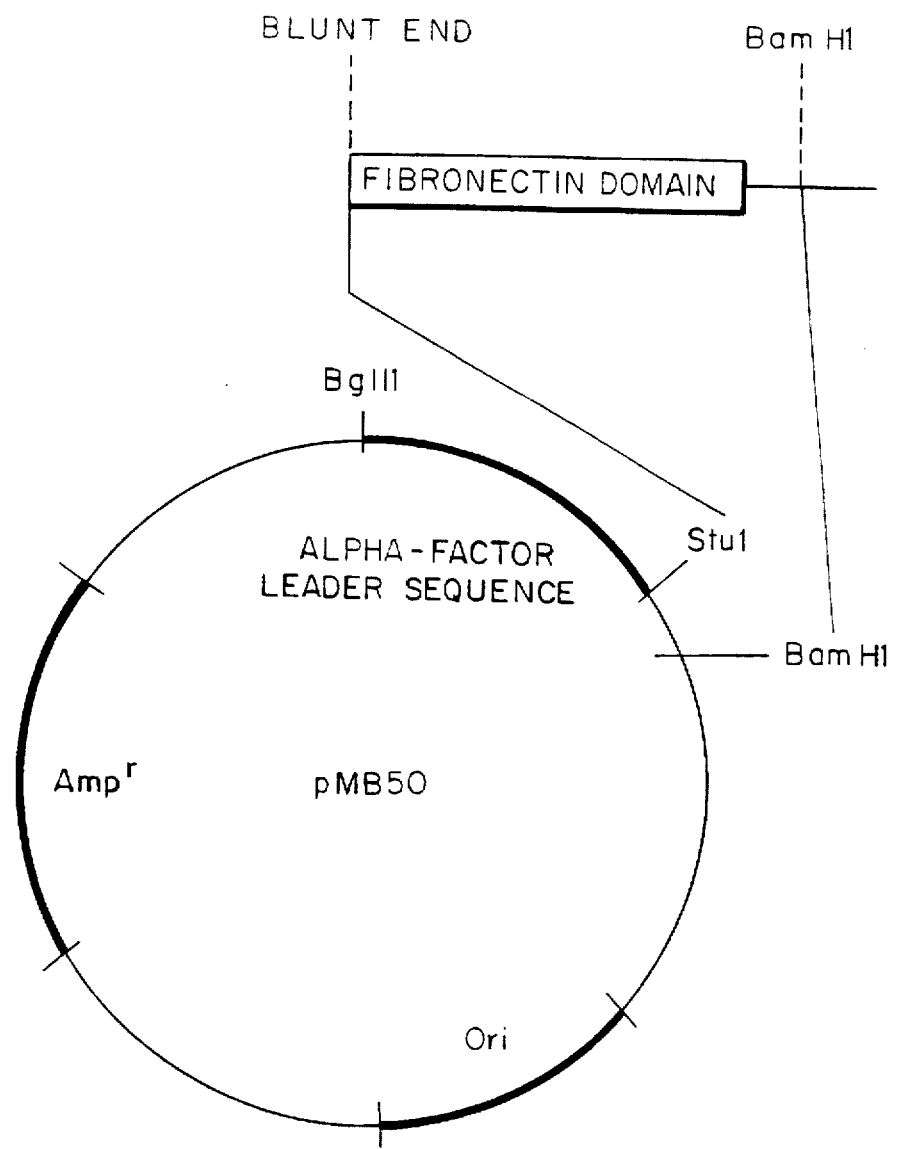
FIG. 14 is a schematic diagram of the pMB50 *E. coli* vector. The fibronectin DNA insert is ligated between the StuI and BamHI sites. The StuI site links the insert and the leader sequence and the ampicillin resistance gene is used to select the positive *E. coli* transformants.

(3) A plasmid designated pMB50 was constructed by cloning the yeast alpha factor leader sequence into the polylinker of the SP46 vector (Promega Biotechnology) with convenient restriction sites allowing the various DNA inserts to be fused, in-phase with the leader sequence (Baron et al., In: *Protein Production in Biotechnology*, Harris TJR (ed), Elsevier, London, pp 49–60, 1990) (FIG. 14). Ampicillin resistance was used to select for positive *E. coli* transformants and the fidelity of the insert sequences were confirmed by sequencing. After this, the entire leader/fibronectin constructs were removed as BglII/BamHI fragments and ligated into the yeast expression vector, pMA91 (FIG. 15) (Mellor et al., *Gene* 24:1–14 (1983)). These vectors were transformed into a leucine(−) yeast strain and recombinants selected by their ability to grow on medium lacking leucine.

Module expression and purification The various type 1 modules were expressed as fusion peptides with the leader sequence (FIG. 16). The leader sequence directs secretion and in the process is cleaved off, leaving the authentic fibronectin peptide in the external media. Yields of approximately 0.5–1 mg/l were common.

The secreted fibronectin peptides, along with irrelevant yeast proteins and media derived molecules were concentrated by batch absorption to C18 silica beads, present during yeast growth. In each case the crude material was eluted from the beads with 50% acetonitrile, freeze dried and purified by reverse phase HPLC.

Figure 22:
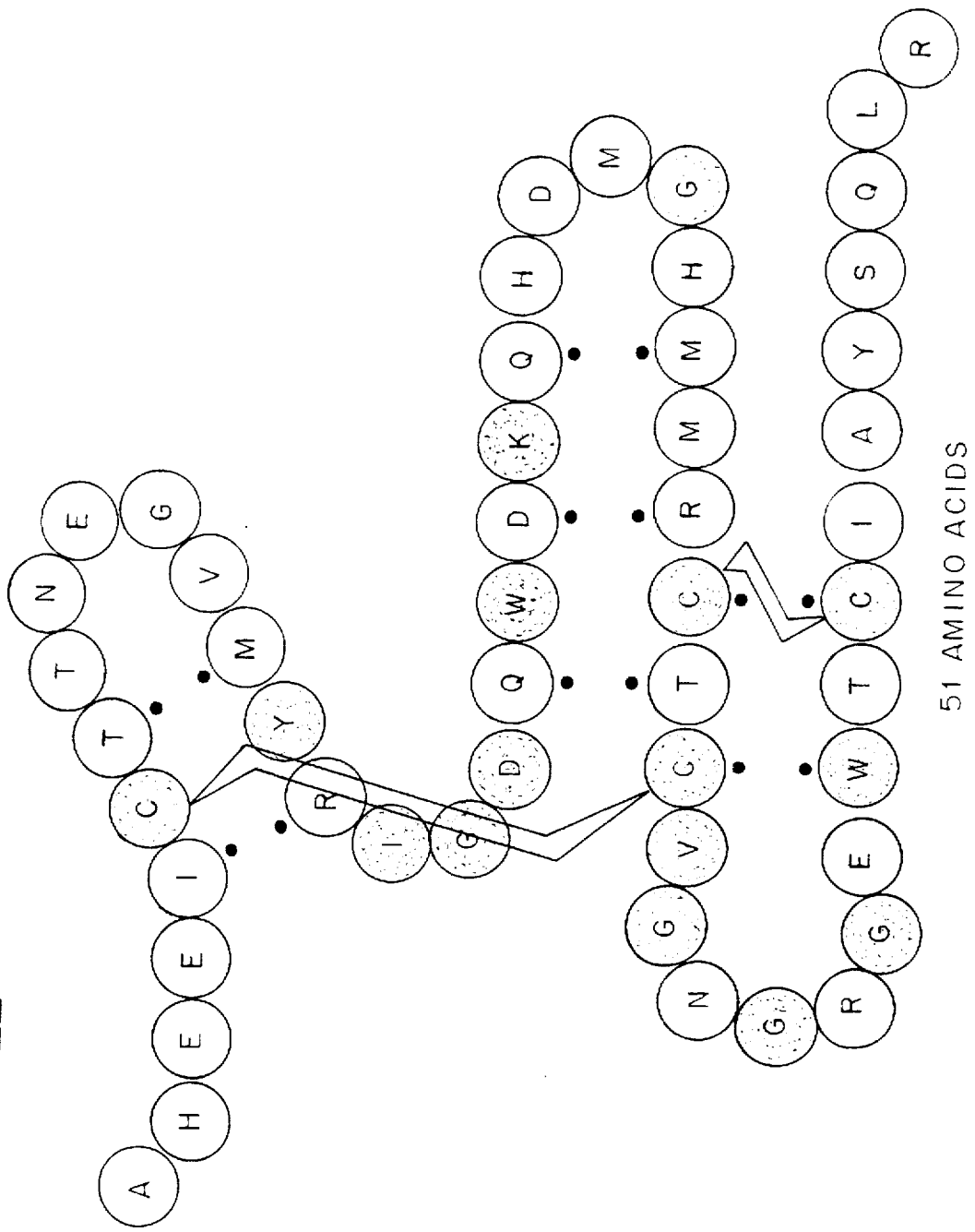
FIG. 22 shows a model of the secondary structure of the 51 amino acid seventh type 1 module from human fibronectin (fibronectin module $^7$F1) (residues 434–484 of SEQ ID NO:1). Shaded residue are highly conserved in aligned sequences or show predominantly conservative replacements.

For the first peptide to be studied (⁷F1) (see FIG. 22), it was necessary to use SDS-PAGE, amino acid analysis and N-terminal sequencing to show that the protein had been correctly processed from the leader sequence. In order to confirm correct folding, the disulfide bonding pattern was ascertained. However, having determined the NMR characteristics of this type 1 consensus structure (see below), it was then adequate to use SDS-PAGE and mass spectroscopy to analyze peptide primary sequence and a comparison of basic NMR characteristics to confirm consensus folding of other purified type 1 domains.

An expressed module corresponded to amino acids 431–478 (Owens et al., *EMBO J.* 5:2835–2830 (1986)) (referred to here as the ⁷F1) and included all the type 1 consensus sequence and the linker connecting this module to the preceding type 2 repeat.

DNA sequences corresponding to a type I repeat module of fibronectin were synthesized and amplified by the polymerase chain reaction (PCR), well-known steps in the art, using synthetically prepared oligonucleotides. The DNA inserts are subsequently ligated into the pMB50 plasmid to be in phase with the yeast (Saccharomyces cerevisiae) alpha-factor leader sequence. FIG. 14 illustrates the construction of the pMB50 vector. The pMB50 consists of a BamHI/BglIII fragment containing the alpha-factor leader sequence, inserted into the polylinker sequence of SP46. Ampicillin resistance is used to select the *E. coli* positive clones.

The insert (after PCR) is ligated between the StuI/Bam1 sites in the *E. coli* vector pmB50 (FIG. 15). The fibronectin inserts are sequenced prior to the removal of the entire leader/fibronectin construct for ligation into the yeast expression vector, pMA91 (FIG. 15). The pMA91 expression vector carrying the fibronectin construct is transformed into a leucine(−) strain of yeast such that successfully transformed yeast are able to grow on leucine (−) media. The peptides are secreted into the media by the alpha-factor secretion system driven by the phosphoglycerate kinase promoter. The leader sequence is cleaved from the peptide during secretion. Low concentrations of irrelevant yeast proteins are secreted into the media. Nevertheless, the fibronectin peptide is alternatively purified by HPLC.

SDS-PAGE and mass spectroscopy were used to analyze the secreted fibronectin module. NMR is used to confirm proper folding of the molecule. Methods for these procedures are described by Baron et al., supra; Mellor et al., *Gene*, 24, 1–14 (1983); and Kurjan et al., *Cell*, 30, 933–943 (1982).

b.) Construction, expression and purification of recombinant fibronectin modules ¹F1, ¹F1.²F1, and ¹⁰F1.

¹F1, ¹F1.²F2, and ¹⁰F1 were also expressed from a system based on the yeast α-factor secretion pathway. DNA fragments encoding ¹F1 and ¹F1.²F1 were amplified by the polymerase chain reaction (PCR) from a cloned fragment of human Fn cDNA. The sense strand oligonucleotide primer, which encoded the NH₂-terminal segment of both proteins, had the sequence 5'-CAG GCT CAG CAA ATG GTT CA (SEQ ID NO:6). While the anti-sense strand oligonucleotide primer for ¹F1 had the sequence 5'-T AAT GGA TCC TTA TTC AGG TTT ACT TTC GCA GTT A (SEQ ID NO:7), and for ¹F1.²F1 was 5'-T AAT GGA TCC TTA TGC GAT GGT ACA GCT (SEQ ID NO:8). The anti-sense oligonucleotides encoded the COOH-terminus of both proteins, followed by a stop codon, a BamH1 site (GGATTC) and a four nucleotide tail. Type 1 modules are typically encoded on single exons (¹²F1 is encoded by 2 exons) bordered by phase 1 introns, Patel et al, *EMBO J.* 6:2565–2572, 1987). Therefore, both PCR fragments were designed to encode from the 5'-intron at the NH₂-terminus of ¹F1 (located between the C and G nucleotides of the sense strand oligonucleotide), and as far as the last complete codon of the exon encoding either the first or second type 1 modules. Vector construction, expression and purification of ¹F1 and ¹F1.²F1 were performed as previously described for ⁴F1.⁵F1 (Williams, M. J. et al., *Biochemistry* 32:7388–7395, 1993). We observed a discrepancy in the DNA sequences of the ¹F1 and ¹F1.²F1 clones compared to the published sequence of human Fn (Kornbliht, A. R. et al., *EMBO J.* 4:1755–1759, 1985), corresponding to the substitution of Val42 for an alanine. We have re-sequenced part of the same pHF6 Fn clone used to obtain the original cDNA sequence of this region of Fn, and found that the codon for residue 42 does indeed encode an alanine residue. The expression plasmids were constructed from the vector pMA91 containing the non-inducible phosphoglycerate kinase (PGK) promoter to direct expression (Mellor, J. et al., *Gene* 24:1–14, 1983).

The $^{10}$F1 expression plasmid was constructed using the pSW6 vector with a galactose inducible promoter (Pascal, J. C. et al, *J. Mol. Endocrinol.*, 6:63–70, 1991). In this case, the DNA fragment was amplified using a sense strand oligo-nucleotide primer with the sequence 5'-T CAG TTA AGC TTG GAC AAA AGA GAT GAC TCG TGC TTT GAC CC (SEQ ID NO:9) and an anti-sense strand primer with the sequence 5'-T TCA GTT GGA TCC TTA AGA TGA ATC ACA TCT GAA ATG AC (SEQ ID NO:10). The sense strand primer encoded a HindIII site (AAG CTT), followed by six nucleotides from the α-factor leader and 20 nucleotides encoding from the N-terminus of the $^{10}$F1. Six nucleotides were included upstream of the HindIII site to aid restriction. The anti-sense primer encoded as far as the last complete codon of the exon encoding the module, followed by a TTA stop codon, a Bam HI site and six extra nucleotides. After BamH1/HindIII digestion, the DNA fragment was ligated directly into the single BglII site of the pSW6 yeast expression vector, downstream and in phase with the α-factor leader sequence. This negated the requirement for the subcloning step used for the pMA91 expression vector construction. Competent yeast cells (*Saccharomyces cervisae* MC2) were transformed with pSW6-$^{10}$F1 and selected by their ability to grow on leucine-minus medium (Pascal, J. C. et al., *J. Mol. Endocrinol.* 6:63–70, 1991). Cultures (1L) were grown to a high density in baffled flasks for 60 hours at 30° C., using media prepared with 0.17% (w/v) yeast nitrogen base (without amino acids or ammonium sulfate), 0.5% ammonium sulfate, 2% glucose, and an amino acid cocktail including uracil and lacking leucine (YNB2 medium). The cells were centrifuged and each pellet was resuspended in 5 ml YNB2 and used to inoculate individual baffled flasks containing 1 L of YNB2 induction media, supplemented with 1% galactose and no glucose. The cultures were shaken for 48 hours, before the recombinant $^{10}$F1 was isolated from the supernatant as previously described (Williams, M. J. et al, *Biochem.* 32:7388–7395, 1993). The protein was purified by anion exchange HPLC using a gradient from 0 to 0.75M NaCl in 0.01M Tris, pH 7.5, subsequently dialyzed, and further subjected to a single separation by reverse phase HPLC using a C8 column. (The recombinant proteins were eluted as follows: $^{10}$F1 at 0.4M NaCl from anion exchange and 36% acetonitrile [CH$_3$CN] from C8; $^1$F1 at 30% CH$_3$CN; $^1$F1.$^2$F1 at 33% CH$_3$CN; and $^4$F1.$^5$F1 at 28% CH$_3$CN). The primary structure and purity of each protein was confirmed by Electrospray mass spectrometry (ESMS) as described. The molecular mass of each recombinant protein was determined by the software General Protein Mass Analysis for Windows (GPMAW). The following values were obtained: $^1$F1, 6.8 kDa; $^1$F1.$^2$F1, 11.9 kDa; $^7$F1, 5.5 kDa; $^{10}$F1, 5.2 kDa, $^4$F1.$^5$F1, 10.51 KDa.

TABLE IV

Physicochemical Characteristics of recombinant type 1 modules and proteolytic fragments of fibronectin*

| Protein | Molecular mass (Daltons) | $E_{280}$ (M−1 cm−1) |
|---|---|---|
| 1F1 | 6,807.5 | 11,290 |
| 1F1.2F1 | 11,941.0 | 21,300 |
| 4F1.5F1 | 10,510.0 | 27,560 |
| 7F1 | 5,496.0 | 13,140 |

TABLE IV-continued

Physicochemical Characteristics of recombinant type 1 modules and proteolytic fragments of fibronectin*

| Protein | Molecular mass (Daltons) | $E_{280}$ (M−1 cm−1) |
|---|---|---|
| 10F1 | 5,166.6 | 8,730 |
| 25.9 kDa N-terminal proteolytic fragment | 25,870.0 | 63,280 |

*Estimate based on amino acid sequence, mass spectrometry and computer analysis by General Protein Mass Analysis/Windows The $^1$F1.$^2$F1 module pair and the $^1$F1 module were isolated as single homogeneous peaks be reverse phase HPLC. However, results from electrospray mass spectometry (ESMS) indicated the presence of two similar species in each case. The minor species in both samples corresponded to a protein of the expected mass, after post-transcriptional modification of the NH$_2$-terminal glutamine residue to a pyroglutamate. It should be noted that the mature Fn also has an N-terminal pyroglutamate (McDonagh, R. P. et al., *Febs. Lett.* 127:174–178, 1981). However, the mass of the major species indicated that the NH$_2$-terminal Gln-Ala dipeptide had been cleaved away and the new NH$_2$-terminal Gln residue has in turn been modified to a pyroglutamate. Presumably, this post-transcriptional event was catalyzed by the native yeast STE13 gene encoded dipeptidyl aminopeptidase, known to be involved in the removal of Glu-Ala and Asp-Ala dipeptides from the NH$_2$-terminus of the α-factor mating pheromone precurose (Zsebo, K. M. et al., *J. Biol. Chem.*, 261:5858–5865, 1986). Attempts to separate the two species for both $^1$F1 and $^1$F1.$^2$F1 proved unsuccessful. However, this staggered NH$_2$-terminus is distant from the beginning of the first type 1 module consensus sequence (approximately 18 residues) and therefore, should not have an effect on the integrity of the module itself. Indeed, preliminary NMR studies of $^1$F1 and $^1$F1.$^2$F1 confirmed that both these proteins are homogeneously folded with predominantly β-sheet structure, as predicted from the type 1 "consensus" structure.

EXAMPLE V

NMR Structure Determination of the Type 1 Module

The three dimensional structure of the type 1 module has been described (Baron, M. et al. *Nature* 345:642–646 (1990) ), which reference is hereby incorporated by reference in its entirety (FIGS. 17–24).

NMR spectra were collected on Bruker 600 MHz and 500 MHz spectrometers in both D$_2$O and H$_2$O at temperatures of 27° C. and 39° C. at pH 7.6 (uncorrected meter reading in D$_2$O). Two-dimensional NMR experiments were performed using standard Bruker microprograms; 64 scans collected with 512 increments and 4,096 data points. NOESY spectra were recorded with mixing times of 100–300 ms. This spectrum was recorded with a mixing time of 300 ms, at a temperature of 27° C.; the protein concentration was 5 mM in 20 mM sodium phosphate buffer (pH 7.6).

Figure 17B:
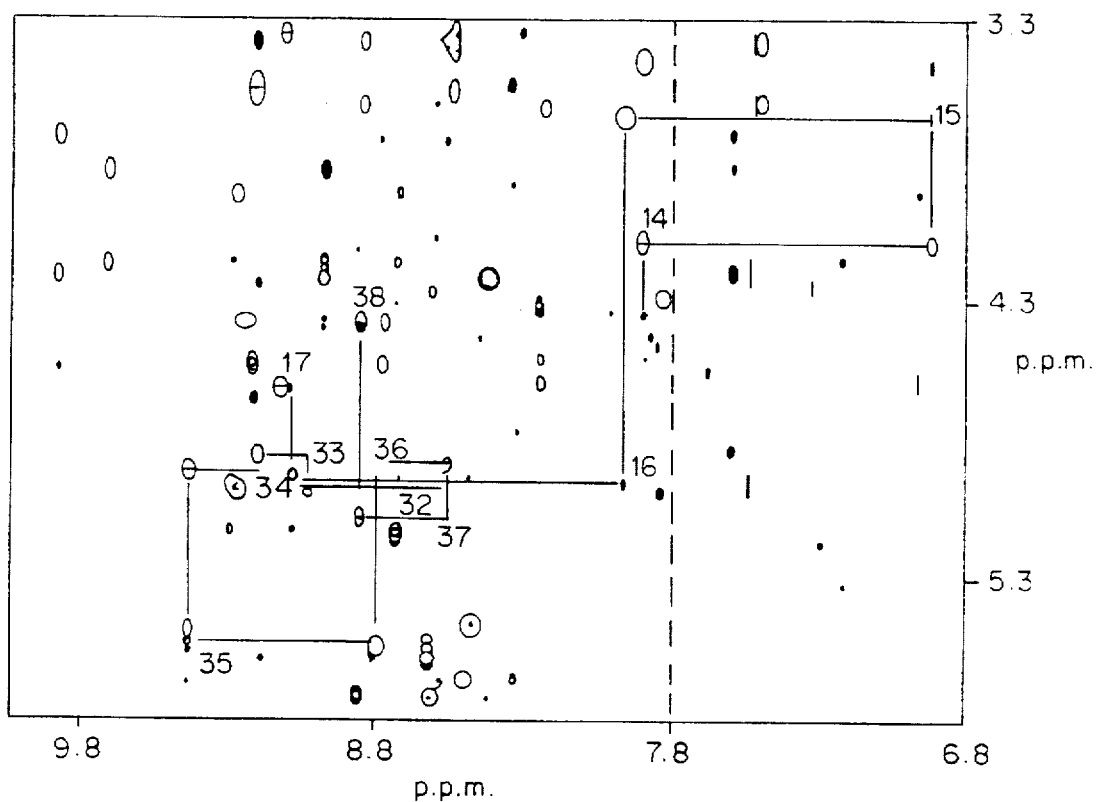
FIGS. 17A-B present nuclear magnetic resonance (NMR) data, more specifically: 17A shows the region of a nuclear Overhauser enhancement spectroscopy (NOESY) spectrum showing nuclear Overhauser effects (NOE) from backbone amide protons. The solid and dotted lines illustrate the sequential assignment of two regions of the module (we refer to the residues in the expressed module as 1-48, 430 must be added to obtain the numbering of intact fibronectin). Intra-residue HNi-HCαi NOEs are labelled. Vertical and horizontal lines connect these to unlabeled peaks which are sequential HN(i+1)–HCα(i) NOEs. 17B presents a diagonal plot of the NOE distance constraints used for the generation and refinement of the fibronectin module 7 structures. The filled squares represent pairs of residues connected by at least one distance restraint. The solid squares indicate restraints involving only side-chain atoms and the hatched squares indicate restraints involving at least one backbone atom.
Figure 17A:
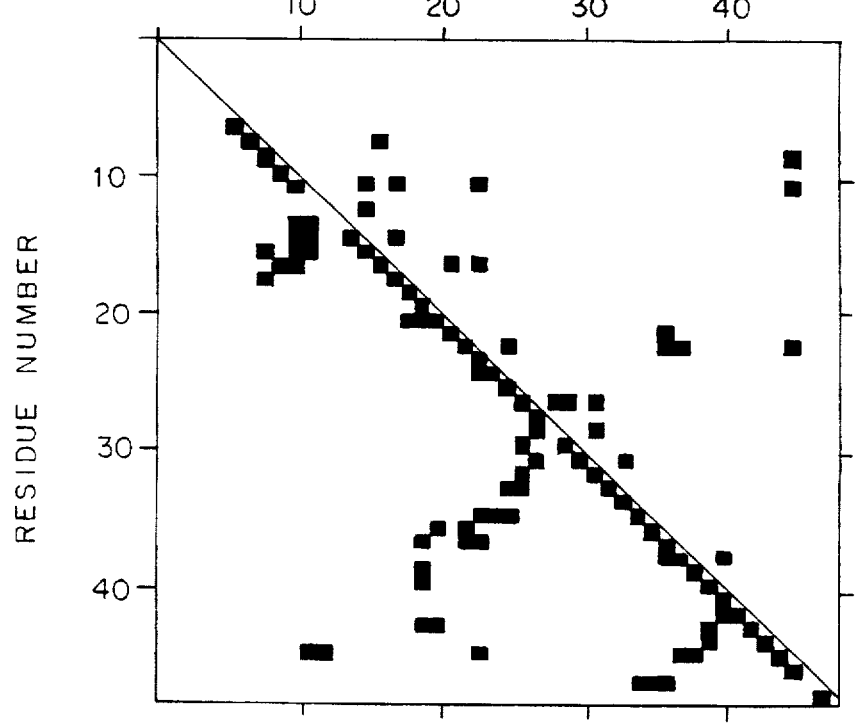

In preliminary NMR investigations, a substantial conformational change was observed when the protein was titrated below pH 7.0, and it was therefore necessary to work close to a physiological pH. In spite of the non-optimum pH (lower pH is usually used to slow the exchange rate of amide protons with the solvent), 42 out of the 48 backbone amide protons were identified. FIG. 12A is a region of a NOESY (nuclear Overhauser enhancement spectroscopy) spectrum recorded in water at pH 7.6 showing nuclear Overhauser effects (NOEs) between the backbone amides and the alpha protons (through-space connectivities); 144 NOEs were short range (>i,i+4), allowing virtually complete sequence-specific assignment of the protein (two sections of sequential assignment are highlighted in FIG. 17A). A further 104 NOEs were long range (>i,i+4), and the distribution of both long and short range NOEs is shown in FIG. 17B.

To calculate the three-dimensional structure, a combination of distance geometry followed by restrained molecular dynamics was used. The experimental input consisted of distance constraints derived from the observed NOEs.

For overlay structure, refinement was carried out with the inclusion of 381 experimentally determined distance restraints. The two disulfide bonds were also included. After preliminary calculations, 23 additional distances restraints were added to define hydrogen bonds predicted from the identified β-sheet secondary structure (those that were flanked residues for which HCα—HCα NOES were observed, FIG. 18B). The hydrogen bond restraints were removed during the restrained molecular dynamics stage. NOEs were classified as strong (0.18–0.27 nm), medium (0.18–0.33 nm), and weak (0.18–0.5 nm) by measuring peak volumes in spectra recorded with mixing times of 100, 200 and 300 ms. Distances were calibrated to make the range of observed NOE intensities internally consistent. Initial structures were generated within the program DSPACE (Doolittle, *Trends Biochen. Sci.* 10:233–237 (1985)) by distance geometry (e.g., similarly as in Havel et al., *Bull. Math. Biol.* 45:665-720 (1983); Havel et al., *J. Theor. Biol.* 104:383–400 (1983); Crippen *J. Comput. Biol* 24:96–104 (1977)). Ten embedded structures were generated and then refined interactively (e.g., similarly as in Weber et al., *J. Molec. Biol.* 204:483–487 (1988)) within DSPACE using a combination of conjugate gradient minimization, coordinate randomization, and simulated annealing until the r.m.s. error due to the distance restraints was below 0.1 nm. The ten partially refined structures generated with DSPACE were transferred to full potential, restrained dynamics within the program XPLOR (Brunger X-PLOR Manual , Yale University Press, New Haven, Conn., 1988; Brunger et al., *Science* 235:458–460 (1987); Brunger et al., *Protein Eng.* 1:399–406 (1986)). The dielectric constant used within the coulombic potential was set to 80, and the explicit hydrogen bond potential restricted to backbone HN and O atoms only. The distance restraints were in corporated as square well potentials with force constants of 1740 kJ mol$^{-1}$nm$^{-2}$ for long-range and short-range restraints, and 420 kJ mol$^{-1}$nm$^{-2}$ for intraresidue restraints. The structures were first energy minimized for 400 cycles and then subjected to 2 ps of 27° C. restrained dynamics with a time step of 0.0005 ps followed by 20 ps of restrained molecular dynamics at 27° C. with a time step of 0.001 ps. The structures were finally energy minimized.

Figure 18A:
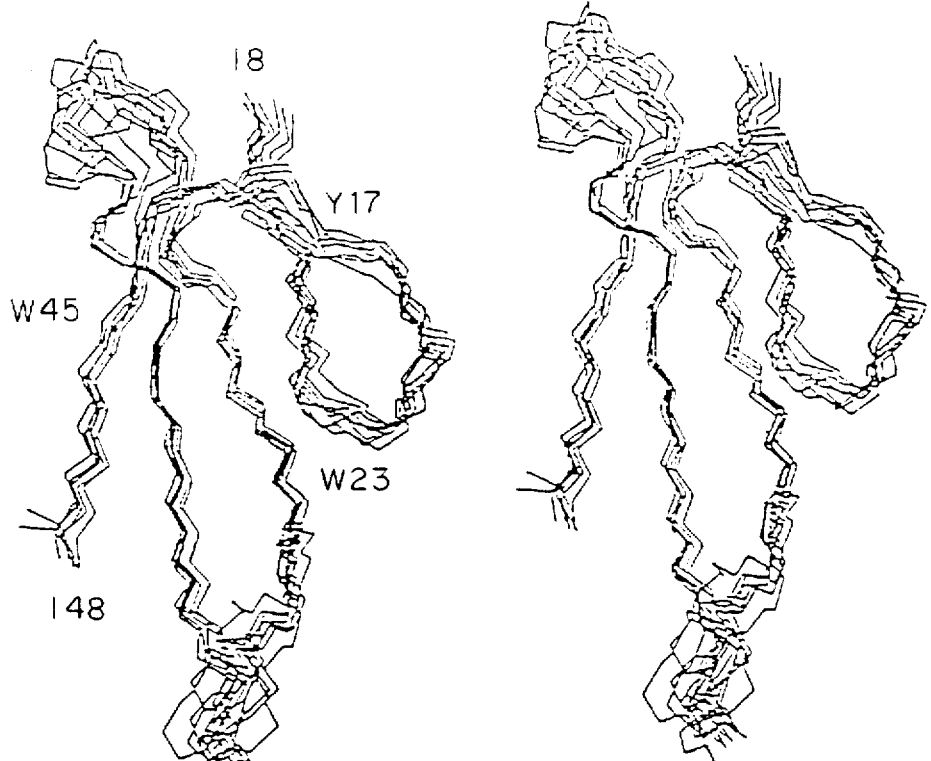
FIG. 18A shows a three-dimensional stereo overlay of the Cα, C, N atom backbone (residues 8–48) of the ten final structures of fibronectin.

Ten separate structures were calculated (FIG. 18A; Table IV); the final backbone structures are shown in FIG. 18A. FIGS. 20–24 are schematic diagrams of the secondary structure in which the type 1 consensus residues (determined by alignment of the human type 1 sequences in FIG. 19) are highlighted.

TABLE V

Structural statistics

|  | Mean | Range |
|---|---|---|
| R.m.s. coordinate deviation from mean coordinate positions (nm)[1] | | |
| Backbone atoms (Cα, C, N, O) | 0.0774 | 0.0762 |
| All atoms (excluding hydrogens) | 0.1318 | 0.0489 |
| R.m.s. deviation from exptl restraints (nm)[2] | | |
| All (381) | 0.0254 | 0.0027 |
| Long range (> i,i + 4) (104) | 0.0053 | 0.0015 |
| Short range (< i,i + 4) (144) | 0.0100 | 0.0018 |
| Intra residue (133) | 0.0416 | 0.0043 |
| R.m.s. deviations from idealized geometry[3] | | |
| Bonds (nm) (724) | 0.0010 | 0.0001 |
| Angles (deg) (1,292) | 0.3060 | 0.0182 |
| Impropers (deg) (241) | 0.0349 | 0.0081 |
| Potential energies (kJ mol$^{-1}$) | | |
| $F_{TOT}$[4] | 611.15 | 130.84 |
| $F_{Bond}$ | 38.69 | 10.81 |
| $F_{Angle}$ | 745.75 | 88.40 |
| $F_{Dihdral}$ | 616.73 | 118.07 |
| $F_{Improper}$ | 18.47 | 8.35 |
| $F_{VDW}$ | -876.62 | 123.71 |
| $F_{Elec}$ | -53.61 | 14.33 |
| $F_{HBOND}$ | -157.88 | 57.87 |
| $F_{NOE}$ | 266.33 | 35.59 |

The dominant structural feature of the module consist of two anti-parallel β-sheets, which is consistent with work on intact fibronectin using infrared spectroscopy (Kotetiansky, et al., *Eur J. Bioch.* 119:619–624 (1981)). Residues Ile 8-Thr 11 form a small double-stranded anti-parallel β-sheet with Val 15-Arg 18. The turn between Thr 11 and Val 15 is relatively poorly defined because the amide protons of Asn 12 and Glu 13 are not observed and so measurement of the dihedral angles was not possible. A loop search of the Brookhaven protein structure data base found that the turn resembled a type 1 conformation.

Following Arg 18, there is a short loop down into the first strand of the triple-stranded anti-parallel β-sheet and, within this loop, there is a conserved glycine residue (at position 20). The triple-stranded β-sheet is composed of strands Asp 21-His 27, His 31-Cys 37 and Trp 45-Ile 48. The close proximity of His 27 and His 31 on the same surface of the β-sheet can explain the dependence of the structure on pH, as the conformational change occurs concomitantly with the titration of these histidines. The turn between His 27 and His 31 is well-defined by NOEs between the side chains (the amide protons of Asp 28 and Met 29 were not observed). The turn was found to be of type 1, with a highly conserved glycine (Gly 30) a in left-handed helical conformation (Sibanda et al., *J. Molec. Biol.* 206:759–777 (1989)).

The definition of the turn with respect to the remainder of the β-sheet is, however, less well-defined. The large turn between the second and third strand of the main β-sheet is not highly restrained by experimentally observed NOE interactions, but seems to be a wide loop that shows considerable flexibility in restrained molecular dynamics simulations.

Figure 18B:
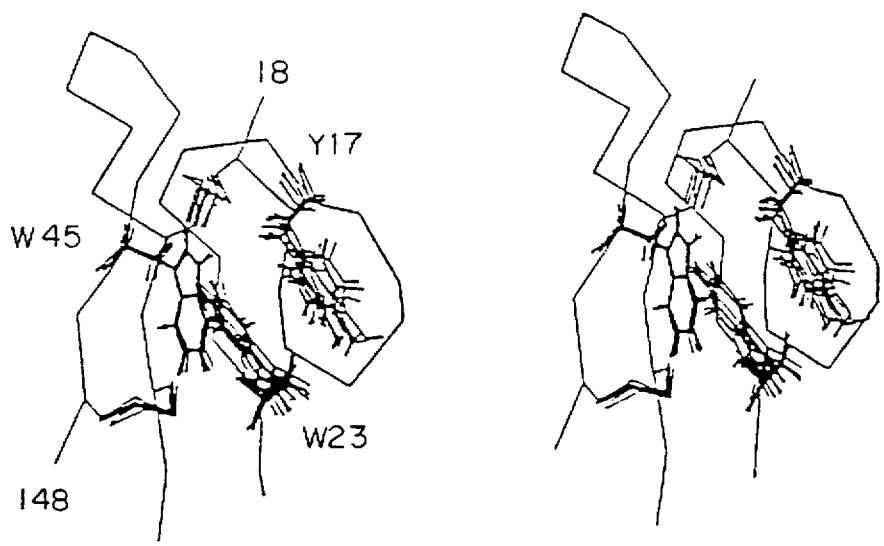
FIG. 18B presents an overlay of the core hydrophobic residues (Y17,W23, and W45) and the consensus disulfide bonds, with part of the average structure C backbone added to aid visualization.

The β-sheets both have a right-handed twist and are stacked on top of one another, enclosing a hydrophobic core consisting of three highly conserved aromatic residues (Tyr 17, Trp 23 and Trp 45) and the two consensus disulfide bonds (FIG. 18B). The disulfide bridge between the first and third cysteines links the two β-sheet subdomains, and the disulfide bridge between the second and fourth cysteines links two adjacent strands of β-sheet.

Knowledge of this structure allows the prediction of those of the other type 1 modules that can have fibrin-binding activity and a more accurate alignment of the type 1 sequences than by sequence comparison alone. There are also implications for the way the modules can link together. The type 1 module occurs 12 times in fibronectin, in three clusters; six occur contiguously at the N-terminus, three more follow two type 2 modules and a further three are found at the C-terminus. The module is rather elongated, with overall dimensions of approximately 1.7 nm×1.6 nm×3.2 nm. Dimensions of approximately 2–2.5 nm×120 nm have been obtained by electron microscopy (Odermat et al., *J. Molec Biol.* 159:109–123 (1989)) for the intact fibronectin dimer. The dimensions of the single module are therefore consistent with an "end-to-end" model for linking the type 1 structures together, although other microscopy studies (Koteliansky et al. *Eur. J. Biochem* 119:619–624 (1981)) have indicated a more globular structure.

All the linker sequences between pairs of type 1 modules are short, apart from that between the fifth and sixth repeat. It is therefore interesting that, as both the N- and C-terminal residues of each repeat lie in a β-sheet, there is the possibility that they could link together through a common β-strand. With five of the type 1 pairs (2–3, 3–4, 4–5, 8–9, and 10–11), if there were a common β-strand, it would pass directly from the C-terminal β-sheet into the N-terminal β-sheet of the following module. In the remaining type 1 pairs, the presence of additional residues in the linking sequences increases the range of conformations that can be modelled.

The type 1 module also occurs in Factor XII and in tPA. In Factor XII it is sandwiched between two epidermal growth factor (EGF)-like modules, and in tPA it occurs at the N-terminus of the molecule adjacent to an EGF-like module. Like the type 1 module, the N- and C-terminal strands of EGF lie in β-sheets such that the type 1 module could also link into the EGF-like modules via a common β-strand.

Comparison of the type 1 sequences shows that those residues buried in the core of the structure are highly conserved, whereas those exposed to the solvent are both variable and predominantly hydrophilic, suggesting that these residues are also exposed to solvent in the intact molecule. One interesting exception is the type 1 module of tPA. In this case, the lower surface of the principal β-sheet (the surface opposite to that which interacts with the minor sheet) has a large hydrophobic area consisting of Leu 22, Pro 24 and Leu 26 on the first strand, Val 31, Tyr 33 and Trp 35 on the second, and Val 46 and Val 48 on the third (numbering with respect to mature tPA). This is in contrast to the opposing surface which has a number of hydrophilic residues (Arg 27, Arg 30, Glu 32, and Ser 45). It is possible, therefore, that the hydrophobic surface is shielded from the solvent in the intact molecule by interacting with one or more of the other modules of tPA.

The dominant feature of the structure consists of two anti-parallel β-sheets which are stacked on top of one another in a sandwich-like arrangement. At the N-terminus there is the minor double stranded sheet whose length extends for about ½ of the module. The chain then loops down in a turn leading into the first strand of the major triple stranded anti-parallel β-sheet. This major sheet extends virtually for the whole length of the module and thus makes the module somewhat elongated with dimensions of approximately 1.7 nm×1.6 nm×3.2 nm. Between the second and third strands of the major β-sheet there is a large, apparently flexible loop which, in the majority of F1 module sequences, contains an unusual Gly×Gly×Gly sequence. Between the stacked β-sheets (i.e. the "sandwich filling"), there is a hydrophobic core (FIG. 18B).

A main question raised by such modelling studies is determining how the modules link together. One way of investigating these linkages is by extension of the methodology described herein to the investigation of pairs of covalently linked modules. This is described in Williams et al, *J. Molec. Biol.*, 235: 1302, 1991. Improved structural models of mosaic proteins are important for the understanding of the structure/function relationships aided by the design and interpretation of module swapping and site-specific mutagenesis experiments.

EXAMPLE VI

Measurement of Fibrin-Binding Activity
a.) Fibrin Affinity Chromatography of 11 kDa FBP.

1. Fibrin affinity chromatography of proteolytic fragments.

The 11 kDa peptide of fibronectin (or 25.9 kDa peptide) and genetically engineered and expressed proteins of fibronectin type I repeat modules are subjected to fibrin-SEPHAROSE™ chromatography as described above. Incubations are performed at 4° C. to promote binding, based on the observation that at 4°, 60% of 11 kDa peptide applied to the column re-bound to fibrin-SEPHAROSE™, whereas, at 37° C., only 49.5% re-bound (using 50% ethylene glycol as the previously improved elution buffer).

The fibrin-binding activity of the proteolytically derived 25.9 kDa fragment of Fn was determined by its ability to bind to a fibrin affinity matrix. The 25.9 kDa proteolytic fragment was solubilized in 1 ml of FBB and combined with 1.5 ml of fibrin-Sepharose. Based on the calculation of the efficiency of coupling of fibrinogen to the Sepharose beads and the loss in molecular weight following conversion of the cross-linked fibrinogen to fibrin (M=340 kDa), 20 nmoles of fibrin were coupled to 1.5 ml of Sepharose beads. Fibrin affinity chromatography was performed as described above for the purification of the 25.9 kDa fragment from Fn digested with subtilisin. FBB was used to equilibrate and wash the column. Following warming of the column to 22° C., the column was washed with FBB until absorbance at 280 nm ($A_{280}$) was less than 0.01, and bound protein eluted with 0.05M Tris-HCl, 0.5M NaCl, 6M urea buffer, pH 7.6.

Figure 25:
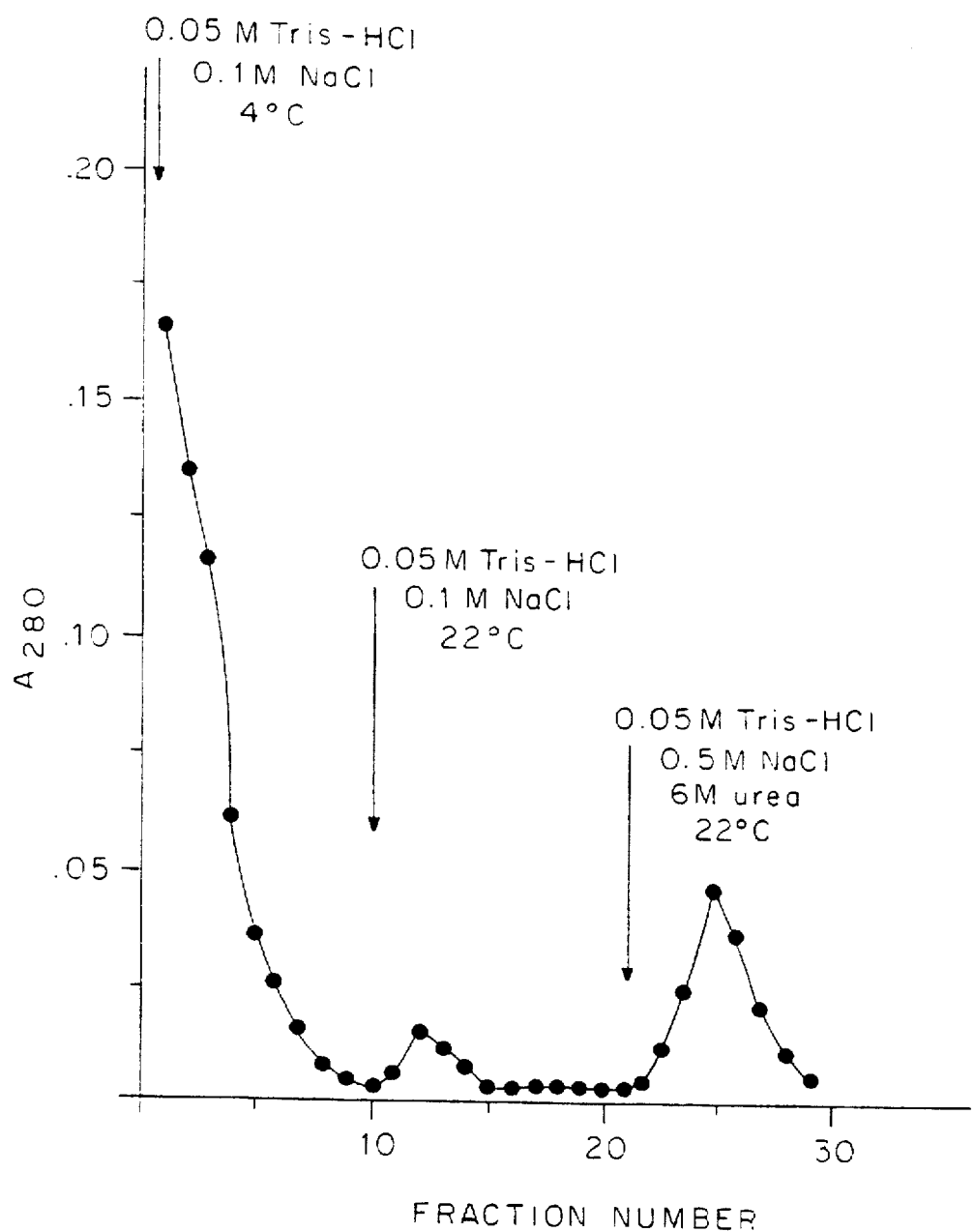
FIG. 25 is a graph showing the binding of the 25.9 kDa proteolytic fragment from the N-terminal domain of fibronectin to fibrin-SEPHAROSE™. This fragment is a single band on the gel. Changes in conditions for elution are indicated by arrows. Fractions were collected and aliquots of pooled fractions were subjected to SDS-PAGE composed of a 5–20% radiant of acrylamide monomer (not shown). The 25.9 kDa fragment was found in the lanes with the 25.9 kDa fragment before application to fibrin-SEPHAROSE™; the unbound fraction; the fraction that eluted after warming the fibrin-SEPHAROAE™ to 22° C.; and the fraction eluted with 0.5M NaCl, 6M urea (the latter two lanes showing significantly less 25.9 kDa fragment than the first two).

The 25.9 kDa fibrin binding fragment demonstrated heterogeneous binding behavior As shown in FIG. 25, although the 25.9 kDa fibrin binding fragment was previously isolated using fibrin-Sepharose affinity chromatography, only a portion of this protein applied to the fibrin-Sepharose was able to bind, using exactly the same conditions that were used for its purification. Based on the protein concentration determined by absorbance at 280 nm, 25% of the proteolytic fragment applied (500 µg) was retained by the affinity matrix. A heterogeneous behavior of fibrin binding of the 25.9 kDa peptide was also found in the bound material, since two fractions were eluted from the matrix under different conditions. A fraction that represented approximately 8% of the protein applied to the fibrin-matrix eluted upon equilibrating the column to room temperature and in an effort to remove all protein remaining bound to the column, the residual 25.9 kDa was recovered following elution with 0.05M tris-CHL, 0.5M NaCl, 6.0M urea, pH 7.6; this represents approximately 17% of the protein that was originally applied to the matrix. Based on Laser desorption mass spectrometry (LDMS), and as shown by the SDS-PAGE, no heterogeneity with respect to molecular mass between the unbound and bound fractions of the 25.9 kDa fragment was observed. If the unbound fraction was reapplied to a separate fibrin-affinity matrix, identical binding characteristics were obtained as described above. The same percent of 25.9 kDa bound to the fibrin-Sepharose and was eluted in each fraction, suggesting that the protein binding is in equilibrium. Moreover, increasing the amounts of the 25.9 kDa applied to a fixed volume of fibrin-Sepharose, continued to show that only 25% of the total protein applied was retained by the fibrin matrix. This indicates that all the sites on the fibrin matrix were not saturated by the protein applied.

2. Fibrin Affinity chromatography of the $^4$F1.$^5$F1 type 1 module. The $^4$F1.$^5$F1 module pair was cloned and expressed as described above (see FIGS. 20 and 21 for secondary structure).

The $^4$F1.$^5$F1 module pair was subjected to fibrin-affinity chromatography to test fibrin-binding function. The module (500 µg/1.0 ml) was incubated for 4 hours (while rotating) at 4° C. in the presence of 1.0 ml fibrin-SEPHAROSE™ (5 mg fibrin/ml SEPHAROSE™ beads) equilibrated in 50 nM Tris-HCl, 0.1M NaCl buffer, pH 7.6. The mixture was poured into a column and after washing unbound protein with 50 nM Tris, 0.1M NaCl, pH 7.6 buffer (FBB), the $^4$F1.$^5$F1, retained by the affinity matrix, was recovered as described in for the 25.9 kDa proteolytic fragment.

The $^4$F1.$^5$F1 also demonstrated heterogeneous fibrin binding properties, with quantities of protein binding to an eluting from the column that were nearly identical to those of the 25.9 kDa fragment. Of the protein (500 µg) applied to the fibrin affinity matrix, 27% bound at 41° C., 9% was released by warming the column to 22° C., and 18% was eluted with the 6.0M urea buffer. The elution profile is shown in FIG. 26B and is reminiscent of FIG. 25. Similarly, as described above for the 25.9 kDa fragment, subjecting the unbound $^4$F1.$^5$F1 to a separate fibrin-affinity matrix showed the identical percent of protein binding and eluting in each fraction and, increasing the amount of $^4$F1.$^5$F1 applied to an unchanged volume of fibrin-Sepharose resulted in the identical 25% of applied protein, binding. An SDS-PAGE demonstrated that all fractions from the column are electrophoretically identical and Electrospray mass spectrometry (ESMS) confirmed the existence of one protein species. In contrast to the elution profile shown in FIG. 26B, FIG. 26C illustrates that nearly 100% of the $^1$F1.$^2$F1 module pair did not bind to fibrin-Sepharose and was recovered only in the unbound fraction following fibrin affinity chromatography; little or no protein was eluted upon warming the column to 22° C. or by the 6.0M urea buffer. Similarly, the $^7$F1 and the $^{10}$F1 recombinant modules did not bind to the Fibrin-Sepharose. These results suggest that the fibrin binding activity found in the 25.9 kDa proteolytic fragment is contained only in the 4th and 5th type 1 modules. Although 6.0M–8.0M urea was the buffer previously described for complete elution of intact Fn and fibrin binding fragments of Fn from fibrin affinity matrices (13, 14, 16–19, 22), to gain further insight into the binding interaction between the $^4$F1.$^5$F1 module pair and fibrin, it was also important to determine whether $^4$F1.$^5$F1 could be eluted with less stringent buffers. In a separate experiment (data not shown), the $^4$F1.$^5$F1 that remained bound to the fibrin-Sepharose following warming of the column to 22° C. (18% of the total protein applied), could not be eluted with 1.0M NaCl. However, 1.0M urea and finally 2.0M urea eluted all the remaining bound $^4$F1.$^5$F1. Thus, the higher molarity urea buffer (6.0M) urea was not necessary to remove all the bound $^4$F1.$^5$F1 from the fibrin matrix. These data may imply that the fibrin-binding interaction of Fn may involve both hydrogen bonding and hydrophobic interactions.

3. Binding of $^{35}$S-methionine labeled recombinant $^4$F1.$^5$F1 and $^{10}$F1-end from Fn to fibrin-SEPHAROSE.

Recombinant proteins from both the N-terminal and C-terminal fibrin binding sites of the Fn molecule were expressed by transfection into $^{35}$S-labeled (methionine) COS cells, as described by Schwarzbauer, *J. Cell Biol.*, 113:1463–1473 and Sottile et al, *J. Biol. Chem.*, 266:12840–12843, (1991) and their fibrin-binding activity determined by affinity chromatography experiment. The $^{35}$S-methionive labeled protein from the N-terminal site was a 10.5 kDa protein that comprised the $^4$F1.$^5$F1 modules ($^4$F1.$^5$F1). The $^{35}$S-methionive labeled 25 kDa recombinant protein from the C-terminal fibrin binding site of Fn expressed by the COS cells commenced in the $^{10}$F1 and extended to the end of the molecule ($^{10}$F1-end). For the affinity chromatography experiments each of the cell culture supernatants that contained the separately expressed proteins (1.5 ml) were combined with 0.4 ml of a fibrin-SEPHAROSE affinity matrix and incubated overnight at 4 C. with end over rotation. Upon removal of the supernatant by centrifugation, the matrices were washed extensively with FBB (10 times with a 0.5 ml wash volume each ); after each wash the matrices were centrifuged and the supernatants removed. Following warming of the affinity matrices to 22° C. the fibrin-SEPHAROSE beads were washed with FBB in the same way as described above, and bound proteins eluted with 0.05M Tris-HCl, 0.5M NaCl, 6M urea buffer, pH 7.6. Aliquots (50 ul) of each fraction was counted in a LS 6000 Scintilation Counter, the corresponding fractions pooled, and analyzed by SDS-PAGE followed by autoradiography. The autoradiograms were exposed for two weeks and scanned with a pdi Desktop Scanner. Image processing and band quantitation of the recombinant proteins that bound to fibrin-Sepharose was assessed by Quantity One, a software for the analysis of 1-D gels. As a control, to indicate the relative level of expression of the recombinant proteins and to confirm their position in the autoradiograms, an aliquot of each COS cell culture supernatant was immunoprecipitated with an anti-fibronectin antibody and compared with the $^{35}$S-labeled proteins retained by the fibrin affinity chromatography matrices by SDS-PAGE and autoradiography. For the immunoprecipitation of $^4$F1.$^5$F1 and $^{10}$F1-end:0.2 ml of the 35-S-methionive laveled culture supernatants derived from the transfected COS cells were combined with 20 ul of a polyclonal anti-Fibronectin antiserum (R39) and 40 ul of Protein A-sepharose (Sigma), and rotated overnight at 4° C. The Protein A-Sepharose beads were separated by centrifugation, washed two times with Tris-buffered saline, resuspended in Laemmli sample buffer and applied to SDS-PAGE.

Figure 30A:
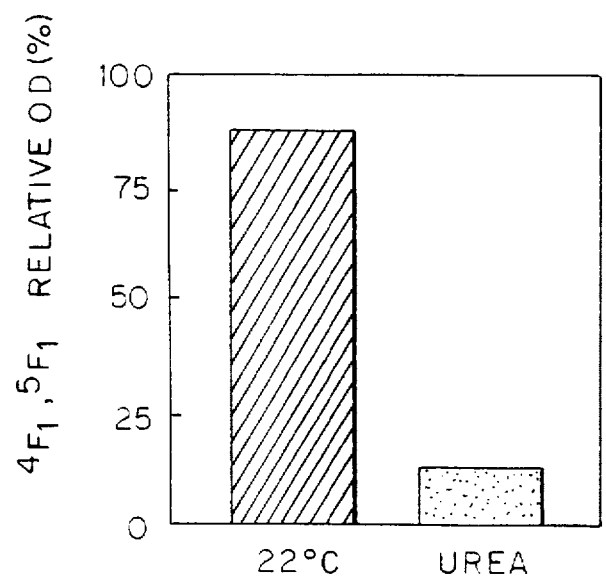
FIGS. 30A and B shows the binding of $^{35}$S-methionine labeled recombinant proteins from both the N- and C-terminal fibrin binding sites of fibronectin to fibrin-SEPHAROSE™ represented by densitometric scanning of the autoradiogram. The DNA fragments encoding the N-terminal fibrin-binding site ($^4$F1.$^5$F1) and a peptide that commences at the beginning of the tenth type 1 module and extends to the end of the fibronectin molecule ($^{10}$F1-end) were transfected and expressed in COS cells. Each of the cell culture supernatants were subjected to fibrin-SEPHAROSE™ chromatography, the affinity matrices warmed to 22° C. and the recombinant proteins that remained bound to the fibrin-matrix eluted with 0.5M NaCl, 6M urea. The pooled fractions were analyzed by SDS-PAGE and autoradiography.
Figure 30B:
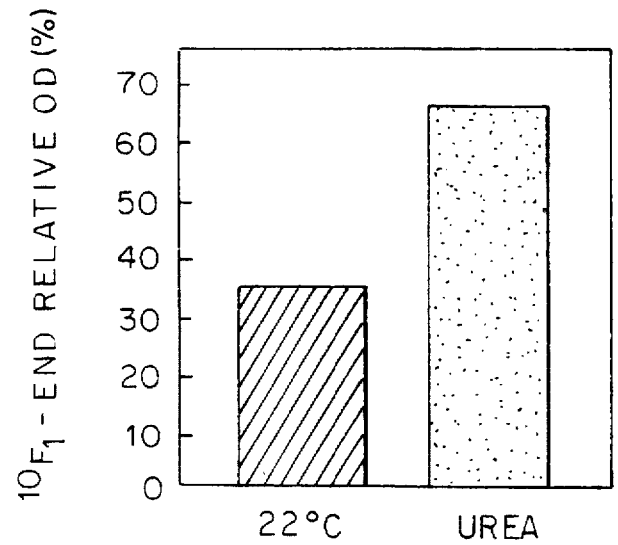

FIG. 30 illustrates the binding of $^{35}$S-methionine labeled recombinant modules from both the N- ($^4$F1.$^5$F1) and C-terminal ($^{10}$F1-end) fibrin binding sites of Fn to fibrin-SEPHAROSE affinity matrices. FIG. 30A shows the bound $^4$F1.$^5$F1 protein and FIG. 30B shows the bound $^{10}$F1-end. The results of the autoradiograms are represented by the graphs which indicate the image analysis of the bound recombinant proteins. The recombinant proteins retained by fibrin-SEPHAROSE that were released from the affinity matrix upon warming to 22° C. were compared to that which eluted from the fibrin-SEPHAROSE with 0.05M Tris-HCl, 0.5M NaCl, 6M urea buffer, pH 7.6.

Image analysis of the recombinant proteins that were retained by the affinity matrices, allowed the quantitation of the optical density of the respective bands (as shown in the right panels of FIGS. 30A, B). Comparison of panel A with panel B indicates that the $^4$F1.$^5$F1 recombinant protein (panel A) from the N-terminus of Fn is released almost entirely by warming the column to 22° C. (88%) while the $^{10}$F1-end showed that only 35% of the protein bound was released by increasing the temperature to 22° C. The remaining 65% required 6M urea in 0.5M NaCl, 0.05M Tris for elution. Therefore, the relative affinity for fibrin of the recombinant proteins tested appears to be different. The $^4$F$_1$.$^5$F$_1$ representing the N-terminal binding site of Fn indicates the lower affinity for fibrin since it was almost. entirely (88%) released from the affinity matrix by a shift of temperature from 4° C. to 22° C. The $^{10}$F1-end, that comprises the C-terminal fibrin binding site of Fn, demonstrated a higher relative affinity for fibrin since 65% of the recombinant protein bound to the fibrin affinity matrix and required denaturing conditions for elution (0.5M NaCl, 6M urea). Thus, the recombinant proteins from both the N- and C-terminal fibrin binding site of Fn indicate a relative affinity for fibrin consistent with that described in this invention for the proteolytic fragments containing the respective binding sites (the 25.9 kDa from the N-terminal and the 11 kDa from the C-terminal).

b.) ELISA

Immunization of rabbits and preparation of antiserum to the 11 kDa fibrin-binding peptide.

Twelve-week old New Zealand white rabbits were immunized with an initial injection of 100 µg of the 11 kDa peptide in 0.37 µl of PBS emulsified with an equal volume of RIBI adjuvant (Immunochemical Research, Inc., Hamilton, Mont.). The rabbits were boosted every two weeks with 0.50 µg/0.185 µl of sterile PBS without adjuvant. After six weeks (3 boosts), a test bleed was obtained and antibody titer assessed by ELISA using 50 ng/100 µl of the 11 kDa peptide to coat the microtiter plates. Preparation of the microtiter plates and ELISA assay are described below. When good titer of the antisera was achieved, about 1.0 Absorbance units at 410 nm ($A_{410}$) with a 1:1,000 dilution, the antiserum was purified by affinity chromatography on a column containing 10.0 ml of GAMMABIND G™ Agarose (Genex Corp.) equilibrated in 0.01M phosphate, 0.15M NaCl, pH 7.0. The IgG fraction was eluted with 0.1M glycine-HCl, pH 2.5. The yield was 12.5 mg/ml of rabbit IgG.

1. Direct Binding of Fibronection and the 11 KDa FBP.

The preparation of fibrin coated microtiter plates was adapted from a method described by Christman et al., *Biochim. Biophys. Acta.* 340:339–347 (1974) and Unkeless et al. *J. Biol. Chem.* 249:4295–4305 (1974). Microtiter (Immulon) plates were coated with fibrinogen at a concentration of 50–1000 ng/well/0.1 ml of Tris buffered saline (TBS). The plates were dried for 24 hours at 37° C. and 0.1 ml of thrombin (20 NIH units/100 ml) containing TRASY-LOL™ (aprotinin) (400 K.I units/100 ml) in TBS was added to each well and the plates incubated for 2 hours at 37° C. Each well is washed one time with PBS and the plates are blocked for 1.5 hours with 1% BSA in TBS to prevent non-specific binding. A constant concentration of fibronectin and the 11 kDa fibrin-binding polypeptide (500 ng/0.1 ml) in 50 mM Tris-HCl, 0.1M NaCl, pH 7.6 (FBB) were incubated separately with fibrin coated microtiter wells (50–1000 ng) for 1 hr at room temperature (23° C.).

The wells were washed three times with FBB containing 0.05% Tween 20 (FBBT) and incubated for 1 hour with 0.05 ml of the a polyclonal anti-fibronectin antiserum (Calbiochem) or the purified IgG fraction of anti-11 kDa rabbit antisera, respectively, at a concentration of 1 µg/ml in FBBT containing 0.1% BSA (FBBT/BSA). Following three washes with FBBT, the wells were incubated with 0.05 ml of alkaline phosphatase labeled goat anti-rabbit IgG (TAGO) at a concentration of 2 µg/ml in FBBT/BSA, for 1 hour. The reaction was developed with 0.05 ml of mg/ml p-nitrophenyl phosphate (Sigma phosphatase substrate tablets) in 10% diethanolamine, pH 9.8 containing 1 mM MgCl$_2$. Binding was assessed spectrophotometrically using a Dynatech ELISA plate reader (MR600) at 410 nm. The results are shown in FIG. 7.

Figure 7:
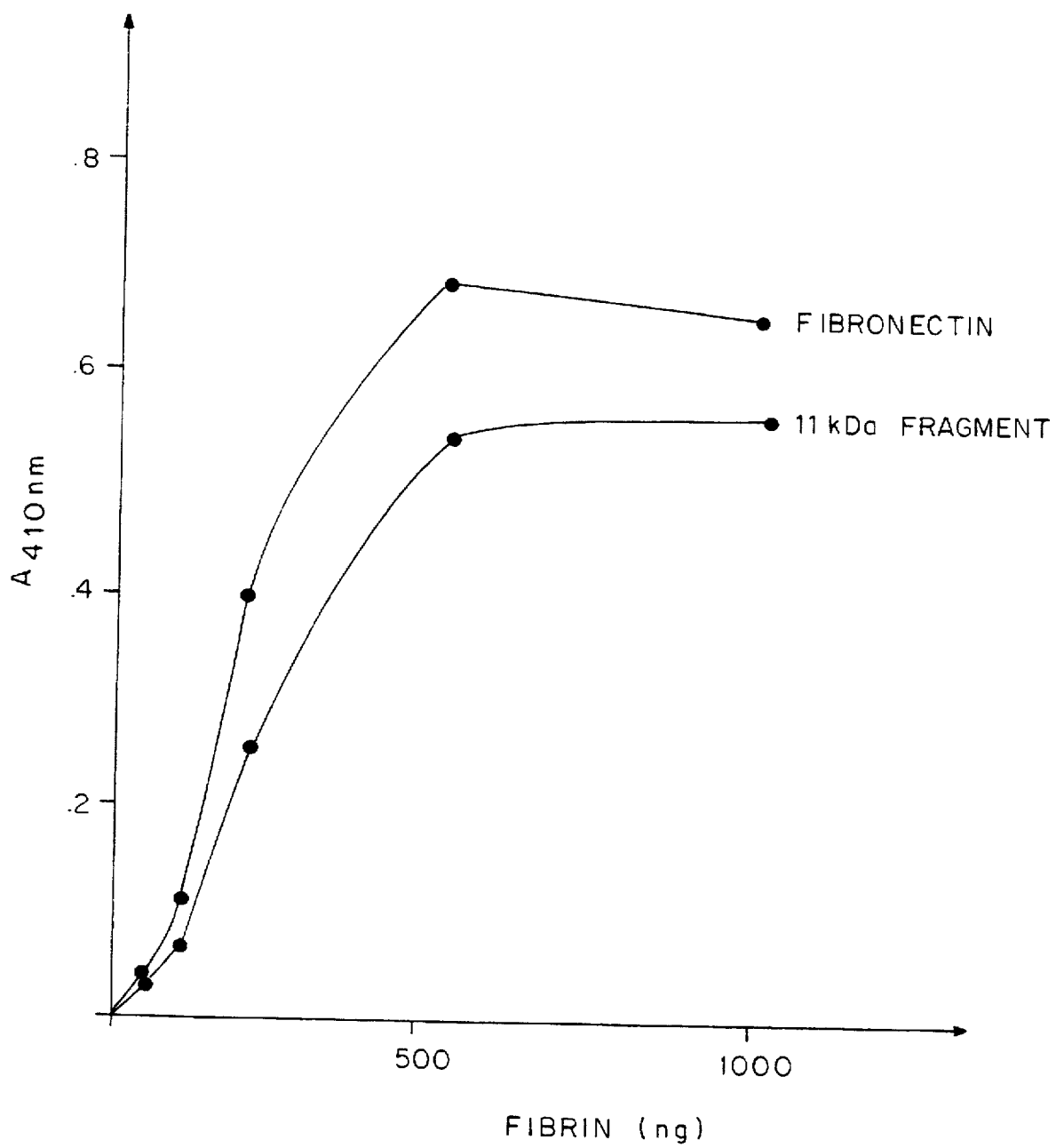
FIG. 7 is a graph showing the binding of fibronectin and the 11 kDa fibrin-binding peptide to fibrin-coated plates in an ELISA. A rabbit polyclonal antiserum made against the 11 kDa peptide was used to detect this fragment, while fibronectin is detected by polyclonal anti-Fn antiserum to intact fibronectin.
Figure 9:
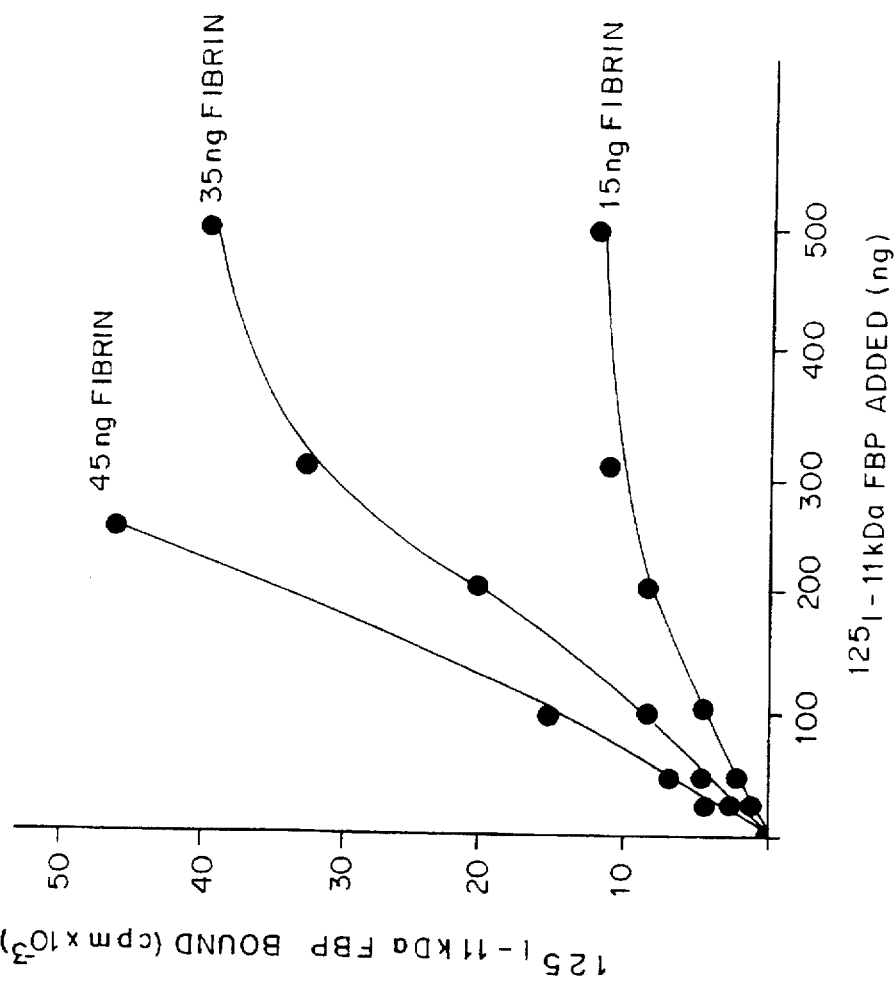
FIG. 9 is a graph showing the binding of $^{125}I$-11 kDa fibrin-binding peptide to fibrin-coated microtiter plates at three different concentrations. Analysis of the binding data by non-linear regression and estimation of the dissociation constant was performed employing GraphPad Prism™.

As observed, both the intact fibronectin and 11 kDa fibrin-binding peptide bound to the fibrin-coated wells in a concentration dependent manner (FIG. 7). The binding varied directly with the concentration of fibrin on the plate. Maximum binding occurred with approximately 500 ng of fibronectin and 500 ng of 11 kDa peptide per 550 ng of fibrin. On a mole-per-mole basis 20 times more of the 11 kDa peptide bound than intact fibronectin.

In general, if there is an antisera available to the polypeptide being tested for fibrin binding, such as the 11 kDa peptide in this case, a direct binding assay can be performed, as was done here.

If there is no antibody available to a fibrin-binding peptide, a competitive inhibition assay must be performed to test binding. In this case, the test polypeptide is incubated with either intact fibronectin or the 11 kDa peptide or a known fibrin-binding peptide (FBP) for which a specific antibody is available, at various concentrations, for an appropriate time period (usually one hour), and inhibition of binding is determined. If intact fibronectin is used, only partial inhibition of binding will be observed due to the presence of two fibrin-binding sites (i.e. fibronectin will bind via the unblocked site). Alternatively, the test peptide can be applied to the fibrin on the plate for a certain time period and inhibition of fibronectin binding assessed by adding the fibronectin, or other known fibrin-binding protein, after the test peptide has been allowed to bind. The test peptide will inhibit binding of the known fibrin-binding protein if it possesses fibrin-binding biological activity.

2. Direct binding of the $^4$F$_1$.$^5$F$_1$ module. Binding of $^4$F1.$^5$F1 to fibrin coated microtiter plates was examined by ELISA as described above. Microtiter wells were coated with fibrin (50–1000 ng) and blocked, as described earlier, and incubated with the module pair $^4$F1.$^5$F1 (500 ng/0.1 ml or 1000 ng/0.1 ml in FBB) for 1 hour, at room temperature. The fibrin-binding activity was quantitated using a mAb N-288 at 1.0 µg/ml for 1 hour followed by alkaline phosphatase labeled goat anti-mouse immunoglobulins (TAGO) for one hour at a concentration of 2.0 µg/ml. The color was developed and fibrin-binding activity demonstrated as described above.

Figure 26A:
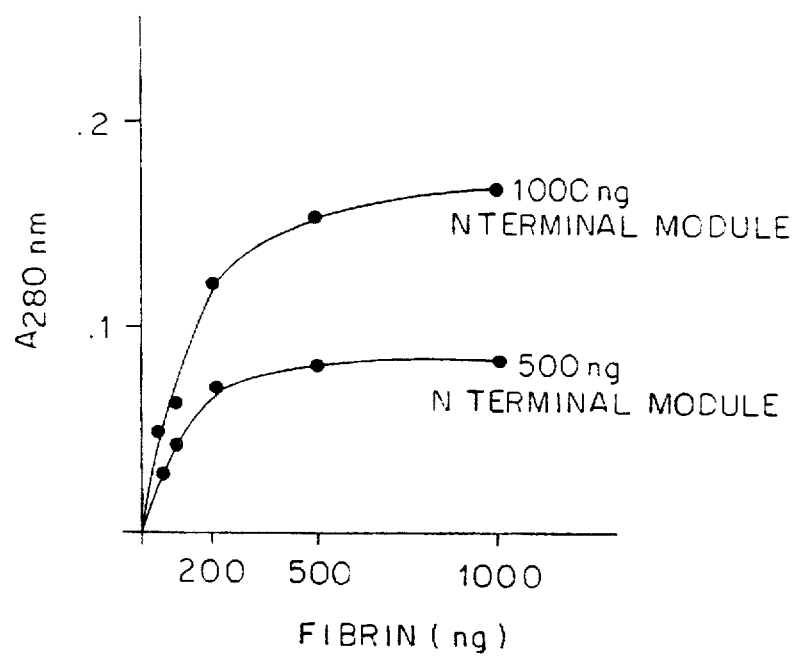
FIGS. 26A–C are graphs representing data for the binding to fibrin of the fibronectin module pair $^4$F1.$^5$F1 from the N-terminal region.
Figure 26B:
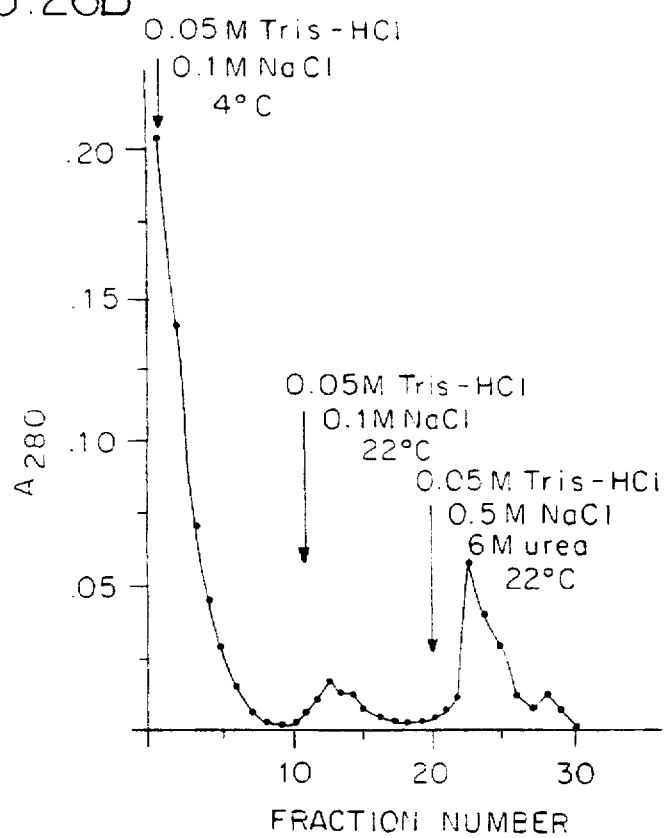
Figure 26C:
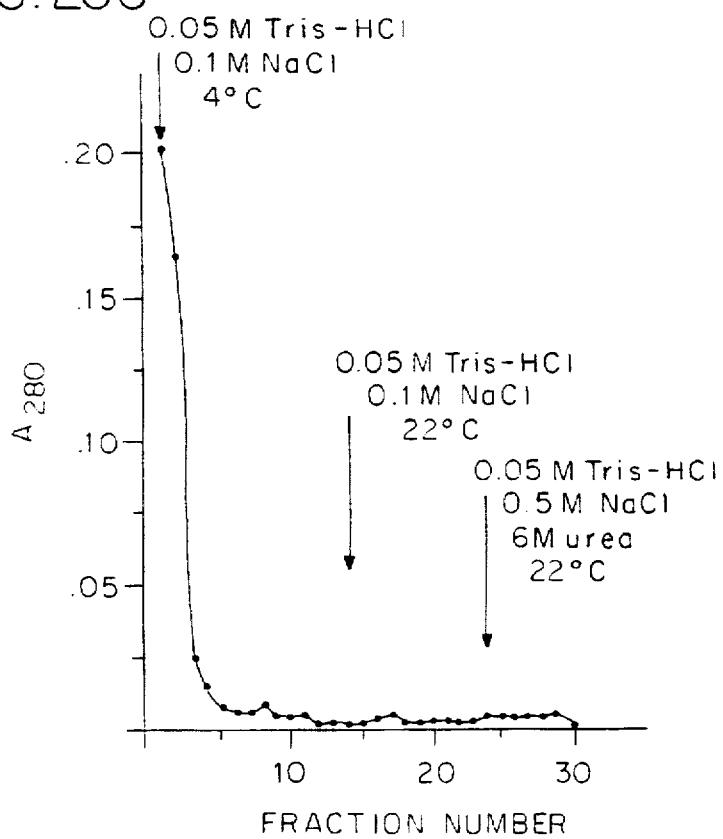

FIG. 26A shows that this N-terminal type I repeat module of fibronectin cloned and expressed in *Saccharomyces cerevisiae* bound to fibrin and that saturating conditions of binding could be obtained with both 500 and 1,000 ng of the N-terminal module. It also appears that a 2:1 ratio of the binding module to fibrin (w:w) was needed to reach saturating conditions at both concentrations.

Figure 8:
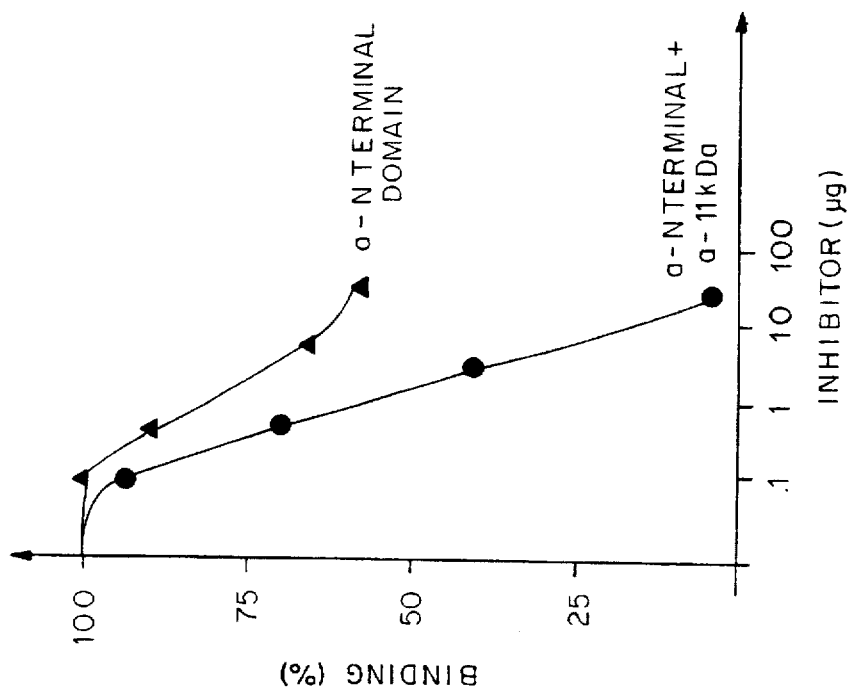
FIG. 8 is a graph showing the inhibition of binding of fibronectin to fibrin by antibodies specific for the N-terminal fibrin-binding domain and for the 11 kDa peptide.

3. Inhibition of fibrin binding by antibodies. FIG. 8 shows the results of an ELISA inhibition assay of fibronectin binding to fibrin, using antisera specific for the N-terminal domain of fibronectin and for the 11 kDa peptide. Fibronectin (150 ng/0.05 ml) was incubated overnight, at 4° C., with various dilutions of: (1) a mouse mAb (0.1–100 µg) to the N-terminus of fibronectin (Mallinckrodt, N-288); and (2) a mixture of the N-288 antibody and a purified IgG fraction of polyclonal antiserum (0.1–100 μg/0.05 ml) against the 11 kDa peptide described above. Fibronectin mixed with antibody was applied to the microtiter plates precoated with fibrin (100 ng/well, prepared as described above) and reacted for 1 hour at room temperature. Bound fibronectin was quantitated as described above. Results are expressed as percentage of fibronectin bound compared with controls incubated with fibronectin that was not preincubated with the antisera.

4. Competitive Inhibition of Fibronectin binding to fibrin by type 1 recombinant modules.

Figure 27A:
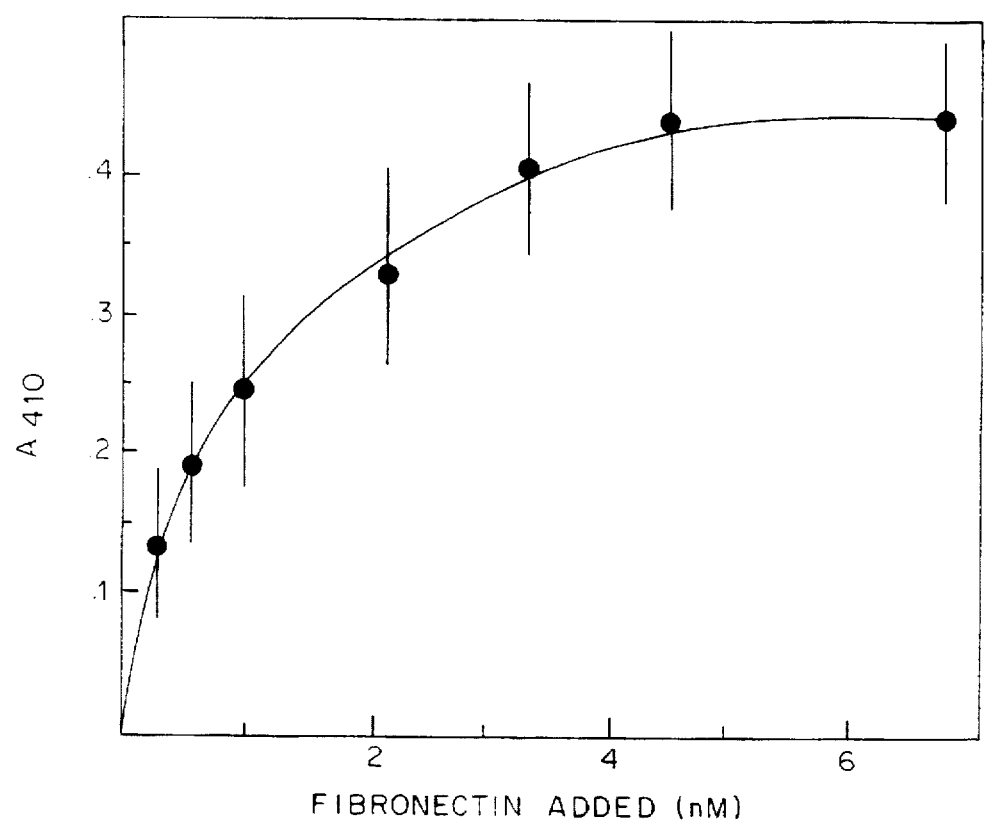
FIGS. 27A–B: ELISA: Competitive inhibition of fibronectin binding to fibrin by type 1 recombinant modules.

Fibrin-binding activity was also assessed by an ELISA. Fn was reacted with fibrin-coated microtiter plates and bound Fn was determined by incubation with a polyclonal rabbit anti-Fn antiserum followed by alkaline phosphatase-labeled anti-rabbit Ig. As indicated by FIG. 27A, the binding of Fn to fibrin was concentration dependent and reached saturation at approximately 200 ng of Fn (4.54 nM) to 200 ng of fibrin (5.88 nM). Thus, on a mole-per-mole basis, assuming complete attachment of all the fibrinogen applied to the polystyrene plate, total proteolytic conversion to fibrin, and accessibility of the binding sites, 0.8 moles of Fn per mole of fibrin were required to achieve maximum binding (assuming a molecular weight of 340 kDa for the fibrin hexamer and 440 kDa for the Fn dimer).

Figure 27B:
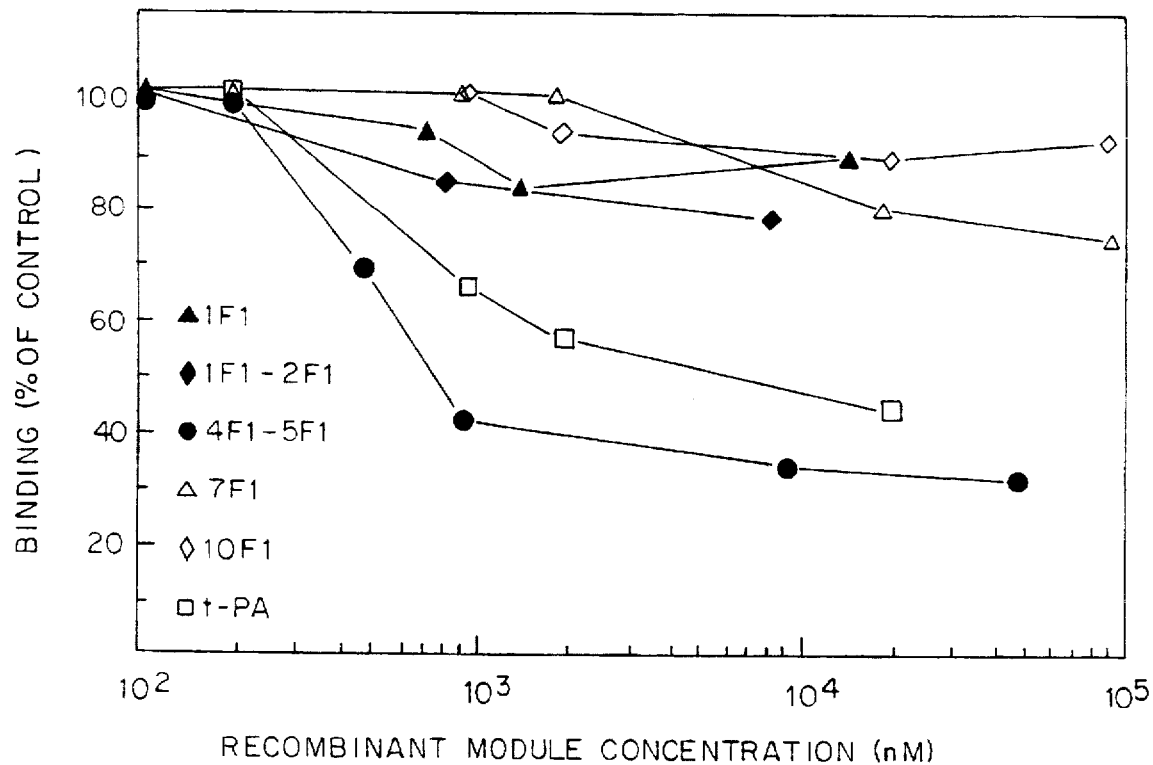

The recombinant Fn modules were used to inhibit the binding of Fn to the fibrin-coated microtiter plates. The inhibition of Fn binding to fibrin by the addition of increasing concentrations of each module was studied at a concentration of Fn (100 ng or 2.3 nM) and fibrin (200 ng) at which 75% of the maximum binding was achieved in a direct assay, as shown in FIG. 27A. As illustrated in FIG. 27B, the $^4$F1.$^5$F1 module competitively inhibited Fn binding to fibrin in a dose dependent manner. Fn binding to fibrin was decreased to 50% by a concentration of 750 nM (325 molar excess) of the $^4$F1.$^5$F1 module. Maximum inhibition was achieved at a concentration of 10 μM (5,000 molar excess) of the $^4$F1.$^5$F1 module. At this saturating concentration, the binding of Fn to fibrin was inhibited by 70%. In contrast, the $^1$F1, $^1$F1.$^2$F1, $^7$F1, and $^1$F1 recombinant Fn modules only slightly inhibited the binding of Fn to fibrin (<20%). This corresponded to a 5,000 and 50,000 molar excess, compared to Fn for the $^1$F1.$^2$F1 and $^7$F1, respectively. Thus, in corroboration with the results obtained by fibrin affinity chromatography, of the fibronectin type 1 modules tested, only the $^4$F1.$^5$F1 recombinant protein demonstrated specific fibrin-binding activity. Furthermore, the $^4$F$_1$.$^5$F$_1$ showed greater inhibition of fibronectin binding than the t-PA type 1 module (70% compound to 55%).

In summary of these results, the type 1 repeat modules that do not contain the fibrin-binding sequence do not demonstrate fibrin-binding activity. The $^4$F1.$^5$F1 module pair blocked the binding of fibronectin to fibrin (36%) to approximately the same degree as the an antibody specific for the N-terminal fibronectin domain (40%) (FIG. 29). These results can imply that the $^4$F1.$^5$F1 module pair can possess full fibrin-binding activity because, this module pair completely inhibited the N-terminal fibrin-binding site in fibronectin (represented by the 25.9 kDa fragment) from binding to fibrin.

Certain Fn type 1 repeat modules of the present invention possess fibrin-binding activity, and the three dimensional structures of all twelve are discovered to be substantially similar. However, modules without fibrin-binding activity are discovered not to be biologically active in fibrin binding. Competitive ELISA established that the first, second, fifth, seventh, and tenth genetically cloned type 1 repeat modules possess little or no fibrin-binding activity (between 0 and 20% at higher molar concentrations) (FIGS. 27B and 28B; each module was caused to compete separately with intact Fn for binding to fibrin). The $^4$F1.$^5$F1 module pair showed better competitive binding activity than the t-PA module (30% inhibition compared to 45%).

5. Direct binding of biotinylated Fn to fibrin.

Figure 28A:
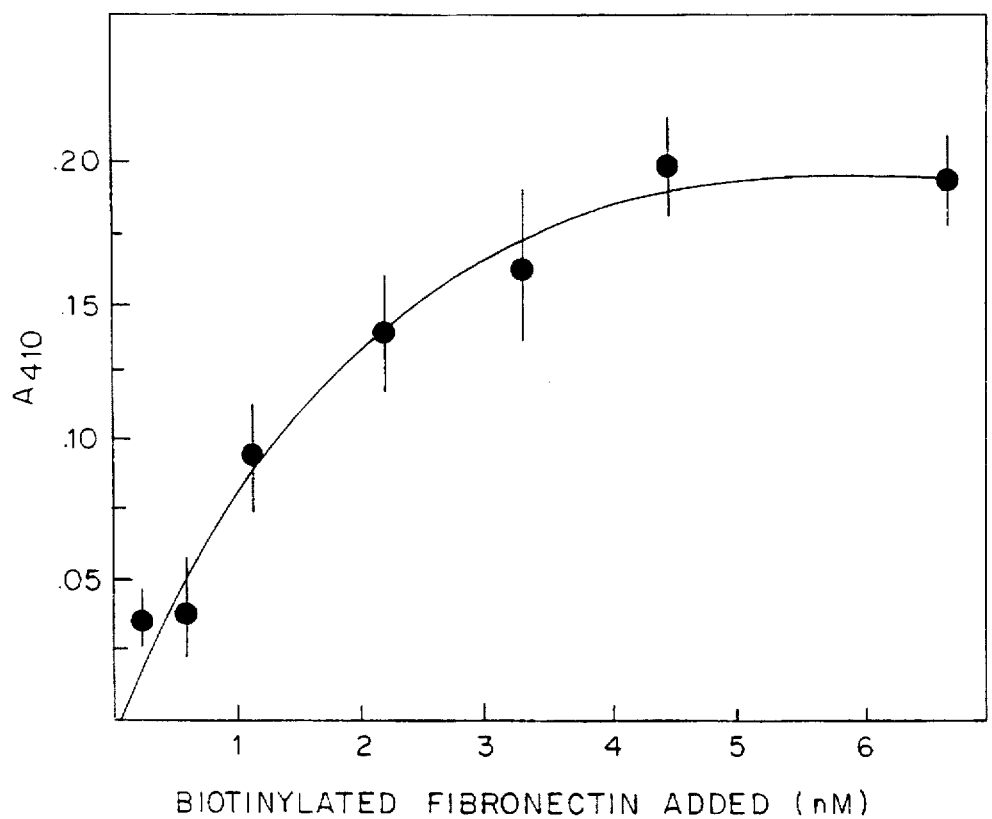
FIGS. 28A–B represent the competitive inhibition of biotinylated fibronectin binding to fibrin.

Since the anti-Fn detection system described for the ELISA above could not be used in Fn competition assays employing the intact Fn molecule or the 25.8 kDa proteolytic fragment, purified Fn was biotinylated using water soluble NHS-LC-Biotin (Pierce Chemm. Co.; according to the manufacturer's instructions) and binding to fibrin detected by alkaline phosphatase conjugated streptavidin (diluted 1/500 in FBBT/BSA) for 1 hour at 22° C., followed by the addition of p-nitrophenyl phosphate, as described above. To ensure that the biotinylation of the Fn had not affected its ability to bind to fibrin, fibrin-binding activity was tested by incubating increasing concentrations of biotinylated Fn (10–300 ng/0.1 ml FBB) with the fibrin-coated wells (200 ng) and detected (see FIG. 28A) using alkaline phosphatase-conjugated streptavidin and the reaction developed as described for Direct Elisa. As depicted in FIG. 28A, the biotinylated protein exhibited identical fibrin-binding characteristics as the non-labeled Fn molecule, detected with anti-Fn antibody as shown in FIG. 27A. In both experiments saturation of binding was achieved with 4.5 nM (200 ng) of Fn reacted with 5.88 nM of Fn (200 ng) on the plate.

6. Competitive inhibition of biotinylated fibronectin to fibrin by unlabeled intact Fn, the 25.9 kDa $NH_2$-terminal proteolytic fragment, and recombination type I modules.

Figure 28B:
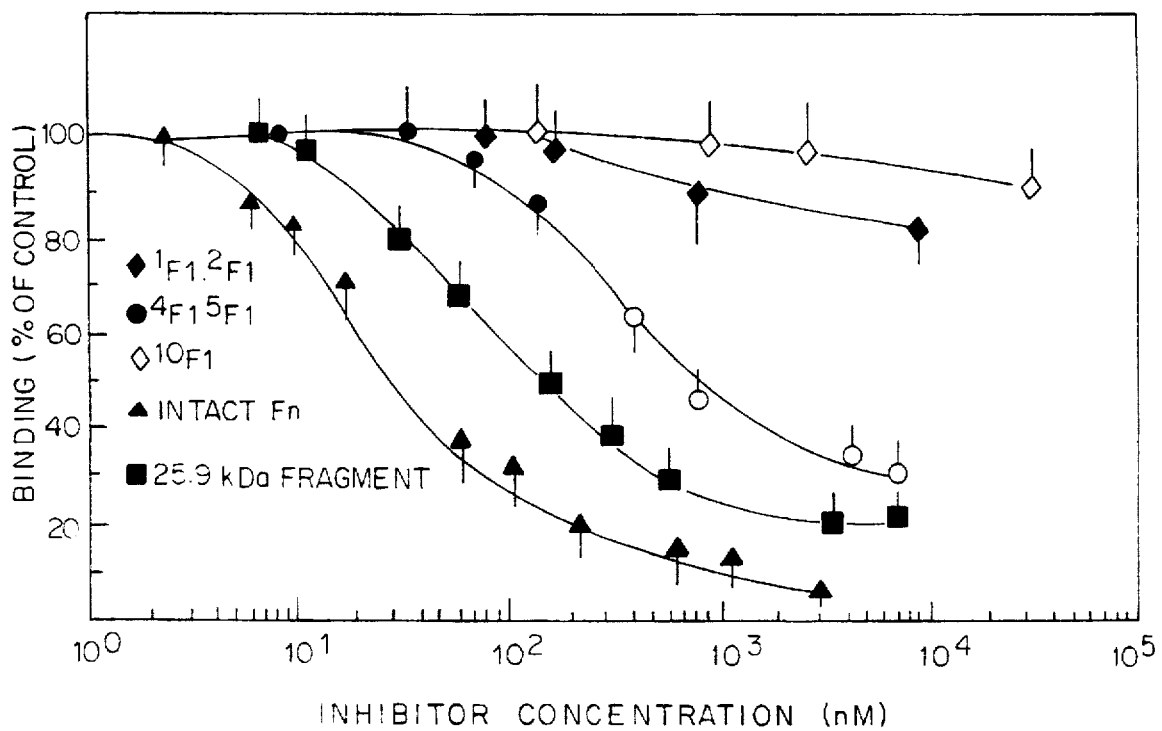

To compare the relative fibrin-binding affinities of the $^4$F1.$^5$F1 recombinant module pair and the 25.9 kDa proteolytic fragment ($^1$F1–$^5$F1) with that of the native Fn molecule, these purified proteins were competed with biotinylated plasma Fn for binding to fibrin coated wells and the extent of inhibition of binding assessed by incubation with alkaline phosphatase-conjugated streptavidin. Competitive inhibition of biotinylated Fn binding to fibrin coated microtiter wells was performed at a concentration of biotinylated Fn that achieved 75% saturation (100 ng biotinylated Fn/200 ng fibrin-coated wells, as derived from the saturation curve obtained above, FIG. 28A). Biotinylated Fn (100 ng/0.1 ml FBB: 2.3 nM) was combined with increasing concentrations (0–10 μM) of either unlabeled Fn, the 25.9 kDa proteolytic fragment, or the separate $^4$F1.$^5$F1, and $^{10}$F1 recombinant modules and incubated with the fibrin-coated microtiter wells for 1 hour at 22° C. Protein concentrations for the 25.9 kDa fragment and the recombinant type 1 modules were determined using molar extinction coefficients at 280 nm ($M^{-1}$ $cm^{-1}$, 280 nm) that were calculated by the software GPMAW. The values are: $6.3 \times 10^4$ for the 25.9 kDa fragment, $2.7 \times 10^4$ for the $^4$F1.$^5$F1, $2.1 \times 10^4$ for the $^1$F1.$^2$ $^F$1, and $8.7 \times 10^4$ for the $^{10}$F1. Bound biotinylated Fn was quantitated as described above. The results are presented as the percentage of control of biotinylated Fn binding in the absence of the competitive inhibitor. As illustrated in FIG. 28B, each of these fibrin-binding proteins demonstrated a dose dependent inhibition of biotinylated Fn binding to fibrin. In contrast, the non-fibrin-binding recombinant modules, $^{10}$F1 and $^1$F1.$^2$F2 module pair, inhibited biotinylated Fn by 10 and 15%, respectively, corroborating the results indicated in FIG. 27B. Complete inhibition of binding of biotinylated Fn (2.3 nM) required a 1000 molar excess of unlabeled Fn (2.2 μM); the $IC_{50}$ was 20 nM (8.7 molar excess). Due to the fibrin-binding activity in the COOH-terminus of Fn, the 25.9 kDa proteolytic fragment and the $^4$F1.$^5$F1 would not be expected to achieve 100% inhibition of binding. As shown in FIG. 28B, the 25.9 kDa fragment and the $^4$F1.$^5$F1 demonstrated maximal inhibition of biotinylated Fn binding to fibrin by 75% and 67%, respectively, with 10 μM of each protein (5,000 molar excess). Fifty per cent inhibition of binding of biotinylated Fn to fibrin was obtained with a concentration of 150 nM of the 25.9 kDa proteolytic fragment (65 molar excess) and 700 nM of the $^4$F1.$^5$F1 than the 25.9 kDa proteolytic fragment was required to inhibit biotinylated Fn binding to fibrin (IC$_{50}$), it can be ascertained the proteolytic fragment containing the $^1$F1–$^5$F1 type 1 modules interacts with fibrin with higher affinity than the $^4$F1.$^5$F1. Based on the IC$_{50}$ valves and employing the equation of Cheng and Prussoff (*Biochemical Pharmacology* 22, 3099–3108, 1973) the KI values were estimated as 145 nM for the N-terminal proteolytic fragment and 695 nm for the $^4$F1.$^5$F1 module pair. A 7.5 fold higher concentration of the 25.9 kDa fragment over intact Fn was needed for 50% inhibition of binding of biotinylated Fn, presumably, as described above, due to the greater binding capacity of the intact Fn molecule provided by both fibrin-binding sites. It is noteworthy, that the maximum degree of inhibition achieved, as well as the concentration of the $^4$F1.$^5$F1 required to produce 50% inhibition of Fn binding to fibrin, are equivalent to the results shown in FIG. 27B. Since the $^{10}$F$_1$ module is one of the three type 1 repeats in the COOH-terminus of Fn that could have potential for fibrin binding, it did not, as a single module, exhibit fibrin-binding.

7. The $^4$F1.$^5$F1 and a MoAb to the NH$_2$-terminus of Fn inhibit Fn binding to the same extent. Since both the fibrin affinity chromatography and competitive ELISA indicated that the fibrin binding activity in the NH$_2$-terminus of the Fn molecule was attributed to the $^4$F1.$^5$F1 module pair, it was germane to determine whether the degree of inhibition of Fn binding to fibrin caused by $^4$F1.$^5$F1, was comparable to the inhibition caused by blocking this module pair in the intact Fn molecule with a MoAb that specifically recognized this site. The epitope recognized by this anti-Fn MoAb (N288) was mapped to the $^4$F1.$^5$F1 through a direct binding ELISA in which recombinant Fn modules $^1$F1, $^1$F1.$^2$F1, and $^4$F1.$^5$F1 were coated on microtiter plates and directly reacted with MoAb N-288 and detected by alkaline phosphatase labeled Ig (unpublished observations). The MoAb N-288 also reacted with the 25.9 kDa fragment (data not shown), by Western blot analysis, but not with other fragments of subtilisin-digested Fn (except some minor cleavage fragments of the NH$_2$-terminal region, as determined by amino acid sequencing). For these experiments shown, in FIG. 29, biotinylated Fn was used to avoid cross-reactivity of the secondary anti-Ig antiserum with MoAb N-288 used to inhibit Fn binding to fibrin in these experiments.

The binding of biotinylated Fn to fibrin-coated microtiter wells was competitively inhibited in the following experiments: 1) an affinity purified MoAb to the N-terminal domain of Fn (N-288, Mallinkrodt) and 2) the $^4$F1.$^5$F1 recombinant module, for comparison. In the former, each well of the microtiter plates was coated with 200 ng of fibrin, as described above, and reacted with biotinylated Fn (100 ng/0.1 ml TBS) that had been preincubated for 1 hour with the MoAb N-288 (0.1–25 μg). Pre-incubation of biotinylated Fn with identical concentrations of a MoAb to the cell binding domain of Fn (N-295, Mallinkrodt) was used as negative control. In the latter, biotinylated Fn (100 ng/0.1 ml TBS) was combined with increasing concentrations (0.1–25 μg) of the $^4$F1.$^5$F1 and incubated with the fibrin coated wells (200 ng) for one hour at 22° C. Bound biotinylated Fn was quantitated and presented as described above.

FIG. 29 demonstrates that a does dependent inhibition of Fn binding to fibrin was obtained by both the $^4$F1.$^5$F1 and the MoAb N-288 supporting the specificity of the interaction of Fn with fibrin. Conversely, MoAb N-295, to the cell-binding domain of Fn showed no inhibitory activity. A maximum of 67% inhibition of Fn binding was observed with both the $^4$F1.$^5$F1 and the MoAb, as inhibitors of Fn binding to fibrin. This is the identical level of inhibition obtained with this module shown by the ELISA in FIGS. 27B and 28B, using the same concentration of the $^4$F1.$^5$F1. Although 16 times more $^4$F1.$^5$F1 than antibody (w/w) was used to obtain maximal inhibition of Fn binding to fibrin, these results demonstrated that a similar degree of inhibition could be achieved by either competing Fn fibrin binding activity with the $^4$F1.$^5$F1 or by specifically blocking these repeats in the intact Fn molecule. This provides further evidence that the $^4$F1.$^5$F1 type 1 module pair represents the only site involved in the fibrin-binding activity of the NH$_2$-terminal domain of Fn. We did not directly test the $^3$F1 in our assays. However, since the Fn fibrin-binding activity could be inhibited to the same extent by the recombinant protein and the fibrin site specific antibody, the possibility that the $^3$F1 contributes to the fibrin binding of the intact Fn molecule is obviated. Whereas, at least two fibrin binding sites have been described for Fn, we now provide evidence by blocking the active NH$_2$-terminal fibrin binding site, that this site is functionally contributing to fibrin binding of the intact molecule under physiological conditions and therefore, this activity is not an artifact of the excision of this protein structure from the parent molecule.

c.) Fibrin Clot Assays

1. Histological examination of FBP's binding to fibrin clots.

A more physiological method of detecting fibrin binding is to test the binding to prepared fibrin clots and subsequently examine the clot, histologically. The fibrin-binding peptide (FBP) is labeled with either fluorescein by the method of Dickler, *J. Exp. Med.*, 140, 508 (1974) or by radiolabeling with iodine $^{125}$Iodine. The method for fibrin clot formation is described by Thorsen et al., supra). Briefly, a mixture of 0.2% bovine plasminogen-free fibrinogen is incubated with thrombin in saline barbital buffer (SBB) and the fibrin is separated from the solution by winding on a glass rod at room temperature. All fluid is released from the clot by pressure and the clot incubated with the labeled fibrin-binding peptide for various periods of time. Following gentle washing of the clot in SBB to remove unbound labeled protein, the clot is quickly frozen at −20° C., cut to 6–8 microns thick in a cryostat (Ames), and collected on an acid washed and 3-aminopropyltriethoxysilane treated microscope slide. The slides are fixed in 10% formalin solution for 60 minutes, rinsed with water, stained (Hematoxylin or toluidine blue or another appropriate stain), and either mounted with a water or solvent insoluble slide mounting solution (depending on the chosen stain, e.g., AQUAMOUNT or PERMOUNT). The slides are examined for fluorescence using a Zeiss photomicroscope equipped with an epifluorescent attachment and excitation filters. If radiolabeled fibrin-binding polypeptides are used, the slides are subjected to autoradiography to detect binding. It is expected that attachment is only observed around the periphery of the clot with this procedure. Controls are at least one of predetermined labeled non-fibrin-binding proteins and known fibrin-binding protein (FBP) of similar molecular mass.

An alternative method to detect binding to the fibrin clot, is to form the clot, immediately freeze the tissue, and cut the tissue for the microscope slide. Following drying, the cut clot section is incubated in humido, with the fluorescein or radioiodinated fibrin-binding peptide. If the peptide is immunoreactive with any of the antisera, the peptide need not to be labeled and the procedure will follow with fluorescein labeled goat anti-rabbit IgG. $^{125}$I labeled protein A can also be used as a detection system followed by autoradiography. The slide is treated and analyzed as described herein.

2. Testing of fibrin-binding of FBPs in an in vitro clot binding assay.

Radiolabeled FBPs are stored for no longer than two weeks at −20° C. in 0.1% BSA-PBS. Fibrin binding of $^{125}$Iodine-FBPs is performed in at least one of two ways: 1) during clot formation and 2) at various time periods after clot formation. This determines the efficacy of FBPs in binding to both newly forming clots (thrombi) and old clots in vivo. If FBPs continue to be incorporated into forming thrombi with time and remain relatively unchanged in their binding to preformed (old) thrombi over time, then radiolabeled FBPs can be used in vivo to distinguish old thrombi from actively forming thrombi.

Assays: 1) 20–200 μl fresh whole human blood, non-citrated, is mixed with various concentrations of $^{125}$I-FBP, in the presence of 0.1% BSA, 5 mM $CaCl_2$, and 1.0 U/ml of thrombin (total volume=250 μl). $CaCl_2$ and thrombin are not used if non-citrated blood is used. The reaction is incubated for 30 minutes (or various time periods) at 37° C. and terminated by the addition of 25 mM EDTA. The mixture is centrifuged, the supernatant discarded, the pellet washed twice, in 1.0 ml PBS, 0.1% BSA, 5 mM EDTA, and 1.0 mM PMSF, and bound FBP determined by counting the pellet in a gamma counter. The specificity of FBTs binding to clots is determined by competing radiolabeled FBPs with unlabeled intact Fn, the 11 kDa and 25.9 kDa FBPs, and recombinant FBPs. All fibrin-binding sites are preferably saturated in order to observe competition. Thus, clot size is varied until saturation is obtained (binding of radiolabeled FBPs has reached a plateau). For these experiments, various concentrations of cold FBPs are added together with the radiolabeled FBPs to the clot, and inhibition of binding determined. This demonstrates the relative affinities of FBPs (by displacement) and specificity of the interaction. 2). Binding of $^{125}$I-FBPs to preformed fibrin clots is performed as above, except the $^{125}$I-FBP is not added until after the clot has been formed and terminated at 30 minutes. The $^{125}$I-FBP is added for various time periods, after clot formation, and fibrin binding quantitated as described above.

3. Assessing radiolabeled FBP binding to developing and preformed clots in the presence of effectors of clot formation.

Fibrin binding experiments are performed in the presence of thrombin, hirudin (inhibitor of thrombin), Calcium (clot formation is calcium dependent), and heparin (inhibitor of clot formation) to determine their effects on $^{125}$I-FBP binding to both forming and preformed clots. Many patients that would receive FBP for imaging etc., are heparinized and thus it is important to determine the extent heparin inhibits FBPs from binding to thrombi. The effect of plasma trans-glutaminase (Factor XIII) cross-linking on FBPs binding to fibrin clots is also determined. The addition of the primary amines, spermidine, putrescine and/or inhibitors of Factor XIII, indicates the contribution of Factor XIII, in blood, to FBPs binding to fibrin clots.

EXAMPLE VII

Iodination of Proteins and Estimation of Binding Affinity Constants

Fibrin-binding peptides can be labeled with $^{125}$I for use in the fibrin clot assay and for estimation of binding affinity constants. Labeling with $^{123}$I or $^{131}$I is preferable for gamma scintigraphy.

Fibrin-binding activity of the 11 KDa following radioiodination.

1. Fibrin affinity chromatography.

Figure 12:
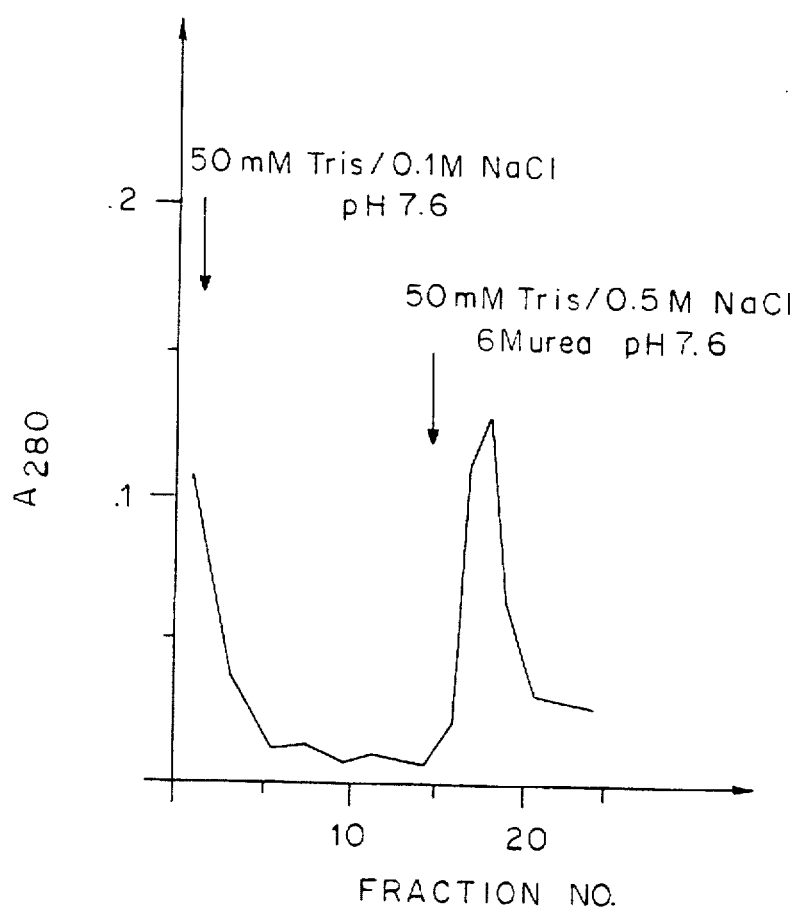
FIG. 12 is a graph showing the binding of the 11 kDa fibrin-binding peptide to fibrin-SEPHAROSE™ following labeling with $^{125}I$. Bound $^{125}I$-11 kDa fragment was eluted from the affinity matrix with 0.5M NaCl, 6M urea as indicated in the graph.

The 11 KDa peptide (50 μg/0.206 ml) was radiolabeled using the IODO-BEAD method (Pierce Chemical). The peptide was added to one IODO-BEAD in the presence of 100 μCi $^{125}$I (17.4 Ci/mg, New England Nuclear) and incubated on ice for 10 minutes. The bead was removed and the free $^{125}$I removed by chromatography through a PD10 column containing SEPHADEX™ G-25 (Pharmacia). Following precipitation of the peptide with trichloracetic acid the specific activity was determined to be between 0.5–1.0 μCi/μg (LKB Automatic Gamma counter). The radioiodinated 11 kDa fibrin-binding peptide (500 μg/1.5 ml) was combined with 1 ml of fibrin-SEPHAROSE™ (5 mg fibrin/ml beads) equilibrated with 50 mM Tris-HCl, 0.1M NaCl buffer, pH 7.6, and rotated for 4 hours, at 4° C. The mixture was poured onto a disposable column (0.6 cm×8.0) and the unbound protein washed through. The column was equilibrated to room temperature and washed with the equilibration buffer. The $^{125}$I-peptide that had been retained by the fibrin affinity matrix, was eluted with 50 mM Tris-HCl, 0.5M NaCl, 6M urea, pH 7.6 (the volume of each fraction was 0.7 ml). The amount of protein that bound to fibrin-SEPHAROSE™ represented 60% of the radiolabeled 11 kDa polypeptide applied (measured as total protein bound/total protein applied), measured by absorbance at 280 nm ($A_{280}$) (FIG. 12).

In alternate approaches the peptide is labeled using Iodogen (Pierce Chemical) exactly as described by the manufacturer. Chloramine T is used if the specific activity obtained is not sufficient for a particular study. If tyrosine residues are not available for iodination, Bolton-Hunter reagent can be used to label available lysines.

2. ELISA a.) Direct binding assay.

To be used for imaging, the biological activity of FBPs must be retained following derivatization with radiolabeled iodine. The 11 kDa FBP (containing three tyrosines of which two are exposed by hydropathy analysis) was radiolabeled with 1.0 mCi $^{125}$Iodine in the presence of Iodobeads™, as described herein. The specific activity obtained was 4.0 uCi/ug (TCA precipitable counts). The fibrin-binding activity of iodinated 11 kDa was assessed by ELISA employing a direct binding assay. Increasing concentrations of the 11 kDa FBP (25–500 ng/0.1 ml in 50 mM tris, 0.1M Na Cl, pH 7.6 buffer (FBB) were added to microtiter detachable microtiter wells (Immulon 2 Removawells) coated with three fibrin concentrations (15, 35 and 45 ng) and incubated for 1 hour at room temperature. After removal of the unbound material, and extensive washing with FBB containing 0.1% Tween 20, bound $^{125}$Iodine-11 kDa FBP was determined by assessing the radioactivity attached to the individual detachable wells using a LKB-Wallac 1272 CliniGamma counter (Wallac, Finland). Non-specific binding was calculated, by determining the radioactivity attached to wells coated with BSA. The concentration of fibrin attached to the microtiter wells was quantitated employing the Quanitgold (Diversified Biotech.) protein assay kit, adapted for ELISA plates.

Computer analysis of the binding data, by non-linear regression and curve fitting to the mathematical equation corresponding to the one binding site model was performed employing GraphPad Prism™. Analysis of the binding curve yielded an estimated dissociation constant of 154 nM for the radiolabeled 11 KDa FBP.

b.) Competitive inhibition of the binding of $^{125}$I-11 kDa to fibrin.

Competitive inhibition of $^{125}$I-11 kDa binding to fibrin coated microtiter wells was performed at a concentration of 11 kDa that achieved 50% saturation (100 ng $^{125}$I-11 kDa/15 ng fibrin-coated wells). This was derived from the saturation curved obtained above $^{125}$I-11 kDa (100 ng/0.1 ml FBB: 90 nM) was combined with increasing concentrations (1–5,000 nM) of unlabeled 11 kDa FBP and immediately incubated with fibrin coated wells for 1 hour at 22° C. Bound $^{125}$I-11 kDa was determined as described above. The results are presented as the percentage of control of $^{125}$I-11 kDa binding in the absence of the competitive inhibitor. An unrelated protein, egg lysozyme, was employed as negative control. Analysis of the binding data was performed by non linear regression and curve fitting to the one-site competitive binding curves (GraphPad Prism).

Figure 10:
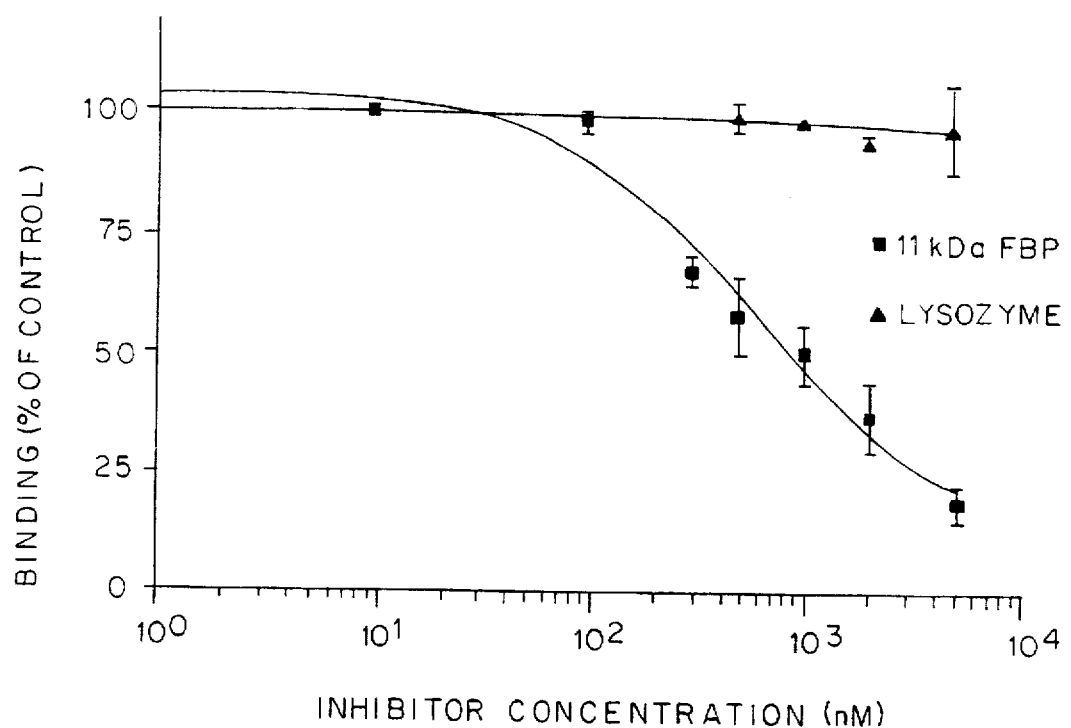
FIG. 10 is a graph indicating the competitive inhibition of $^{125}I$-11 kDa binding to fibrin-coated microtiter wells by unlabeled 11 kDa FBP. The $^{125}I$-11 kDa FBP was combined with increasing concentrations of unlabeled 11 kDa peptide and immediately incubated with fibrin-coated wells. Bound $^{125}I$-11 kDa FP was assessed by measuring the radioactivity attached to the individual removable fibrin-coated wells. It is also shown that an unrelated protein, egg lysozyme, that was used as a negative control, does not cause inhibition of binding.

As illustrated in FIG. 10 the unlabeled 11 kDa FBP competitively inhibited the binding in a dose dependent manner. $^{125}$I-11 kDa binding to fibrin was decreased by 50% (IC50) by a concentration of 605 nM (6.7 molar excess) of unlabeled 11 kDa FBP. Maximum inhibition was achieved at a concentration of 4 uM (44.4 molar excess) of the unlabeled FBP. As expected, the unrelated protein, egg lysozyme did not inhibit the binding of iodinated 11 kDa to fibrin.

c.) Reversibility of the binding of $^{125}$I-11 kDa FBP to fibrin.

This assay demonstrated that the binding of the 11 kDa fragment to fibrin is reversible and specific. Detachable microtiter wells previously coated with 15 ng of fibrin were incubated with 100 ng/0.1 ml FBB (90 nM) of $^{125}$I-11 kDa for 1 hour at 22° C. The unbound radiolabeled protein was removed by extensive washing with FBB containing 0.1% Tween 20. The bound $^{125}$I-11 kDa FBP was displaced by adding increasing concentrations of unlabeled 11 kDa (10–5,000 nM). The iodinated 11 kDa that remained bound to the removable wells was determined by quantitating the radioactivity attached to the individual wells in a gamma counter. Results were expressed as percentage of control wells incubated with buffer alone.

Figure 11:
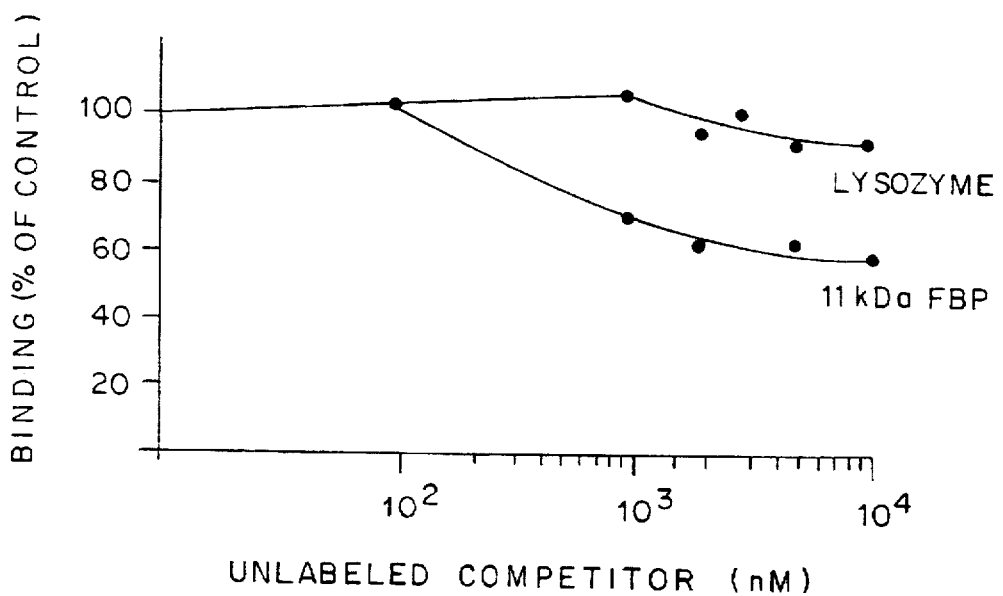
FIG. 11 is a graph representing the reversibility of $^{125}I$-11 kDa binding to fibrin-coated microtiter wells. After a constant concentration of $^{125}I$-11 kDa had been incubated with the fibrin coated wells, the bound iodinated FBP was reversibly displaced by addition of increasing concentrations of unlabeled 11 kDa FBP. An unrelated protein, egg lysozyme, was unable to displace $^{125}I$-11 kDa FBP bound to the fibrin wells.

As shown in FIG. 11, 42% of bound iodinated 11 kDa was reversibly displaced by incubation with 2,000 nM concentration of unlabeled peptide (22.2 molar excess). In contrast, egg lysozyme employed as a negative control was unable to disrupt the binding of the labeled peptide to fibrin.

3. Determination of binding Affinity constants using radio-labeled FBP's.

Affinity constants are determined using Scatchard analysis. The fibrin-coated microtiter plates is used to determine the affinity constants for the binding of fibrin-binding peptides of the present invention to fibrin. The peptide is radiolabeled with $^{125}$I using IODO-BEADs (Pierce Chemical) (Markwell, M. K., *Anal. Biochem.* 125:427–432 (1982)). Various concentrations of the radiolabeled peptide are incubated with the fibrin-coated plates, and the supernatants removed and counted in a gamma counter (Beckman, Biogamma). Bound $^{125}$I-protein is determined by subtracting the counts in the supernatant from the total counts added or by using ELISA microtiter plates with removable wells. The molar concentrations of bound and free fractions of $^{125}$I-protein are used to determine the association constant, Ka, as the slope of the line of the plot of bound/free versus bound.

EXAMPLE VIII

Preparation of Antibodies to Other Fibrin-Binding Peptides

Polyclonal antisera or mAbs specific for other type I repeat modules of fibronectin that indicate high affinity binding to fibrin (e.g., $^{10}$Fn1,$^{11}$Fn1) (see below) are prepared. Antibody titers will be assessed by ELISA as described above, using the antigen (fibrin-binding polypeptide) to coat the wells. The IgG fraction are prepared by ammonium sulfate precipitation (final concentration: 30.3%), followed by dialysis in PBS. Alternatively, Gamma-Bind G Agarose™ will be employed, as described, for the purification of antibody to the 11 kDa fragment. The corresponding peptide, used as antigen, is crosslinked to Tresyl-SEPHAROSE™ and employed for affinity purification of the antiserum.

EXAMPLE IX

Estimation Binding Affinity Constants and Determination the Kinetics of Binding of FN and FBPS of FN to Fibrin Comparison of binding affinity constants of FBPs, t-PA and Fn, to fibrin, by a) scatchard analysis and using the b) BIA-core system. For comparison, binding affinities are compared with t-PA and the cloned t-PA module. Competitive inhibition experiments with labeled and cold FBPs are employed in conjunction with quantitation of the binding constants. Competing, increasing concentrations of an unlabeled ligand with labeled ligand permit estimation of association/dissociation constants. Also, the ability of a ligand (FBP or intact Fn or t-PA) to reverse the binding of an already bound ligand shows the specificity of the interaction of the FBP with fibrin. Quantitation of binding constants establishes the relative fibrin-binding affinities of generated FBPs of the present invention.

Iodination of FBPs.

FBPs are labeled with $^{125}$Iodine for use in the fibrin clot assays, for estimation of binding affinity constants, for in vivo targeting to thrombi, and for labeling with $^{123}$Iodine or $^{131}$Iodine for gamma scintography. The proteins are labeled using either Iodobeads (Pierce), e.g., as described by the manufacturer. Chloramine T is used if the specific activity obtained is not sufficient for a particular study. Free $^{125}$Iodine is removed e.g., by exhaustive dialysis or gel filtration using Sephadex G-25. All modules contain at least one tyrosine and can therefore be labeled with iodine. Moreover, a molecule can be slightly denatured with low molar guanidine to obtain higher specific activity provided that they still retain their fibrin binding activity. Lysines can also be labeled by the known Bolton-Hunter reaction, if suitable. If appropriate, $^{111}$Indium or $^{99m}$Technetium can used to derivatize the FBP for in vivo imagining of thrombi. Initially, the 11 kDa FBP is used for imaging studies, until smaller amino acid sequence of the 11 kDa, or other FBPs, is obtained that retains substantial or significant fibrin-binding activity.

Estimation of binding affinity constants.

a.) Scatchard analysis.

The fibrin coated microtiter plates are used to determine binding affinity constants of the Fn, tPA, the 25.9 kDa and 11 kDa FBPs of Fn, or other FBPs of this invention and the recombinant FBPs by scatchard analysis. Increasing concentrations of the radiolabeled FBPs are incubated with the fibrin coated plates, and the supernatants removed and counted in a gamma counter (Beckman, Biogamma). Bound $^{125}$I protein is determined (CPM in aliquot added minus CPM in the supernatant). Alternatively, bound radiolabeled counts can be directly counted on removable wells. The molar concentrations of bound and free fractions of $^{125}$I-protein are used to determine Ka (association) as the slope of the line of the plot of bound/free versus bound.

b.) Real-time biospecific interaction analysis.

Real-time biospecific interaction analysis is provided using the known method steps of total internal reflection (surface plasmon resonance) for measuring kinetics and binding affinities between Fn and FBPs, to fibrin.

The BIA-core system.

The theory and use of this technology is briefly explained as follows: The phenomenon of surface plasmon resonance (SPR) is used to probe the concentration of biological molecules close to a surface, according to known method steps. The interactions between two proteins are analyzed optically in real time at the surface of a sensor chip. In this system, one of the proteins is immobilized on a hydrogel matrix composed of carboxylated dextran which is positioned with in a flow chamber. The other protein is in an analyte solution which is passed over the surface of the immobilized ligand, and the interaction proceeds between the two proteins/ligands. The concentration of the analyte in the surface layer changes, giving a surface plasmon resonance response which is recorded in real time. The hydrogel is bonded to a gold coated glass slide which is illuminated by a near-infrared light emitting diode. The light is focused through the glass slide onto the gold film in a wedge=shaped beam giving a fixed range of incident angles and the SPR response produced, by the interaction of the two proteins being studied, is monitored by light-sensitive diodes. The information is transmitted to a computer which calculates the angle at which minimum reflection occurs (SPR angle or response angle); the software analyzes the signals from the diode detectors. As SPR is monitored, the light incident on the surface below the angle of total internal reflection is absorbed at one particular angle that is dependent on the index of refraction near the surface. As the protein in the analyte solution (Fn and FBPs) is allowed to flow over the immobilized ligand (fibrin), the refraction index within the matrix incurs subtle changes due to small changes in the refractive index of the protein solution which changes more slowly due to the binding interaction, and hence, concentration, of the analyte protein component interacting with the matrix-bound component. The time course of binding is observed directly. The time course of dissociation is followed by monitoring the SPR signal during elution of the analyte component. For kinetic analyses, the rate of change or the SPR signal is measured. While affinity interactions between two proteins requires immobilization of one of the ligand, in this system it is ideal for determining the binding affinities between Fn and FBPs and fibrin, since fibrin is insoluble and will be immobilized on the hydrogel matrix. To prepare the hydrogel, fibrinogen is chemically linked to the matrix and subsequently treated with thrombin to convert the fibrinogen to fibrin (as in affinity chrchromatography). It is necessary that the fibrinogen is bound to the carboxylated dextran (hydrogel) below its isoelectric point to maintain a positively charged state. Thus fibrinogen will be suspended in a buffer below the pI of 5.5 (e.g. Na citrate, pH 5.0).

EXAMPLE X

Obtaining smaller fragments that retain fibrin-binding activity

Cloning of smaller fragments of FBP corresponding to relevant type I repeat modules of fibronectin is used to determine the minimum amino acid sequence that dictates fibrin-binding activity of FBP's of the present invention. Alternatively, enzymatic digestion may be used to obtain fragments smaller than the ones presently (e.g., the 11 kDa-FBP) demonstrating fibrin-binding activity. These fragments will be purified by standard chromatographic procedures, known by anyone skilled in the art of protein chemistry.

When a repeat module pair, e.g., $^{10}$F1.$^{11}$F1 demonstrates substantial or significant fibrin-binding activity, e.g., as the 11 kDa fragment, progressively smaller fragments are cloned until a loss or reduction in biological activity is observed. In this way, the minimum amino acid sequences required for fibrin-binding activity is determined.

EXAMPLE XI

Figure 32:
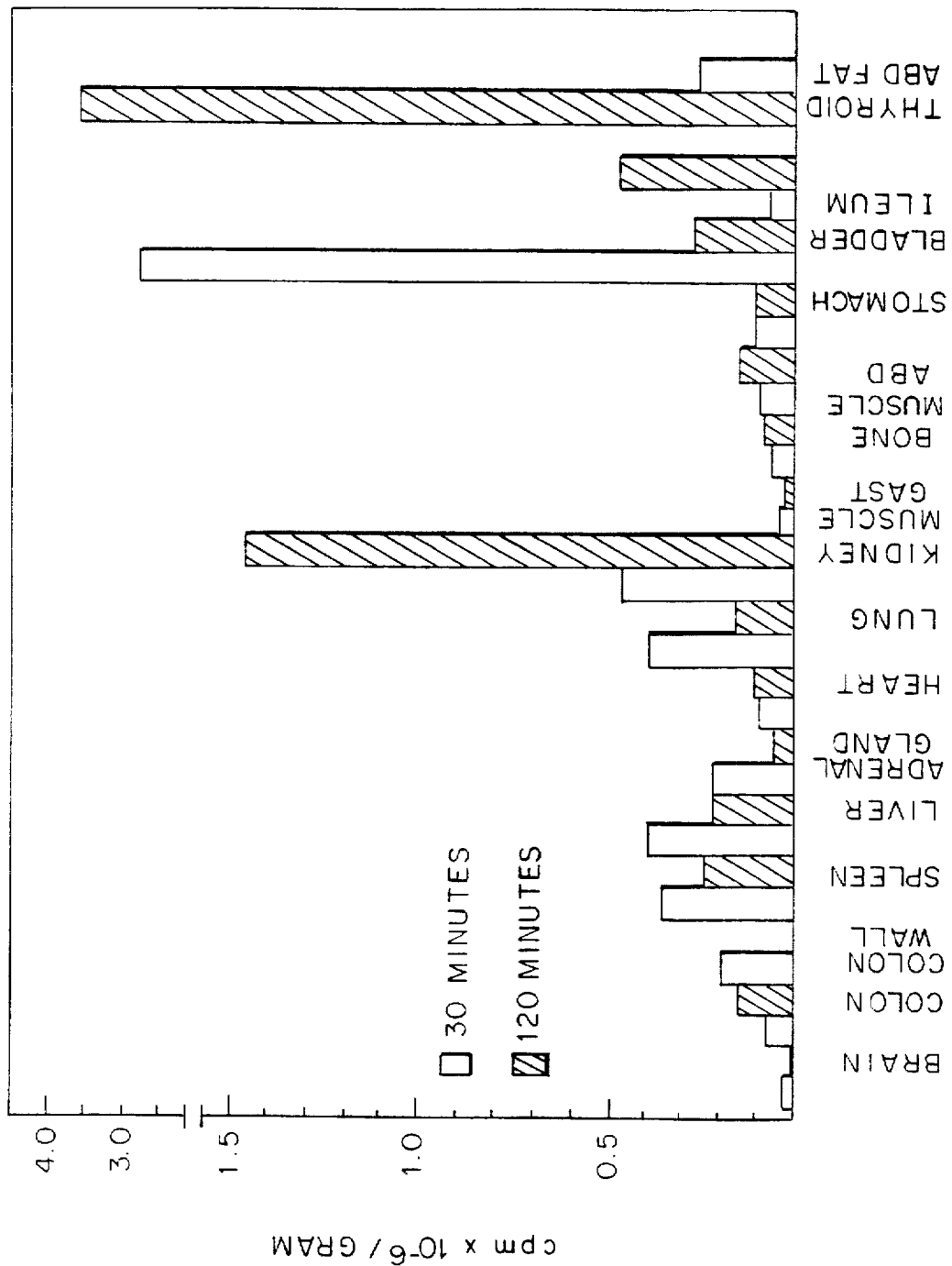
FIG. 32 displays the biodistribution of $^{125}$I-11 kDa FBP in the organs of two rats sacrificed at 30 minutes and at 120 minutes.

Preliminary in vivo studies employing radiolabeled 11 kDa FBP to bind to thrombi-pharmacodynamic studies and biodistribution The purified 11 kDa FBP was radiolabeled with $^{125}$Iodine; the specific activity obtained was 4.0 µCi/µg and the efficiency of labeling was 64%. The TCA precipitable counts were 80%. Four rats were used (430–500 gm). 49.3 µCi (6.9×10$^7$ cpm)/0.36 ml/13.2 µg 11 kDa FBP/per rat was injected into the right femoral vein. Organs were removed at 30 minutes and 120 minutes time points. At various time points, following injection, plasma (0.1 ml) was withdrawn from the left femoral vein and TCA ppt. counts obtained with an aliquot thereof. The pharmacokinetics of radioactivity in the serum is presented in FIG. 31. Counts ranged from 75–80% Trichloroacetic acid precipitable for each time point, indicating that no degradation of the $^{125}$I 11 kDa FBP occurred in the plasma. FIG. 32 displays the biodistribution of $^{125}$I-11 kDa FBP in the organs: Relatively equal distribution of the $^{125}$I-11 kDa FBP was obtained in all organs (100,000–200,000 cpm), except brain, muscle, and bone, which demonstrated the least accumulation of label. Expectedly, the thyroid contained 4.0×10$^6$ at 2 hrs (representative of free iodine) and the kidney and bladder were higher because of the route of excretion.

The biologic half life of the radioiodinated FBP thus was expected to be relatively short, which is important for the diagnostic imaging of thrombi. There was no remarkable accumulation in any organ (FIG. 32) (except the thyroid due to the use of radio labeled iodine).

EXAMPLE XII

Performing in Vivo Studies to assess Efficacy of Targeting FBPS to Thrombi and Injured Vessels, and Pharmacokinetic Studies.

a.) Pharmacokinetics of FBPs (11 kDa FBP and recombinant FBPs) in rats.

Determination of the metabolic behavior of radiolabeled ($^{125}$Iodine) FBP injected into rats: the same protocol is performed as described above herein. The time points for examining TCA precipitable counts in the blood are extended to include 6, 12, and 24 hours (at least 2 rats per time point). $^{125}$I-FBP and/or 11 kDa-FBP are injected into rats as described. Pharmacokinetic modeling is used to determine the half life of radioiodinated FBP in the blood to be used in this example.

Biodistribution (localization and radiation dosimetry): A time course of distribution of radiolabeled FBP in the same organs as shown in FIG. 32 including arteries and veins is analyzed. TCA precipitable $^{125}$I-FBP in the urine over time is determined (excretion rate). TCA soluble counts compared to TCA ppt. counts for each sample indicate proteolytic breakdown over time. The body fluid is mixed with a final concentration of 10% TCA and left on ice for 1 hour, centrifuged, washed, and counted. Each organ is washed and perfused with PBS to remove all traces of blood, before counting.

Determination of thrombus to blood and thrombus to muscle ratios: Before performing the pharmacokinetic studies, the arterial and venous vessels of the same animals are wounded until a thrombus is formed. The ascending vena cava (below the kidneys) and the descending aorta (immediately above the bifurcation) are clamped with a rubber tipped mosquito clamps for 2 hours for the artery and one hour for the vein. A thrombotic occlusion is formed of approximately 1.5 cm length. The specific binding of $^{125}$I-FBP (11 kDa to start) to the preformed thrombus, is determined compared to blood and muscle (wt/wt), over time, following injection. The amount of $^{125}$I-FBP that binds to an injured vessel versus an uninjured vessel is also quantitated. The time for optimal binding is crucial for feasibility of imaging (less than two hours would be considered adequate). The testing of binding to thrombi prepared 24 hours (or longer) ahead (preformed thrombi) compared to newly formed thrombi is also performed. This will determine the efficacy of $^{125}$I-FBP to older and newly forming thrombi.

Dosimetry Studies: Determination of the optimal dose (µCi/µg/kg) required for binding (Dose response) to thrombi: Three different doses were injected following injury, and thrombi removed at the various indicated above. In a preliminary experiment 3.4 µCi/13.3 µg 11 kDa FBP/rat (550 gr) appeared to be a dose that enabled sufficient binding to thrombi compared to blood.

Assessment of the binding of radiolabeled FBPs to thrombi in experimentally de-endothelialized rat and/or rabbit femoral arteries and veins. De-endothelialization of vessels followed by thrombus formation more closely mimics the formation of thrombotic and atherosclerotic lesions in vivo. The enhanced localization of labeled FBPs in de-endothelialized segments of vessels are assessed and compared to normal vessels. For these studies, rabbits can be preferably used because the small diameter of rat vessels (femoral vein and artery) has made it difficult to injure, in past experiments. Rabbit abdominal aortas (20 cm from the insertion in the femoral artery) are injured by inflating (700 mm Hg) a balloon through a 4F fogarty catheter as described (Uehara, et al. (1988) J. Nucl. Med. 29:1264–1267). The balloon is rubbed back and forth and the procedure repeated 6 times before withdrawal of the catheter. De-endothelialization is confirmed by endothelial staining using Evans Blue (9 mg/kg) at sacrifice. $^{125}$I-FBP is injected into rabbits 2 hours after injury and the quantity injected will be proportionally increased (wt) based on the thrombus-binding experiments using rats. Injured tissues are excised and binding of radiolabeled FBPs compared to the binding obtained to other tissues and uninjured comparable vessels.

Assessment of the feasibility of radiolabeled FBPs for imaging thrombi. FBPs (11 kDa FBP) are derivatized with an imaging agent such as $^{125}$Iodine or $^{131}$Iodine, the vessel injured by clamp pressure or de-endothelialization, radiolabeled FBP is injected, and gamma scintigraphy is performed. The amount of $^{131}$Iodine-FBP to be used for imaging is extrapolated from the binding studies using $^{125}$Iodine. Imaging is performed using a GE400 AC/T Starcam. This is a large field of view gamma camera with high resolution and low energy, equipped with a parallel hole collimator. The camera is interfaced to a dedicated nuclear medicine computer for easy transfer to stations for data analysis (region of interest analysis on serial scans). If imaging with $^{123}$I or $^{131}$I is not suitable, other radioisotopes are used, such as $^{111}$Indium (with or without DTPA, a metal chelating group which facilitates labeling), and/or $^{99m}$-Technetium. Retention of biological activity of the derivatized FBP is assessed by ELISA, fibrin-SEPHAROSE™ chromatography, and/or the fibrin clot assay. Efficient in vivo imaging of radiolabeled FBPs is determined in rats and rabbits.

Animal Studies prior to submission of an IND to the FDA for human testing: The following studies are performed in rats and rabbits (or non-rodent animal) by an "outside toxicity testing facility" (e.g., LEBERCO Testing Inc. (Roselle Park, N.J.) or University of Buffalo Toxicology Research Center) or other. Administration of a recombinant radiolabeled and/or unlabeled FBP (e.g., parenterally i.v.) will be by an identical route that would be chosen for human testing. Radiation dosimetry estimates are made for $^{123}$I-and $^{131}$I by using the MIRD formulation. The animal studies can include: (1) acute i.v administration, approximately one injection at 6 dose levels to 4–7 rabbits and 5–10 rats at each dose level, with observation on day 14 and LD$_{50}$ determined; (2) acute toxicity subacute dosing, i.v. administration 5 times per week for two weeks to seven animals; and (3) subchronic i.v. administration, single dose in 6 rabbits and 10 rats for 10 days. Controls receive an equal volume of saline. An appropriate group (e.g., as recommended by the testing facility) is chosen to be analyzed for total clinical blood and urine chemistry, hematological studies, and histology. Particular attention is paid to effects on clotting (e.g., PT and PTT studies); (4) pyrogenicity is tested using the standard LAL test kit; (5) Ames test for mutagenicity is performed on bacteria; (6) sterility testing is performed by inoculation into sterile thioglycollate medium and incubated for 7 days at 37° C.; (7) radiochemical purity and efficiency of radiolabeling of the FBP is done to determine bound radiolabel (performed in our laboratory by HPLC analysis and TCA precipitation).

Studies in animals can also include the following: (1) Efficacy targeting and imaging thrombi at different locations in the body (eg. pulmonary, cardiac microthrombi, deep vein, arterial, brain). (2) Testing of radiolabeled FBP binding to atherosclerotic plaques in an animal model. C57BL/6J mice that have the Ath-1 and Ath-2 homozygous genotype develop atherosclerotic lesions after 14 weeks on a atherogenic diet. These animals will prove useful to test for binding of $^{125}$I-FBP to the lesions. (3) Efficacy of $^{125}$I-FBP binding to thrombi in presence of heparin.

b.) Studies in human volunteers.

Pharmacokinetics/blood analysis for clearing of radioisotope is performed. Toxicity and dosimetry studies such as a dose/range study are conducted, e.g., three dose levels, three patients per dose level, with routine clinical blood tests are made for organ toxicity and effects on blood clotting (also in presence of heparin), urinalysis (route and speed of excretion). The appropriate quantity of protein and radiolabel (pharmacologic dose) is then determined. Efficacy is tested, such as speed and specificity of delivery, imaging at various time points over a 24 hour period. Tests are made on patients with varied lesions e.g., pulmonary thrombi, atrial microthrombi, and/or history of atherosclerosis.

Criteria for Testing in Animals or Humans.

The FBP (recombinant or proteolitically derived) should preferably retain fibrin-binding biological activity at 37° C. following derivatization with an imaging agent. A high specific activity of radiolabeling should preferably be achieved so that reasonably small (µgs or less than 20 mg)

amounts of FBP can be used in vivo (in humans) with good resolution of thrombi or atherosclerotic plaques. The radiolabel should remain bound to the FBP in vivo for an appropriate amount of time to permit adequate imaging of the thrombi or lesion.

The FBP should be small enough and specifically bind with high affinity for rapid delivery and diffusion into clots, but should not be cleared too rapidly to ensure good binding to the clot for specific imaging. High thrombus to blood ratios (very low blood pooling to minimize background) are expected, fast delivery and excretion, and equal organ distribution of the FBP. Alternatively, the binding of the FBP should be reversible for ultimate clearance following its use.

The FBP should bind well to both newly forming clots and older clots and atherosclerotic lesions. The FBP should preferably bind to emboli as well as thrombi, and bind to thrombi in the arterial circulation as well as in veins. Venous thrombi contain more fibrin, while arterial thrombi contain more platelets (Cerquiera, et al. (1992) *Circulation* 85:298–304), and thus FBPs may be more useful in venous thromboses. The FBP should preferably transgress the blood/brain barrier to be useful for imaging cerebrovascular emboli or thrombi.

All references cited herein, including journal articles or abstracts, published or corresponding U.S. or foreign patent applications, issued U.S. or foreign patents, or any other references, are entirely incorporated by reference herein, including all data, tables, figures, and text presented in the cited references. Additionally, the entire contents of the references cited within the references cited herein are also entirely incorporated by reference.

Reference to known method steps, conventional methods steps, known methods or conventional methods is not in any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

---

What is claimed is:

1. A fibrin-binding molecule including at least one peptide selected from the group consisting of:
   a) a portion of the natural fibronectin molecule which includes positions 150–244 of SEQ ID NO:1, wherein the fibrin-binding molecule includes no more of the N-terminal portion of the natural fibronectin molecule than the N-terminal 25.9 kDa proteolytic fragment thereof; and
   b) a portion of the natural fibronectin molecule which includes positions 2122–2232 of SEQ ID NO:1, wherein the fibrin-binding molecule includes no more of the C-terminal portion of the natural fibronectin molecule than the C-terminal 11 kDa proteolytic thereof.

2. A fibrin-binding molecule in accordance with claim 1, wherein said molecule includes peptide a) but not peptide b).

3. A fibrin-binding molecule according to claim 2 wherein said molecule includes a peptide corresponding to an N-terminal portion of fibronectin having an apparent molecular weight of about 25.9 kDa as determined by laser desorption mass spectrometry.

4. A fibrin-binding molecule in accordance with claim 1, wherein said molecule includes peptide b) but not peptide a).

5. A fibrin-binding molecule according to claim 4, wherein said molecule includes a peptide corresponding to a C-terminal portion of fibronectin having an apparent molecular weight of about 11 kDa on sodium dodecyl sulfate polyacrylamide gel electrophoresis.

6. A fibrin-binding molecule in accordance with claim 1, wherein said molecule includes both peptide a) and peptide b).

7. A fibrin-binding molecule in accordance with claim 1, selected from the group consisting of:
   (a) the portion of fibronectin corresponding to positions 150–244 of SEQ ID NO:1; and
   (b) the portion of fibronectin corresponding to positions 2122–2232 of SEQ ID NO:1.

8. A fibrin-binding molecule in accordance with claim 1, further including, bound to said peptide, a therapeutic agent or a diagnostic marker.

9. A molecule according to claim 8, wherein said peptide is labeled with a detectable label.

10. A molecule according to claim 8, wherein said peptide is conjugated to a therapeutic agent.

11. A molecule according to claim 10, wherein said therapeutic agent is selected from a thrombolytic and a fibrinolytic agent.

12. A molecule according to claim 10, wherein said therapeutic agent is a cytotoxic agent.

13. A pharmaceutical composition, comprising a fibrin-binding molecule according to 1, and a pharmaceutically acceptable carrier.

* * * * *

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
        ( A ) LENGTH: 2324 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:1:

```
Gln  Ala  Gln  Gln  Met  Val  Gln  Pro  Gln  Ser  Pro  Val  Ala  Val  Ser  Gln
 1                    5                        10                       15

Ser  Lys  Pro  Gly  Cys  Tyr  Asp  Asn  Gly  Lys  His  Tyr  Gln  Ile  Asn  Gln
               20                       25                       30

Gln  Trp  Glu  Arg  Thr  Tyr  Leu  Gly  Asn  Val  Leu  Val  Cys  Thr  Cys  Tyr
               35                       40                       45

Gly  Gly  Ser  Arg  Gly  Phe  Asn  Cys  Glu  Ser  Lys  Pro  Glu  Ala  Glu  Glu
          50                       55                       60

Thr  Cys  Phe  Asp  Lys  Tyr  Thr  Gly  Asn  Thr  Tyr  Arg  Val  Gly  Asp  Thr
 65                       70                       75                       80

Tyr  Glu  Arg  Pro  Lys  Asp  Ser  Met  Ile  Trp  Asp  Cys  Thr  Cys  Ile  Gly
               85                       90                       95

Ala  Gly  Arg  Gly  Arg  Ile  Ser  Cys  Thr  Ile  Ala  Asn  Arg  Cys  His  Glu
              100                      105                      110

Gly  Gly  Gln  Ser  Tyr  Lys  Ile  Gly  Asp  Thr  Trp  Arg  Arg  Pro  His  Glu
              115                      120                      125

Thr  Gly  Gly  Tyr  Met  Leu  Glu  Cys  Val  Cys  Leu  Gly  Asn  Gly  Lys  Gly
```

```
                    130                        135                          140
  Glu Trp Thr Cys Lys Pro Ile Ala Glu Lys Cys Phe Asp His Ala Ala
  145                     150                 155                     160
  Gly Thr Ser Tyr Val Val Gly Glu Thr Trp Lys Pro Tyr Gln Gly
                      165                 170                     175
  Trp Met Met Val Asp Cys Thr Cys Leu Gly Glu Gly Ser Gly Arg Ile
                  180                 185                 190
  Thr Cys Thr Ser Arg Asn Arg Cys Asn Asp Gln Asp Thr Arg Thr Ser
          195                 200                 205
  Tyr Arg Ile Gly Asp Thr Trp Ser Lys Lys Asp Asn Arg Gly Asn Leu
          210                 215                 220
  Leu Gln Cys Ile Cys Thr Gly Asn Gly Arg Gly Glu Trp Lys Cys Glu
  225                 230                 235                     240
  Arg His Thr Ser Val Gln Thr Thr Ser Ser Gly Ser Gly Pro Phe Thr
                  245                 250                     255
  Asp Val Arg Ala Ala Val Tyr Gln Pro Gln Pro His Pro Gln Pro Pro
              260                 265                 270
  Pro Tyr Gly His Cys Val Thr Asp Ser Gly Val Val Tyr Ser Val Gly
          275                 280                 285
  Met Gln Trp Leu Lys Thr Gln Gly Asn Lys Gln Met Leu Cys Thr Cys
  290                 295                 300
  Leu Gly Asn Gly Val Ser Cys Gln Glu Thr Ala Val Thr Gln Thr Tyr
  305                 310                 315                     320
  Gly Gly Asn Leu Asn Gly Glu Pro Cys Val Leu Pro Phe Thr Tyr Asn
                  325                 330                     335
  Gly Arg Thr Phe Tyr Ser Cys Thr Thr Glu Gly Arg Gln Asp Gly His
                  340                 345                 350
  Leu Trp Cys Ser Thr Thr Ser Asn Tyr Glu Gln Asp Gln Lys Tyr Ser
          355                 360                 365
  Phe Cys Thr Asp His Thr Val Leu Val Gln Thr Gln Gly Gly Asn Ser
      370                 375                 380
  Asn Gly Ala Leu Cys His Phe Pro Phe Leu Tyr Asn Asn His Asn Tyr
  385                 390                 395                     400
  Thr Asp Cys Thr Ser Glu Gly Arg Arg Asp Asn Met Lys Trp Cys Gly
                  405                 410                     415
  Thr Thr Gln Asn Tyr Asp Ala Asp Gln Lys Phe Gly Phe Cys Pro Met
              420                 425                 430
  Ala Ala His Glu Glu Ile Cys Thr Thr Asn Glu Gly Val Met Tyr Arg
          435                 440                 445
  Ile Gly Asp Gln Trp Asp Lys Gln His Asp Met Gly His Met Met Arg
  450                 455                 460
  Cys Thr Cys Val Gly Asn Gly Arg Gly Glu Trp Thr Cys Ile Ala Tyr
  465                 470                 475                     480
  Ser Gln Leu Arg Asp Gln Cys Ile Val Asp Asp Ile Thr Tyr Asn Val
                  485                 490                     495
  Asn Asp Thr Phe His Lys Arg His Glu Glu Gly His Met Leu Asn Cys
              500                 505                 510
  Thr Cys Phe Gly Gln Gly Arg Gly Arg Trp Lys Cys Asp Pro Val Asp
          515                 520                 525
  Gln Cys Gln Asp Ser Glu Thr Gly Thr Phe Tyr Gln Ile Gly Asp Ser
      530                 535                 540
  Trp Glu Lys Tyr Val His Gly Val Arg Tyr Gln Cys Tyr Cys Tyr Gly
  545                 550                 555                     560
```

| | | | | | | | | | | | | | | |
|---|---|---|---|---|---|---|---|---|---|---|---|---|---|---|
| Arg | Gly | Ile | Gly | Glu | Trp | His | Cys | Gln | Pro | Leu | Gln | Tyr | Tyr | Pro | Ser |
| | | | | 565 | | | | | 570 | | | | | 575 | |
| Ser | Ser | Gly | Pro | Val | Glu | Val | Phe | Ile | Thr | Glu | Thr | Pro | Ser | Gln | Pro |
| | | | 580 | | | | | 585 | | | | | 590 | | |
| Asn | Ser | His | Pro | Ile | Gln | Trp | Asn | Ala | Pro | Gln | Pro | Ser | His | Ile | Ser |
| | | | 595 | | | | 600 | | | | | 605 | | | |
| Lys | Tyr | Ile | Leu | Arg | Trp | Arg | Pro | Lys | Asn | Ser | Val | Gly | Arg | Trp | Lys |
| | 610 | | | | | 615 | | | | | 620 | | | | |
| Glu | Ala | Thr | Ile | Pro | Gly | His | Leu | Asn | Ser | Tyr | Thr | Ile | Lys | Gly | Leu |
| 625 | | | | | 630 | | | | | 635 | | | | | 640 |
| Lys | Pro | Gly | Val | Val | Tyr | Glu | Gly | Gln | Leu | Ile | Ser | Ile | Gln | Gln | Tyr |
| | | | | 645 | | | | | 650 | | | | | 655 | |
| Gly | His | Gln | Glu | Val | Thr | Arg | Phe | Asp | Phe | Thr | Thr | Thr | Ser | Thr | Ser |
| | | | | 660 | | | | | 665 | | | | | 670 | |
| Thr | Pro | Val | Thr | Ser | Asn | Thr | Val | Thr | Gly | Glu | Thr | Thr | Pro | Phe | Ser |
| | | | 675 | | | | | 680 | | | | | 685 | | |
| Pro | Leu | Val | Ala | Thr | Ser | Glu | Ser | Val | Thr | Glu | Ile | Thr | Ala | Ser | Ser |
| | | 690 | | | | | 695 | | | | | 700 | | | |
| Phe | Val | Val | Ser | Trp | Val | Ser | Ala | Ser | Asp | Thr | Val | Ser | Gly | Phe | Arg |
| 705 | | | | | 710 | | | | | 715 | | | | | 720 |
| Val | Glu | Tyr | Glu | Leu | Ser | Glu | Glu | Gly | Asp | Glu | Pro | Gln | Tyr | Leu | Asp |
| | | | | 725 | | | | | 730 | | | | | 735 | |
| Leu | Pro | Ser | Thr | Ala | Thr | Ser | Val | Asn | Ile | Pro | Asp | Leu | Leu | Pro | Gly |
| | | | 740 | | | | | 745 | | | | | 750 | | |
| Arg | Lys | Tyr | Ile | Val | Asn | Val | Tyr | Gln | Ile | Ser | Glu | Asp | Gly | Glu | Gln |
| | | | 755 | | | | | 760 | | | | | 765 | | |
| Ser | Leu | Ile | Leu | Ser | Thr | Ser | Gln | Thr | Thr | Ala | Pro | Asp | Ala | Pro | Pro |
| | 770 | | | | | 775 | | | | | 780 | | | | |
| Asp | Pro | Thr | Val | Asp | Gln | Val | Asp | Asp | Thr | Ser | Ile | Val | Val | Arg | Trp |
| 785 | | | | | 790 | | | | | 795 | | | | | 800 |
| Ser | Arg | Pro | Gln | Ala | Pro | Ile | Thr | Gly | Tyr | Arg | Ile | Val | Tyr | Ser | Pro |
| | | | | 805 | | | | | 810 | | | | | 815 | |
| Ser | Val | Glu | Gly | Ser | Ser | Thr | Glu | Leu | Asn | Leu | Pro | Glu | Thr | Ala | Asn |
| | | | 820 | | | | | 825 | | | | | 830 | | |
| Ser | Val | Thr | Leu | Ser | Asp | Leu | Gln | Pro | Gly | Val | Gln | Tyr | Asn | Ile | Thr |
| | | 835 | | | | | 840 | | | | | 845 | | | |
| Ile | Tyr | Ala | Val | Glu | Glu | Asn | Gln | Glu | Ser | Thr | Pro | Val | Val | Ile | Gln |
| | 850 | | | | | 855 | | | | | 860 | | | | |
| Gln | Glu | Thr | Thr | Gly | Thr | Pro | Arg | Ser | Asp | Thr | Val | Pro | Ser | Pro | Arg |
| 865 | | | | | 870 | | | | | 875 | | | | | 880 |
| Asp | Leu | Gln | Phe | Val | Glu | Val | Thr | Asp | Val | Lys | Val | Thr | Ile | Met | Trp |
| | | | | 885 | | | | | 890 | | | | | 895 | |
| Thr | Pro | Pro | Glu | Ser | Ala | Val | Thr | Gly | Tyr | Arg | Val | Asp | Val | Ile | Pro |
| | | | 900 | | | | | 905 | | | | | 910 | | |
| Val | Asn | Pro | Leu | Gly | Glu | His | Gly | Gln | Arg | Leu | Pro | Ile | Ser | Arg | Asn |
| | | | 915 | | | | 920 | | | | | 925 | | | |
| Thr | Phe | Ala | Glu | Val | Thr | Gly | Leu | Ser | Pro | Gly | Val | Thr | Tyr | Tyr | Phe |
| | | | 930 | | | | | 935 | | | | | 940 | | |
| Lys | Val | Phe | Ala | Val | Ser | His | Gly | Arg | Glu | Ser | Lys | Pro | Leu | Thr | Ala |
| 945 | | | | | 950 | | | | | 955 | | | | | 960 |
| Gln | Gln | Thr | Thr | Lys | Leu | Asp | Ala | Pro | Thr | Asn | Leu | Gln | Phe | Val | Asn |
| | | | | 965 | | | | | 970 | | | | | 975 | |
| Glu | Thr | Asp | Ser | Thr | Val | Leu | Val | Arg | Trp | Thr | Pro | Pro | Arg | Ala | Gln |
| | | | 980 | | | | | 985 | | | | | 990 | | |

-continued

```
Ile Thr Gly Tyr Arg Leu Thr Val Gly Leu Thr Arg Arg Gly Gln Pro
        995                 1000                1005
Arg Gln Tyr Asn Val Gly Pro Ser Val Ser Lys Tyr Pro Leu Arg Asn
    1010                1015                1020
Leu Gln Pro Ala Ser Glu Tyr Thr Val Ser Leu Val Ala Ile Lys Gly
1025                1030                1035                1040
Asn Gln Glu Ser Pro Lys Ala Thr Gly Val Phe Thr Thr Leu Gln Pro
                1045                1050                1055
Gly Ser Ser Ile Pro Pro Tyr Asn Thr Glu Val Thr Glu Thr Thr Ile
                1060                1065                1070
Val Ile Thr Trp Thr Pro Ala Pro Arg Ile Gly Phe Lys Leu Gly Val
        1075                1080                1085
Arg Pro Ser Gln Gly Gly Glu Ala Pro Arg Glu Val Thr Ser Asp Ser
        1090                1095                1100
Gly Ser Ile Val Val Ser Gly Leu Thr Pro Gly Val Glu Tyr Val Tyr
1105                1110                1115                1120
Thr Ile Gln Val Leu Arg Asp Gly Gln Glu Arg Asp Ala Pro Ile Val
                1125                1130                1135
Asn Lys Val Val Thr Pro Leu Ser Pro Pro Thr Asn Leu His Leu Glu
                1140                1145                1150
Ala Asn Pro Asp Thr Gly Val Leu Thr Val Ser Trp Glu Arg Ser Thr
        1155                1160                1165
Thr Pro Asp Ile Thr Gly Tyr Arg Ile Thr Thr Thr Pro Thr Asn Gly
        1170                1175                1180
Gln Gln Gly Asn Ser Leu Glu Glu Val Val His Ala Asp Gln Ser Ser
1185                1190                1195                1200
Cys Thr Phe Asp Asn Leu Ser Pro Gly Leu Glu Tyr Asn Val Ser Val
                1205                1210                1215
Tyr Thr Val Lys Asp Asp Lys Glu Ser Val Pro Ile Ser Asp Thr Ile
                1220                1225                1230
Ile Pro Ala Val Pro Pro Pro Thr Asp Leu Arg Phe Thr Asn Ile Gly
        1235                1240                1245
Pro Asp Thr Met Arg Val Thr Trp Ala Pro Pro Pro Ser Ile Asp Leu
        1250                1255                1260
Thr Asn Phe Leu Val Arg Tyr Ser Pro Val Lys Asn Glu Glu Asp Val
1265                1270                1275                1280
Ala Glu Leu Ser Ile Ser Pro Ser Asp Asn Ala Val Val Leu Thr Asn
                1285                1290                1295
Leu Leu Pro Gly Thr Glu Tyr Val Val Ser Val Ser Ser Val Tyr Glu
                1300                1305                1310
Gln His Glu Ser Thr Pro Leu Arg Gly Arg Gln Lys Thr Gly Leu Asp
        1315                1320                1325
Ser Pro Thr Gly Ile Asp Phe Ser Asp Ile Thr Ala Asn Ser Phe Thr
        1330                1335                1340
Val His Trp Ile Ala Pro Arg Ala Thr Ile Thr Gly Tyr Arg Ile Arg
1345                1350                1355                1360
His His Pro Glu His Phe Ser Gly Arg Pro Arg Glu Asp Arg Val Pro
                1365                1370                1375
His Ser Arg Asn Ser Ile Thr Leu Thr Asn Leu Thr Pro Gly Thr Glu
                1380                1385                1390
Tyr Val Val Ser Ile Val Ala Leu Asn Gly Arg Glu Glu Ser Pro Leu
                1395                1400                1405
Leu Ile Gly Gln Gln Ser Thr Val Ser Asp Val Pro Arg Asp Leu Glu
```

-continued

```
            1410                    1415                    1420
Val  Val  Ala  Ala  Thr  Pro  Thr  Ser  Leu  Leu  Ile  Ser  Trp  Asp  Ala  Pro
1425                     1430                    1435                    1440
Ala  Val  Thr  Val  Arg  Tyr  Tyr  Arg  Ile  Thr  Tyr  Gly  Glu  Thr  Gly  Gly
                         1445                    1450                    1455
Asn  Ser  Pro  Val  Gln  Glu  Phe  Thr  Val  Pro  Gly  Ser  Lys  Ser  Thr  Ala
                         1460                    1465                    1470
Thr  Ile  Ser  Gly  Leu  Lys  Pro  Gly  Val  Asp  Tyr  Thr  Ile  Thr  Val  Tyr
                         1475                    1480                    1485
Ala  Val  Thr  Gly  Arg  Gly  Asp  Ser  Pro  Ala  Ser  Ser  Lys  Pro  Ile  Ser
                         1490                    1495                    1500
Ile  Asn  Tyr  Arg  Thr  Glu  Ile  Asp  Lys  Pro  Ser  Gln  Met  Gln  Val  Thr
1505                     1510                    1515                    1520
Asp  Val  Gln  Asp  Asn  Ser  Ile  Ser  Val  Lys  Trp  Leu  Pro  Ser  Ser  Ser
                         1525                    1530                    1535
Pro  Val  Thr  Gly  Tyr  Arg  Val  Thr  Thr  Thr  Pro  Lys  Asn  Gly  Pro  Gly
                         1540                    1545                    1550
Pro  Thr  Lys  Thr  Lys  Thr  Ala  Gly  Pro  Asp  Gln  Thr  Glu  Met  Thr  Ile
                         1555                    1560                    1565
Glu  Gly  Leu  Gln  Pro  Thr  Val  Glu  Tyr  Val  Val  Ser  Val  Tyr  Ala  Gln
                         1570                    1575                    1580
Asn  Pro  Ser  Gly  Glu  Ser  Gln  Pro  Leu  Val  Gln  Thr  Ala  Val  Thr  Asn
1585                     1590                    1595                    1600
Ile  Asp  Arg  Pro  Lys  Gly  Leu  Ala  Phe  Thr  Asp  Val  Asp  Val  Asp  Ser
                         1605                    1610                    1615
Ile  Lys  Ile  Ala  Trp  Glu  Ser  Pro  Gln  Gly  Gln  Val  Ser  Arg  Tyr  Arg
                         1620                    1625                    1630
Val  Thr  Tyr  Ser  Ser  Pro  Glu  Asp  Gly  Ile  His  Glu  Leu  Phe  Pro  Ala
                         1635                    1640                    1645
Pro  Asp  Gly  Glu  Glu  Asp  Thr  Ala  Glu  Leu  Gln  Gly  Leu  Arg  Pro  Gly
                         1650                    1655                    1660
Ser  Glu  Tyr  Thr  Val  Ser  Val  Val  Ala  Leu  His  Asp  Asp  Met  Glu  Ser
1665                     1670                    1675                    1680
Gln  Pro  Leu  Ile  Gly  Thr  Gln  Ser  Thr  Ala  Ile  Pro  Ala  Pro  Thr  Asp
                         1685                    1690                    1695
Leu  Lys  Phe  Thr  Gln  Val  Thr  Pro  Thr  Ser  Leu  Ser  Ala  Gln  Trp  Thr
                         1700                    1705                    1710
Pro  Pro  Asn  Val  Gln  Leu  Thr  Gly  Tyr  Arg  Val  Arg  Val  Thr  Pro  Lys
                         1715                    1720                    1725
Glu  Lys  Thr  Gly  Pro  Met  Lys  Glu  Ile  Asn  Leu  Ala  Pro  Asp  Ser  Ser
                         1730                    1735                    1740
Ser  Val  Val  Val  Ser  Gly  Leu  Met  Val  Ala  Thr  Lys  Tyr  Glu  Val  Ser
1745                     1750                    1755                    1760
Val  Tyr  Ala  Leu  Lys  Asp  Thr  Leu  Thr  Ser  Arg  Pro  Ala  Gln  Gly  Val
                         1765                    1770                    1775
Val  Thr  Thr  Leu  Glu  Asn  Val  Ser  Pro  Pro  Arg  Arg  Ala  Arg  Val  Thr
                         1780                    1785                    1790
Asp  Ala  Thr  Glu  Thr  Thr  Ile  Thr  Ile  Ser  Trp  Arg  Thr  Lys  Thr  Glu
                         1795                    1800                    1805
Thr  Ile  Thr  Gly  Phe  Gln  Val  Asp  Ala  Val  Pro  Ala  Asn  Gly  Gln  Thr
                         1810                    1815                    1820
Pro  Ile  Gln  Arg  Thr  Ile  Lys  Pro  Asp  Val  Arg  Ser  Tyr  Thr  Ile  Thr
1825                     1830                    1835                    1840
```

```
Gly Leu Gln Pro Gly Thr Asp Tyr Lys Ile Tyr Leu Tyr Thr Leu Asn
                1845                1850                1855
Asp Asn Ala Arg Ser Ser Pro Val Val Ile Asp Ala Ser Thr Ala Ile
                1860                1865                1870
Asp Ala Pro Ser Asn Leu Arg Phe Leu Ala Thr Thr Pro Asn Ser Leu
                1875                1880                1885
Leu Val Ser Trp Gln Pro Pro Arg Ala Arg Ile Thr Gly Tyr Ile Ile
                1890                1895                1900
Lys Tyr Glu Lys Pro Gly Ser Pro Pro Arg Glu Val Val Pro Arg Pro
1905                1910                1915                1920
Arg Pro Gly Val Thr Glu Ala Thr Ile Thr Gly Leu Glu Pro Gly Thr
                1925                1930                1935
Glu Tyr Thr Ile Tyr Val Ile Ala Leu Lys Asn Asn Gln Lys Ser Glu
                1940                1945                1950
Pro Leu Ile Gly Arg Lys Lys Thr Asp Glu Leu Pro Gln Leu Val Thr
                1955                1960                1965
Leu Pro His Pro Asn Leu His Gly Pro Glu Ile Leu Asp Val Pro Ser
                1970                1975                1980
Thr Val Gln Lys Thr Pro Phe Val Thr His Pro Gly Tyr Asp Thr Gly
1985                1990                1995                2000
Asn Gly Ile Gln Leu Pro Gly Thr Ser Gly Gln Gln Pro Ser Val Gly
                2005                2010                2015
Gln Gln Met Ile Phe Glu Glu His Gly Phe Arg Arg Thr Thr Pro Pro
                2020                2025                2030
Thr Thr Ala Thr Pro Ile Arg His Arg Pro Arg Pro Tyr Pro Pro Asn
                2035                2040                2045
Val Gly Gln Glu Ala Leu Ser Gln Thr Thr Ile Ser Trp Ala Pro Phe
2050                2055                2060
Gln Asp Thr Ser Glu Tyr Ile Ile Ser Cys His Pro Val Gly Thr Asp
2065                2070                2075                2080
Glu Glu Pro Leu Gln Phe Arg Val Pro Gly Thr Ser Thr Ser Ala Thr
                2085                2090                2095
Leu Thr Gly Leu Thr Arg Gly Ala Thr Tyr Asn Ile Ile Val Glu Ala
                2100                2105                2110
Leu Lys Asp Gln Gln Arg His Lys Val Arg Glu Glu Val Val Thr Val
                2115                2120                2125
Gly Asn Ser Val Asn Glu Gly Leu Asn Gln Pro Thr Asp Asp Ser Cys
                2130                2135                2140
Phe Asp Pro Tyr Thr Val Ser His Tyr Ala Val Gly Asp Glu Trp Glu
2145                2150                2155                2160
Arg Met Ser Glu Ser Gly Phe Lys Leu Leu Cys Gln Cys Leu Gly Phe
                2165                2170                2175
Gly Ser Gly His Phe Arg Cys Asp Ser Ser Arg Trp Cys His Asp Asn
                2180                2185                2190
Gly Val Asn Tyr Lys Ile Gly Glu Lys Trp Asp Arg Gln Gly Glu Asn
                2195                2200                2205
Gly Gln Met Met Ser Cys Thr Cys Leu Gly Asn Gly Lys Gly Glu Phe
                2210                2215                2220
Lys Cys Asp Pro His Glu Ala Thr Cys Tyr Asp Asp Gly Lys Thr Tyr
2225                2230                2235                2240
His Val Gly Glu Gln Trp Gln Lys Glu Tyr Leu Gly Ala Ile Cys Ser
                2245                2250                2255
Cys Thr Cys Phe Gly Gly Gln Arg Gly Trp Arg Cys Asp Asn Cys Arg
                2260                2265                2270
```

```
Arg Pro Gly Gly Glu Pro Ser Pro Glu Gly Thr Thr Gly Gln Ser Tyr
         2275            2280                    2285

Asn Gln Tyr Ser Gln Arg Tyr His Gln Arg Thr Asn Thr Asn Val Asn
         2290            2295            2300

Cys Pro Ile Glu Cys Phe Met Pro Leu Asp Val Gln Ala Asp Arg Glu
2305            2310            2315                    2320

Asp Ser Arg Glu
```

( 2 ) INFORMATION FOR SEQ ID NO:2:

( i ) SEQUENCE CHARACTERISTICS:
  ( A ) LENGTH: 22 nucleotides
  ( B ) TYPE: nucleic acid
  ( C ) STRANDEDNESS: single
  ( D ) TOPOLOGY: linear ( i i ) MOLECULE TYPE: DNA ( x i ) SEQUENCE DESCRIPTION: SEQ ID NO:2:

GCTGAGAAGT GTTTTGATCA TG  22

( 2 ) INFORMATION FOR SEQ ID NO:3:

( i ) SEQUENCE CHARACTERISTICS:
  ( A ) LENGTH: 33 nucleotides
  ( B ) TYPE: nucleic acid
  ( C ) STRANDEDNESS: single
  ( D ) TOPOLOGY: linear ( i i ) MOLECULE TYPE: DNA ( x i ) SEQUENCE DESCRIPTION: SEQ ID NO:3:

TAATGGATCC TTAAGAGGTG TGCCTCTCAC ACT  33

( 2 ) INFORMATION FOR SEQ ID NO:4:

( i ) SEQUENCE CHARACTERISTICS:
  ( A ) LENGTH: 37 amino acids
  ( B ) TYPE: amino acid
  ( C ) STRANDEDNESS: single
  ( D ) TOPOLOGY: linear ( i i ) MOLECULE TYPE: peptide ( x i ) SEQUENCE DESCRIPTION: SEQ ID NO:4:

```
Cys Phe Glu Pro Gln Leu Leu Arg Phe Phe His Lys Asn Glu Ile Trp
1               5                   10                  15

Tyr Arg Thr Glu Gln Ala Ala Val Ala Arg Cys Gln Cys Lys Gly Pro
            20              25                  30

Asp Ala His Cys Gln
            35
```

( 2 ) INFORMATION FOR SEQ ID NO:5:

( i ) SEQUENCE CHARACTERISTICS:
  ( A ) LENGTH: 39 amino acids
  ( B ) TYPE: amino acid
  ( C ) STRANDEDNESS: single
  ( D ) TOPOLOGY: linear ( i i ) MOLECULE TYPE: peptide ( x i ) SEQUENCE DESCRIPTION: SEQ ID NO:5:

```
Cys Arg Asp Glu Lys Thr Gln Met Ile Tyr Gln Gln His Gln Ser Trp
1               5                   10                  15
```

```
Leu Arg Pro Val Leu Arg Ser Asn Arg Val Glu Tyr Cys Trp Cys Asn
         20              25                      30

Ser Gly Arg Ala Gln Cys His
         35
```

( 2 ) INFORMATION FOR SEQ ID NO:6:

( i ) SEQUENCE CHARACTERISTICS:
        ( A ) LENGTH: 20 nucleotides
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:6:

CAGGCTCAGC AAATGGTTCA      20

( 2 ) INFORMATION FOR SEQ ID NO:7:

( i ) SEQUENCE CHARACTERISTICS:
        ( A ) LENGTH: 35 nucleotides
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:7:

TAATGGATCC TTATTCAGGT TTACTTTCGC AGTTA      35

( 2 ) INFORMATION FOR SEQ ID NO:8:

( i ) SEQUENCE CHARACTERISTICS:
        ( A ) LENGTH: 28 nucleotides
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:8:

TAATGGATCC TTATGCGATG GTACAGCT      28

( 2 ) INFORMATION FOR SEQ ID NO:9:

( i ) SEQUENCE CHARACTERISTICS:
        ( A ) LENGTH: 42 nucleotides
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:9:

TCAGTTAAGC TTGGACAAAA GAGATGACTC GTGCTTTGAC CC      42

( 2 ) INFORMATION FOR SEQ ID NO:10:

( i ) SEQUENCE CHARACTERISTICS:
        ( A ) LENGTH: 39 nucleotides
        ( B ) TYPE: nucleic acid
        ( C ) STRANDEDNESS: single
        ( D ) TOPOLOGY: linear

```
( i i ) MOLECULE TYPE: DNA ( x i ) SEQUENCE DESCRIPTION: SEQ ID NO:10:

TTCAGTTGGA TCCTTAAGAT GAATCACATC TGAAATGAC                              3 9
```